US011957115B2

(12) United States Patent
Howell et al.

(10) Patent No.: US 11,957,115 B2
(45) Date of Patent: Apr. 16, 2024

(54) GENETICALLY MODIFIED MOUSE EXPRESSING HUMAN APOE4 AND MOUSE TREM2 P.R47H AND METHODS OF USE THEREOF

(71) Applicants: The Jackson Laboratory, Bar Harbor, ME (US); Indiana University Research and Technology Corporation, Indianapolis, IN (US)

(72) Inventors: Gareth Howell, Bar Harbor, ME (US); Michael Sasner, Bar Harbor, ME (US); Gregory Carter, Bar Harbor, ME (US); Bruce Lamb, Carmel, IN (US)

(73) Assignees: The Jackson Laboratory, Bar Harbor, ME (US); Indiana University Research and Technology Corporation, Indianapolis, IN (US)

( * ) Notice: Subject to any disclaimer, the term of this patent is extended or adjusted under 35 U.S.C. 154(b) by 753 days.

(21) Appl. No.: 16/496,261

(22) PCT Filed: Mar. 21, 2018

(86) PCT No.: PCT/US2018/023565
§ 371 (c)(1),
(2) Date: Sep. 20, 2019

(87) PCT Pub. No.: WO2018/175581
PCT Pub. Date: Sep. 27, 2018

(65) Prior Publication Data
US 2020/0022343 A1    Jan. 23, 2020

Related U.S. Application Data

(60) Provisional application No. 62/474,358, filed on Mar. 21, 2017.

(51) Int. Cl.
*A01K 67/0278* (2024.01)
*C07K 14/705* (2006.01)
*C07K 14/775* (2006.01)
*G01N 33/68* (2006.01)

(52) U.S. Cl.
CPC .... *A01K 67/0278* (2013.01); *C07K 14/70503* (2013.01); *C07K 14/775* (2013.01); *G01N 33/6896* (2013.01); *A01K 2217/056* (2013.01); *A01K 2217/072* (2013.01); *A01K 2217/15* (2013.01); *A01K 2227/105* (2013.01); *A01K 2267/0312* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 6,046,381 A | 4/2000 | Mucke et al. | |
| 6,175,057 B1 * | 1/2001 | Mucke ............... | C12N 15/8509 800/12 |
| 6,453,242 B1 | 9/2002 | Eisenberg et al. | |
| 6,534,261 B1 | 3/2003 | Coxx, III et al. | |
| 6,534,643 B1 | 3/2003 | Eisen | |
| 6,607,882 B1 | 8/2003 | Coxx, III et al. | |
| 6,830,910 B1 | 12/2004 | Eisen | |
| 6,858,716 B2 | 2/2005 | Eisen | |
| 7,294,754 B2 | 11/2007 | Poueymirou et al. | |
| 7,576,259 B2 | 8/2009 | Davidson et al. | |
| 7,659,442 B2 | 2/2010 | Poueymirou et al. | |
| 8,420,782 B2 | 4/2013 | Bonas et al. | |
| 8,440,431 B2 | 5/2013 | Voytas et al. | |
| 8,440,432 B2 | 5/2013 | Voytas et al. | |
| 8,450,107 B1 | 5/2013 | Zhang et al. | |
| 8,450,471 B2 | 5/2013 | Voytas et al. | |
| 2005/0064474 A1 | 3/2005 | Urnov et al. | |
| 2006/0160079 A1 | 7/2006 | Lane | |
| 2006/0188987 A1 | 8/2006 | Guschin et al. | |

(Continued)

FOREIGN PATENT DOCUMENTS

| | | |
|---|---|---|
| CN | 1206421 A | 1/1999 |
| CN | 102137680 A | 7/2011 |

(Continued)

OTHER PUBLICATIONS

Houdebine et al., Production of pharmaeutical proteins from trasngenic animals J. of Biotechnology, 1994, 269-287; p. 271, col. 2.*

(Continued)

*Primary Examiner* — Maria G Leavitt

(74) *Attorney, Agent, or Firm* — Wolf, Greenfield & Sacks, P.C.

(57) ABSTRACT

Genetically modified mice characterized by one or more symptoms or signs associated with expression of human APOE4p and mouse Trem2p and relevant to non-familial late-onset Alzheimer's disease are provided wherein the genome of the mouse includes: 1) a DNA sequence encoding a human APOE4 protein (APOE4p) operably linked to a promoter; and 2) a DNA sequence encoding a mouse Trem2 protein having a mutation p,R47H (Trem2p) operably linked to a promoter, such that the mouse expresses human APOE4p and mouse Trem2p. Methods ace provided for screening for a compound for use in the treatment of Alzheimer's disease using such genetically modified mice.

6 Claims, 5 Drawing Sheets

Specification includes a Sequence Listing.

(56) References Cited

U.S. PATENT DOCUMENTS

| | | |
|---|---|---|
| 2006/0272038 A1 | 11/2006 | De Vivo et al. |
| 2008/0131962 A1 | 6/2008 | Miller |
| 2013/0137161 A1 | 5/2013 | Zhang et al. |
| 2013/0137174 A1 | 5/2013 | Zhang et al. |
| 2021/0195879 A1 | 7/2021 | Howell et al. |

FOREIGN PATENT DOCUMENTS

| | | | |
|---|---|---|---|
| CN | 102177436 A | | 9/2011 |
| EP | 1063298 A2 | | 12/2000 |
| JP | 2001-017028 A | | 1/2001 |
| JP | 2001017028 | * | 1/2001 |
| JP | 2008-000027 A | | 1/2008 |
| WO | WO 2007/014275 A2 | | 2/2007 |
| WO | WO 2014/074942 A1 | | 5/2014 |
| WO | WO2018015573 | * | 1/2018 |
| WO | WO 2020/154348 A1 | | 7/2020 |
| WO | WO 2022/132768 A1 | | 6/2022 |

OTHER PUBLICATIONS

International Preliminary Report on Patentability in connection with Application No. PCT/US2018/023565 dated Jul. 12, 2018.
International Search Report and Written Opinion in connection with Application No. PCT/US2018/023565 dated Oct. 3, 2019.
[No Author Listed], Building Better Mouse Models for Late-Onset Alzheimer's. Alzforum. Jan. 20, 2017;8 pgs. https://www.alzforum.org/news/research-news/building better-mouse-models-late-onset-alzheimers [last accessed Dec. 17, 2019].
Genbank Submission; NIH/NCBI, Accession No. AAB59397. Das et al., Nov. 9, 1994. 2 pgs.
Genbank Submission; NIH/NCBI, Accession No. NP_001259007. Leyns et al., Dec. 8, 2019. 3 pgs.
Huang et al., ApoE2, ApoE3, and ApoE4 Differentially Stimulate APP Transcription and Aβ Secretion. Cell. Jan. 26, 2017;168(3):427-441.e21. doi: 10.1016/j.cell.2016.12.044. Epub Jan. 19, 2017.
Jiang et al., Upregulation of TREM2 ameliorates neuropathology and rescues spatial cognitive impairment in a transgenic mouse model of Alzheimer's disease. Neuropsychopharmacology. Dec. 2014;39(13):2949-62. doi: 10.1038/npp.2014.164. Epub Jul. 22, 2014.
Extended European Search Report for Application No. EP 18770741.9 dated Nov. 26, 2020.
Extended European Search Report, dated Feb. 2, 2022 for Application No. EP 19821744.0.
International Search Report and Written Opinion for Application No. PCT/US2019/038401 dated Oct. 9, 2019.
International Preliminary Report on Patentability for Application No. PCT/US2019/038401 dated Dec. 30, 2020.
[No Author Listed], Unbiased Screen Fingers TREM2 Ligands that Promote A[beta] Uptake. Alzforum. Sep. 27, 2016. Retrieved Nov. 16, 2020. https://www.alzforum.org/news/conference-coverage/unbiased-screen-fingers-trem2-ligands-promote-av-uptake. 5 pages.
Abboud et al., Analysis of the mouse CSF-1 gene promoter in a transgenic mouse model. J Histochem Cytochem. Jul. 2003;51(7):941-9. doi: 10.1177/002215540305100709.
Altschul et al., Basic local alignment search tool. J Mol Biol. Oct. 5, 1990;215(3):403-10. doi: 10.1016/S0022-2836(05)80360-2.
Altschul et al., Gapped BLAST and PSI-BLAST: a new generation of protein database search programs. Nucleic Acids Res. Sep. 1, 1997;25(17):3389-402. doi: 10.1093/nar/25.17.3389.
Ansai et al., Efficient targeted mutagenesis in medaka using custom-designed transcription activator-like effector nucleases. Genetics. Mar. 2013;193(3):739-49. doi: 10.1534/genetics.112.147645. Epub Jan. 3, 2013.
Atagi et al., Apolipoprotein E Is a Ligand for Triggering Receptor Expressed on Myeloid Cells 2 (TREM2). J Biol Chem. Oct. 23, 2015;290(43):26043-50. doi: 10.1074/jbc.M115.679043. Epub Sep. 15, 2015.
Barrangou et al., CRISPR provides acquired resistance against viruses in prokaryotes. Science. Mar. 23, 2007;315(5819):1709-12. doi: 10.1126/science.1138140.
Beerli et al., Engineering polydactyl zinc-finger transcription factors. Nat Biotechnol. Feb. 2002;20(2):135-41. doi: 10.1038/nbt0202-135.
Belfort et al., Homing endonucleases: keeping the house in order. Nucleic Acids Res. Sep. 1, 1997;25(17):3379-88. doi: 10.1093/nar/25.17.3379.
Bitinaite et al., FokI dimerization is required for DNA cleavage. Proc Natl Acad Sci U S A. Sep. 1, 1998;95(18):10570-5. doi: 10.1073/pnas.95.18.10570.
Boch et al., Breaking the code of DNA binding specificity of TAL-type III effectors. Science. Dec. 11, 2009;326(5959):1509-12. doi: 10.1126/science.1178811.
Bonas et al., Genetic and structural characterization of the avirulence gene avrBs3 from *Xanthomonas campestris* pv. vesicatoria. Mol Gen Genet. Jul. 1989;218(1):127-36. doi: 10.1007/BF00330575.
Bu et al., Apolipoprotein E and its receptors in Alzheimer's disease: pathways, pathogenesis and therapy. Nat Rev Neurosci. May 2009;10(5):333-44. doi: 10.1038/nrn2620. Epub Apr. 2, 2009.
Buehr et al., Genesis of embryonic stem cells. Philos Trans R Soc Lond B Biol Sci. Aug. 29, 2003;358(1436):1397-402; discussion 1402. doi: 10.1098/rstb.2003.1327.
Carbery et al., Targeted genome modification in mice using zinc-finger nucleases. Genetics. Oct. 2010;186(2):451-9. doi: 10.1534/genetics.110.117002. Epub Jul. 13, 2010.
Carlson et al., Efficient TALEN-mediated gene knockout in livestock. Proc Natl Acad Sci U S A. Oct. 23, 2012;109(43):17382-7. doi: 10.1073/pnas.1211446109. Epub Oct. 1, 2012.
Carroll D., A CRISPR approach to gene targeting. Mol Ther. Sep. 2012;20(9):1658-60. doi: 10.1038/mt.2012.171.
Castillo et al., Comparative profiling of cortical gene expression in Alzheimer's disease patients and mouse models demonstrates a link between amyloidosis and neuroinflammation. Sci Rep. Dec. 19, 2017;7(1):17762. doi: 10.1038/s41598-017-17999-3.
Chan et al., ApoE4 expression accelerates hippocampus-dependent cognitive deficits by enhancing Aβ impairment of insulin signaling in an Alzheimer's disease mouse model. Sci Rep. May 18, 2016;6:26119.
Chang et al., Genome editing with RNA-guided Cas9 nuclease in zebrafish embryos. Cell Res. Apr. 2013;23(4):465-72. doi: 10.1038/cr.2013.45. Epub Mar. 26, 2013.
Cheng-Hathaway et al., The Trem2 R47H variant confers loss-of-function-like phenotypes in Alzheimer's disease. Mol Neurodegener. Jun. 1, 2018;13(1):29. doi: 10.1186/s13024-018-0262-8.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Choo et al., Advances in zinc finger engineering. Curr Opin Struct Biol. Aug. 2000;10(4):411-6. doi: 10.1016/s0959-440x(00)00107-x.
Christian et al., Targeting DNA double-strand breaks with TAL effector nucleases. Genetics. Oct. 2010;186(2):757-61. doi: 10.1534/genetics.110.120717. Epub Jul. 26, 2010.
Cong et al., Multiplex genome engineering using CRISPR/Cas systems. Science. Feb. 15, 2013;339(6121):819-23. doi: 10.1126/science.1231143. Epub Jan. 3, 2013.
Cui et al., Targeted integration in rat and mouse embryos with zinc-finger nucleases. Nat Biotechnol. Jan. 2011;29(1):64-7. doi: 10.1038/nbt.1731. Epub Dec. 12, 2010.
Deltcheva et al., CRISPR RNA maturation by trans-encoded small RNA and host factor RNase III. Nature. Mar. 310, 2011;471(7340):602-7. doi: 10.1038/nature09886.
Dibattista et al., Identification and modification of amyloid-independent phenotypes of APOE4 mice. Exp Neurol. Jun. 2016;280:97-105. doi: 10.1016/j.expneurol.2016.04.014. Epub Apr. 14, 2016.
Dingwall et al., The nucleoplasmin nuclear location sequence is larger and more complex than that of SV-40 large T antigen. J Cell Biol. Sep. 1988;107(3):841-9. doi: 10.1083/jcb.107.3.841.
Dopie et al., Active maintenance of nuclear actin by importin 9 supports transcription. Proc Natl Acad Sci U S A. Feb. 28, 2012;109(9):E544-52. doi: 10.1073/pnas.1118880109. Epub Feb. 9, 2012.

(56) References Cited

OTHER PUBLICATIONS

Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. doi: 10.1073/pnas.1208507109. Epub Sep. 4, 2012.
Haft et al., A guild of 45 CRISPR-associated (Cas) protein families and multiple CRISPR/Cas subtypes exist in prokaryotic genomes. PLoS Comput Biol. Nov. 2005;1(6):e60. doi: 10.1371/journal.pcbi.0010060. Epub Nov. 11, 2005.
Hauschild et al., Efficient generation of a biallelic knockout in pigs using zinc-finger nucleases. Proc Natl Acad Sci U S A. Jul. 19, 2011;108(29):12013-7. doi: 10.1073/pnas.1106422108. Epub Jul. 5, 2011.
Hockemeyer et al., Genetic engineering of human pluripotent cells using TALE nucleases. Nat Biotechnol. Jul. 7, 2011;29(8):731-4. doi: 10.1038/nbt.1927.
Holtzman et al., Apolipoprotein E isoform-dependent amyloid deposition and neuritic degeneration in a mouse model of Alzheimer's disease. Proc Natl Acad Sci U S A. Mar. 14, 2000;97(6):2892-7. doi: 10.1073/pnas.050004797.
Horvath et al., CRISPR/Cas, the immune system of bacteria and archaea. Science. Jan. 8, 2010;327(5962):167-70. doi: 10.1126/science.1179555.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Isalan et al., A rapid, generally applicable method to engineer zinc fingers illustrated by targeting the HIV-1 promoter. Nat Biotechnol. Jul. 2001;19(7):656-60. doi: 10.1038/90264.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Kalderon et al., A short amino acid sequence able to specify nuclear location. Cell. Dec. 1984;39(3 Pt 2):499-509. doi: 10.1016/0092-8674(84)90457-4.
Karlin et al., Applications and statistics for multiple high-scoring segments in molecular sequences. Proc Natl Acad Sci U S A. Jun. 15, 1993;90(12):5873-7. doi: 10.1073/pnas.90.12.5873.
Karlin et al., Methods for assessing the statistical significance of molecular sequence features by using general scoring schemes. Proc Natl Acad Sci U S A. Mar. 1990;87(6):2264-8. doi: 10.1073/pnas.87.6.2264.
Kay et al., A bacterial effector acts as a plant transcription factor and induces a cell size regulator. Science. Oct. 26, 2007;318(5850):648-51. doi: 10.1126/science.1144956.
Kim et al., Chimeric restriction endonuclease. Proc Natl Acad Sci U S A. Feb. 1, 1994;91(3):883-7. doi: 10.1073/pnas.91.3.883.
Kim et al., Hybrid restriction enzymes: zinc finger fusions to Fok I cleavage domain. Proc Natl Acad Sci U S A. Feb. 6, 1996;93(3):1156-60. doi: 10.1073/pnas.93.3.1156.
Korvatska et al., R47H Variant of TREM2 Associated With Alzheimer Disease in a Large Late-Onset Family: Clinical, Genetic, and Neuropathological Study. JAMA Neurol. Aug. 2015;72(8):920-7. doi: 10.1001/jamaneurol.2015.0979.
Kraus et al., A more cost effective and rapid high percentage germ-line transmitting chimeric mouse generation procedure via microinjection of 2-cell, 4-cell, and 8-cell embryos with ES and iPS cells. Genesis. Jun. 2010;48(6):394-9. doi: 10.1002/dvg.20627.
Lei et al., Efficient targeted gene disruption in Xenopus embryos using engineered transcription activator-like effector nucleases (TALENs). Proc Natl Acad Sci U S A. Oct. 23, 2012;109(43):17484-9. doi: 10.1073/pnas.1215421109. Epub Oct. 8, 2012.

Li et al., Alteration of the cleavage distance of Fok I restriction endonuclease by insertion mutagenesis. Proc Natl Acad Sci U S A. Apr. 1, 1993;90(7):2764-8. doi: 10.1073/pnas.90.7.2764.
Li et al., Functional domains in Fok I restriction endonuclease. Proc Natl Acad Sci U S A. May 15, 1992;89(10):4275-9. doi: 10.1073/pnas.89.10.4275.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Majumdar et al., Xenogeneic expression of human stem cell factor in transgenic mice mimics codominant c-kit mutations. Blood. Apr. 15, 1996;87(8):3203-11.
Makarova et al., Evolution and classification of the CRISPR-Cas systems. Nat Rev Microbiol. Jun. 2011;9(6):467-77. doi: 10.1038/nrmicro2577. Epub May 9, 2011.
Makkerh et al., Comparative mutagenesis of nuclear localization signals reveals the importance of neutral and acidic amino acids. Curr Biol. Aug. 1, 1996;6(8):1025-7. doi: 10.1016/s0960-9822(02)00648-6.
Mali et al., RNA-guided human genome engineering via Cas9. Science. Feb. 15, 2013;339(6121):823-6. doi: 10.1126/science.1232033. Epub Jan. 3, 2013.
Marraffini et al., CRISPR interference: RNA-directed adaptive immunity in bacteria and archaea. Nat Rev Genet. Mar. 2010;11(3):181-90. doi: 10.1038/nrg2749.
McBurney et al., Murine PGK-1 promoter drives widespread but not uniform expression in transgenic mice. Dev Dyn. Aug. 1994;200(4):278-93. doi: 10.1002/aja.1002000403.
McLane et al., Nuclear localization signals and human disease. IUBMB Life. Jul. 2009;61(7):697-706. doi: 10.1002/iub.194.
Miller et al., A TALE nuclease architecture for efficient genome editing. Nat Biotechnol. Feb. 2011;29(2):143-8. doi: 10.1038/nbt.1755. Epub Dec. 22, 2010.
Moore et al., Improved somatic mutagenesis in zebrafish using transcription activator-like effector nucleases (TALENs). PLoS One. 2012;7(5):e37877. doi: 10.1371/journal.pone.0037877. Epub May 24, 2012.
Moscou et al., A simple cipher governs DNA recognition by TAL effectors. Science. Dec. 11, 2009;326(5959):1501. doi: 10.1126/science.1178817.
Murray et al., APOE ε4 is also required in TREM2 R47H variant carriers for Alzheimer's disease to develop. Neuropathol Appl Neurobiol. Feb. 2019;45(2):183-186. doi: 10.1111/nan.12474. Epub Mar. 1, 2018.
Myers et al., Optimal alignments in linear space. Comput Appl Biosci. Mar. 1988;4(1):11-7. doi: 10.1093/bioinformatics/4.1.11.
Nagy et al., Embryonic stem cells alone are able to support fetal development in the mouse. Development. Nov. 1990;110(3):815-21.
Onos et al., Toward more predictive genetic mouse models of Alzheimer's disease. Brain Res Bull. Apr. 2016;122:1-11. doi: 10.1016/j.brainresbull.2015.12.003. Epub Dec. 17, 2015.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Pabo et al., Design and selection of novel Cys2His2 zinc finger proteins. Annu Rev Biochem. 2001;70:313-40. doi: 10.1146/annurev.biochem.70.1.313.
Porteus et al., Gene targeting using zinc finger nucleases. Nat Biotechnol. Aug. 2005;23(8):967-73. doi: 10.1038/nbt1125.
Qi et al., Repurposing CRISPR as an RNA-guided platform for sequence-specific control of gene expression. Cell. Feb. 28, 2013;152(5):1173-83. doi: 10.1016/j.cell.2013.02.022. Erratum in: Cell. Feb. 4, 2021;184(3):844.
Radu et al., An in vivo assay to test blood vessel permeability. J Vis Exp. Mar. 16, 2013;(73):e50062. doi: 10.3791/50062.
Roberts et al., REBASE: restriction enzymes and methyltransferases. Nucleic Acids Res. Jan. 1, 2003;31(1):418-20. doi: 10.1093/nar/gkg069.
Sasner, M. Novel mouse models of late-onset Alzheimer's disease based on GWAS. Model-AD. 1 page.

(56) References Cited

OTHER PUBLICATIONS

Scholze et al., TAL effectors are remote controls for gene activation. Curr Opin Microbiol. Feb. 2011;14(1):47-53. doi: 10.1016/j.mib.2010.12.001. Epub Jan. 5, 2011.

Schornack et al., Gene-for-gene-mediated recognition of nuclear-targeted AvrBs3-like bacterial effector proteins. J Plant Physiol. Feb. 2006;163(3):256-72. doi: 10.1016/j.jplph.2005.12.001. Epub Jan. 5, 2006.

Schorpp et al., The human ubiquitin C promoter directs high ubiquitous expression of transgenes in mice. Nucleic Acids Res. May 1, 1996;24(9):1787-8. doi: 10.1093/nar/24.9.1787.

Segal et al., Custom DNA-binding proteins come of age: polydactyl zinc-finger proteins. Curr Opin Biotechnol. Dec. 2001;12(6):632-7. doi: 10.1016/s0958-1669(01)00272-5.

Sera et al., Rational design of artificial zinc-finger proteins using a nondegenerate recognition code table. Biochemistry. Jun. 4, 2002;41(22):7074-81. doi: 10.1021/bi020095c.

Shao et al., Genetics of Alzheimer's disease: From pathogenesis to clinical usage. J Clin Neurosci. Nov. 2017;45:1-8. doi: 10.1016/j.jocn.2017.06.074. Epub Aug. 30, 2017.

Shen et al., Generation of gene-modified mice via Cas9/RNA-mediated gene targeting. Cell Res. May 2013;23(5):720-3. doi: 10.1038/cr.2013.46. Epub Apr. 2, 2013.

Stroud et al., Gene knockout using transcription activator-like effector nucleases (TALENs) reveals that human NDUFA9 protein is essential for stabilizing the junction between membrane and matrix arms of complex I. J Biol Chem. Jan. 18, 2013;288(3):1685-90. doi: 10.1074/jbc.C112.436766. Epub Dec. 5, 2012.

Sung et al., Knockout mice created by TALEN-mediated gene targeting. Nat Biotechnol. Jan. 2013;31(1):23-4. doi: 10.1038/nbt.2477.

Tambini et al., ApoE4 upregulates the activity of mitochondria-associated ER membranes. EMBO Rep. Jan. 2016;17(1):27-36. doi: 10.15252/embr.201540614. Epub Nov. 12, 2015.

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Watt et al., Direct and rapid modification of a porcine xenoantigen gene (GGTA1). Transplantation. Oct. 15, 2006;82(7):975-8. doi: 10.1097/01.tp.0000229431.96906.33.

Wefers et al., Direct production of mouse disease models by embryo microinjection of TALENs and oligodeoxynucleotides. Proc Natl Acad Sci U S A. Mar. 5, 2013;110(10):3782-7. doi: 10.1073/pnas.1218721110. Epub Feb. 20, 2013.

PCT/US2018/023565, Jul. 12, 2018, International Search Report and Written Opinion.

PCT/US2018/023565, Oct. 3, 2019, International Preliminary Report on Patentability.

Fitz et al., Trem2 deficiency differentially affects phenotype and transcriptome of human APOE3 and APOE4 mice. Mol Neurodegener. Jul. 23, 2020;15(1):41. doi: 10.1186/s13024-020-00394-4.

Onos et al., Enhancing face validity of mouse models of Alzheimer's disease with natural genetic variation. PLoS Genet. May 31, 2019;15(5):e1008155. doi: 10.1371/journal.pgen.1008155.

Org et al., Using the natural variation of mouse populations to understand host-gut microbiome interactions. Drug Discov Today Dis Models. 2018 Summer;28:61-71. doi: 10.1016/j.ddmod.2019.08.003. Epub Aug. 29, 2019. Author Manuscript, 18 pages.

* cited by examiner

GENETICALLY MODIFIED MOUSE EXPRESSING HUMAN APOE4 AND MOUSE TREM2 P.R47H AND METHODS OF USE THEREOF

RELATED APPLICATIONS

This application is a national stage filing under 35 U.S.C. § 371 of international application number PCT/US2018/023565, filed Mar. 21, 2018, which was published under PCT Article 21(2) in English and claims the benefit under 35 U.S.C. § 119(e) of U.S. provisional application No. 62/474,358, filed Mar. 21, 2017, each of which is incorporated herein by reference in its entirety.

GOVERNMENT SUPPORT

This invention was made with government support under AG054345 awarded by the National Institutes of Health. The government has certain rights in the invention.

FIELD OF THE INVENTION

The present invention relates generally to genetically modified mice useful as models of human Alzheimer disease. In specific aspects, the present invention relates to genetically modified mice expressing human APOE4 and mouse Trem2 p.R47H and methods of use thereof.

BACKGROUND OF THE INVENTION

One of the major obstacles to developing therapies for Alzheimer's disease (AD) is the lack of animal models to be used in preclinical trials. One reason for this may be that existing models are based on familial mutations, while the vast majority of the clinical population has non-familial late-onset AD.

Familial or early-onset Alzheimer's disease is caused by mutations in, or overexpression of, the amyloid precursor protein (APP) gene or mutations in presently genes (PSEN1 or PSEN2), All of these lead to increased production of the Abeta42 peptide, which is thought to be neurotoxic. Dozens if not hundreds of mouse models that mimic aspects of familial Alzheimer's disease have been created. Many treatments have been shown to be effective in these familial Alzheimer's disease mouse models, but none have been effective when tested in clinical trials.

In contrast, late-onset Alzheimer's disease, which accounts for 95-98% of the human Alzheimer's disease patient population, does not have a simple and defined genetic etiology. Late-onset Alzheimer's disease is thought to be a multifactorial syndrome caused by a variety of genetic and environmental causes interacting with the aging process. Because of this complexity, the genetic causes are still not fully understood and no useful mouse models of late-onset Alzheimer's disease in humans have been reported to date.

SUMMARY OF THE INVENTION

A genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, and wherein the mouse expresses human APOE4p and mouse Trem2p. According to aspects of the present invention, the mouse is homozygous for the DNA sequence encoding APOE4p and for the DNA sequence encoding Trem2p.

A genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the APOE4p includes an amino acid sequence of: SEQ ID NO:1, or the APOE4p is encoded by the complement of a nucleic acid which hybridizes to SEQ ID NO:2 under highly stringent hybridization conditions. According to aspects of the present invention, the mouse is homozygous for the DNA sequence encoding APOE4p and for the DNA sequence encoding Trem2p.

A genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the mouse Trem2p includes an amino acid sequence of SEQ ID NO:3, or the mouse Trem2p is encoded by the complement of a nucleic acid which hybridizes to SEQ ID NO:4 under highly stringent hybridization conditions. According to aspects of the present invention, the mouse is homozygous for the DNA sequence encoding APOE4p and for the DNA sequence encoding Trem2p.

A genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, wherein the APOE4p includes an amino acid sequence of: SEQ NO:1, or the APOE4p is encoded by the complement of a nucleic acid which hybridizes to SEQ ID NO:2 under highly stringent hybridization conditions, and wherein the mouse Trem2p includes an amino acid sequence of: SEQ ID NO:3, or the mouse Trem2p is encoded by the complement of a nucleic acid which hybridizes to SEQ ID NO:4 under highly stringent hybridization conditions. According to aspects of the present invention, the mouse is homozygous for the DNA sequence encoding APOE4p and for the DNA sequence encoding Trem2p.

A genetically modified mouse characterized by one or more symptoms or signs associated with expression of human APOE4p and mouse Trem2p and relevant to non-familial late-onset Alzheimer's disease is provided according to aspects of the present invention wherein the genetically modified mouse is a B6(SJL)-Apoe$^{tm1.1(APOE*4)Adiuj}$ Trem2$^{em1Adiuj}$/J mouse whose genome includes: 1) a DNA sequence encoding human APOE4 protein (APOE4p), the DNA sequence encoding APOE4p operably linked to a promoter, and 2) a DNA sequence encoding mouse Trem2 protein having a mutation p.R47H (Trem2p), the DNA sequence encoding Trem2p operably linked to a promoter, wherein the mouse is homozygous for the DNA sequence encoding APOE4p and for the DNA sequence encoding Trem2p, and wherein the mouse expresses human APOE4p and mouse Trem2p.

A method for screening for a treatment for use in the treatment of Alzheimer's disease is provided according to aspects of the present invention, including administering a treatment to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.47H (Trem2p), the DNA sequence encoding Trem2p operably linked to a promoter, and wherein the mouse expresses human APOE4p and mouse Trem2p; and assessing an effect of the treatment on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the treatment includes comparing the effect of the treatment on the genetically modified mouse with a control. According to aspects of the present invention, the control includes administering the treatment to a mouse which does not express human APOE4p and mouse Trem2p and assessing an effect of the treatment on the mouse which does not express human APOE4p and mouse Trem2p. According to aspects of the present invention, the control includes administering the treatment to a wild-type C57BL6J mouse and assessing an effect of the treatment on the wild-type C57BL/6J mouse. According to aspects of the present invention, the control includes administering the treatment to an APOE3-expressing mouse and assessing an effect of the treatment on the APOE3-expressing mouse.

A method for screening for a treatment for use in the treatment of Alzheimer's disease is provided according to aspects of the present invention, including administering a treatment to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the APOE4p includes an amino acid sequence of: SEQ ID NO:1, or the APOE4p is encoded by the complement of a nucleic acid which hybridizes to SEQ ID NO:2 under highly stringent hybridization conditions; and assessing an effect of the treatment on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the treatment includes comparing the effect of the treatment on the genetically modified mouse with a control. According to aspects of the present invention, the control includes administering the treatment to a mouse which does not express human APOE4p and mouse Trem2p and assessing an effect of the treatment on the mouse which does not express human APOE4p and mouse Trem2p. According to aspects of the present invention, the control includes administering the treatment to a wild-type C57BL6J mouse and assessing an effect of the treatment on the wild-type C57BL/6J mouse. According to aspects of the present invention, the control includes administering the treatment to an APOE3-expressing mouse and assessing an effect of the treatment on the APOE3-expressing mouse.

A method for screening for a treatment for use in the treatment of Alzheimer's disease is provided according to aspects of the present invention, including administering a treatment to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the mouse Trem2p includes an amino acid sequence of: SEQ ID NO 3, or the mouse Trem2p is encoded by the complement of a nucleic acid which hybridizes to SEQ ID NO:4 under highly stringent hybridization conditions; and assessing an effect of the treatment on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the treatment includes comparing the effect of the treatment on the genetically modified mouse with a control. According, to aspects of the present invention, the control includes administering the treatment to a mouse which does not express human APOE4p and mouse Trem2p and assessing an effect of the treatment on the mouse which does not express human APOE4p and mouse Trem2p. According to aspects of the present invention, the control includes administering the treatment to a wild-type C57BL/6J mouse and assessing an effect of the treatment on the wild-type C57BL6J mouse. According to aspects of the present invention, the control includes administering the treatment to an APOE3-expressing mouse and assessing an effect of the treatment on the APOE3-expressing mouse.

A method for screening for a treatment for use in the treatment of Alzheimer's disease is provided according to aspects of the present invention, including administering a treatment to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, wherein the APOE4p includes an amino acid sequence of: SEQ ID NO:1, or the APOE4p is encoded by the complement of a nucleic acid which hybridizes to SEQ ID NO:2 under highly stringent hybridization conditions, and wherein the mouse. Trem2p includes an amino acid sequence of SEQ ID NO:3, or the mouse Trem2p is encoded by the complement of a nucleic acid which hybridizes to SEQ ID NO: 4 under highly stringent hybridization conditions; and assessing an effect of the treatment on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the treatment includes comparing the effect of the treatment on the genetically modified mouse with a control. According to aspects of the present invention, the control includes administering the treatment to a mouse which does not express human APOE4p and mouse Trem2p and assessing an effect of the treatment on the mouse which does not express human APOE4p and mouse Trem2p. According to aspects of the present invention, the control includes administering the treatment to a wild-type C57BL/6J mouse and assessing an effect of the treatment on the wild-type C57BL/6J mouse. According to aspects of the present invention, the control includes administering the treatment to an APOE3-expressing mouse and assessing an effect of the treatment on the APOE3-expressing mouse.

A method for screening for a treatment for use in the treatment of Alzheimer's disease is provided according to aspects of the present invention, including administering a treatment to a genetically modified mouse characterized by one or more symptoms or signs associated with expression of human APOE4p and mouse Trem2p and relevant to non-familial late-onset Alzheimer's disease is provided according to aspects of the present invention wherein the genetically modified mouse is a B6(SJL)-Apoe$^{tm1.1(APOE*4)Adiuj}$ Trem2$^{em1Adiuj}$/J mouse whose genome includes: 1) a DNA sequence encoding human APOE4 protein (APOE4p), the DNA sequence encoding APOE4p operably linked to a promoter; and 2) a DNA sequence encoding mouse Trem2 protein having a mutation p.R47H (Trem2p), the DNA sequence encoding Trem2p operably linked to a promoter, wherein the mouse is homozygous for the DNA sequence encoding APOE4p and for the DNA sequence encoding Trem2p, and wherein the mouse expresses human APOE4p and mouse Trem2p; and assessing an effect of the treatment on one or more symptoms or signs associated with expression of human APOE4p and mouse Trem2p relevant to non-familial late-onset. Alzheimer's disease on the mouse. According to aspects of the present invention, assessing an effect of the treatment includes comparing the effect of the treatment on the genetically modified mouse with a control. According to aspects of the present invention, the control includes administering the treatment to a mouse which does not express human APOE4p and mouse Trem2p and assessing an effect of the treatment on the mouse which does not express human. APOE4p and mouse Trem2p. According to aspects of the present invention, the control includes administering the treatment to a wild-type C57BL/6J mouse and assessing an effect of the treatment on the wild-type C57BL/6J mouse. According to aspects of the present invention, the control includes administering the treatment to an APOE3-expressing mouse and assessing an effect of the treatment on the APOE3-expressing mouse.

A method for screening for a compound for use in the treatment of Alzheimer's disease is provided according to aspects of the present in including administering a compound to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, and wherein the mouse expresses human APOE4p and mouse Trem2p; and assessing an effect of the compound on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the compound includes comparing the effect of the compound on the genetically modified mouse with a control. According to aspects of the present invention, the control includes administering the compound to a mouse which does not express human APOE4p and mouse Trem2p and assessing an effect of the compound on the mouse which does not express human APOE4p and mouse Trem2p. According to aspects of the present invention, the control includes administering the compound to a wild-type C57BL/6J mouse and assessing an effect of the compound on the wild-type C57BL/6J mouse. According to aspects of the present invention, the control includes administering the compound to an APOE3-expressing mouse and assessing an effect of the compound on the APOE3-expressing mouse.

A method for screening for a compound for use in the treatment of Alzheimer's disease is provided according to aspects of the present invention, including administering a compound to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the APOE4p includes an amino acid sequence of: SEQ ID NO:1, or the APOE4p is encoded by the complement of a nucleic acid which hybridizes to SEQ ID NO:2 under highly stringent hybridization conditions; and assessing an effect of the compound on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the compound includes comparing the effect of the compound on the genetically modified mouse with a control. According to aspects of the present invention, the control includes administering the compound to a mouse which does not express human APOE4p and mouse Trem2p and assessing an effect of the compound on the mouse which does not express human APOE4p and mouse Trem2p. According to aspects of the present invention, the control includes administering the compound to a wild-type C57BL/6J mouse and assessing an effect of the compound on the wild-type C57BL/6J mouse. According to aspects of the present invention, the control includes administering the compound to an APOE3-expressing mouse and assessing an effect of the compound on the APOE3-expressing mouse.

A method for screening for a compound for use in the treatment of Alzheimer's disease is provided according to aspects of the present invention, including administering a compound to a genetically modified mouse characterized by one or more symptoms or signs associated with expression of human APOE4p and mouse Trem2p and relevant to non-familial late-onset Alzheimer's disease is provided according to aspects of the present invention wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, and wherein the mouse Trem2p includes an amino acid sequence of: SEQ ID NO:3, or the mouse Trem2p is encoded by the complement of a nucleic acid which hybridizes to SEQ ID NO:4 under highly stringent hybridization conditions; and assessing an effect of the compound on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the compound includes comparing the effect of the compound on the genetically modified mouse with a control. According to aspects of the present invention, the control includes administering the compound to a mouse which does not express human APOE4p and mouse Trem2p and assessing an effect of the compound on the mouse which does not express human APOE4p and mouse Trem2p. According to aspects of the present invention, the control includes administering the compound to a wild-type C57BL/6J mouse and assessing an effect of the compound on the wild-type C57BL/6J mouse. According to aspects of the present invention, the control includes administering the compound to an APOE3-expressing mouse and assessing an effect of the compound on the APOE3-expressing mouse.

A method for screening for a compound for use in the treatment of Alzheimer's disease is provided according to aspects of the present invention, including administering a compound to a genetically modified mouse characterized by one or more symptoms or signs associated with expression of human APOE4p and mouse Trem2p and relevant to non-familial late-onset Alzheimer's disease is provided according to aspects of the present invention Wherein the genome of the mouse includes: 1) a DNA sequence encoding a human APOE4 protein (APOE4p), the DNA sequence encoding APOE4p operably linked to a promoter; and 2) a DNA sequence encoding a mouse Trem2 protein having a mutation p.R47H (Trem2p), the DNA sequence encoding Trem2p operably linked to a promoter, wherein the mouse expresses human APOE4p and mouse Trem2p, wherein the APOE4p includes an amino acid sequence of: SEQ ID NO:1, or the APOE4p: is encoded by the complement of a nucleic acid which hybridizes to SEQ ID NO:2 under highly stringent hybridization conditions, and wherein the mouse Trem2p includes an amino acid sequence of: SEQ ID NO:3, or the mouse Trem2p is encoded by the complement of a nucleic acid which hybridizes to SEQ ID NO:4 under highly stringent hybridization conditions; and assessing an effect of the compound on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the compound includes comparing the effect of the compound on the genetically modified mouse with a control. According to aspects of the present invention, the control includes administering the compound to a mouse which does not express human APOE4p and mouse Trem2p and assessing, an effect of the compound on the mouse which does not express human APOE4p and mouse Trem2p. According to aspects of the present invention, the control includes administering the compound to a wild-type C57BL/6J mouse and assessing an effect of the compound on the wild-type C57BL/6J mouse. According to aspects of the present invention, the control includes administering the compound to an APOE3-expressing mouse and assessing an effect of the compound on the APOE3-expressing mouse.

A method for screening for a compound for use in the treatment of Alzheimer's disease is provided according to aspects of the present invention, including administering a compound to a genetically modified mouse characterized by one or more symptoms or signs associated with expression of human APOE4p and mouse Trem2p and relevant to non-familial late-onset Alzheimer's disease is provided according to aspects of the present invention wherein the genetically modified mouse is a B6(SJL)-Apoe$^{tm1.1(APOE*4)Adiuj}$ Trem2$^{em1Adiuj}$/J mouse whose genome includes: 1) a DNA sequence encoding human APOE4 protein (APOE4p), the DNA sequence encoding APOE4p operably linked to a promoter; and 2) a DNA sequence encoding mouse Trem2 protein having a mutation p.R47H (Trem2p), the DNA sequence encoding Trem2p operably linked to a promoter, wherein the mouse is homozygous for the DNA sequence encoding APOE4p and for the DNA sequence encoding Trem2p, and wherein the mouse expresses human APOE4p and mouse Trem2p; and assessing an effect of the compound on one or more symptoms or signs associated with expression of human APOE4p and mouse Trem2p relevant to non-familial late-onset Alzheimer's disease on the mouse. According to aspects of the present invention, the mouse is homozygous for the DNA sequence encoding APOE4p and for the DNA sequence encoding Trem2p. According to aspects of the present invention, assessing an effect of the compound includes comparing the effect of the compound on the genetically modified mouse with a control. According to aspects of the present invention, the control includes administering the compound to a mouse which does not express human APOE4p and mouse Trem2p and assessing an effect of the compound on the mouse which does not express human APOE4p and mouse Trem2p. According to aspects of the present invention, the control includes administering the compound to a wild-type C57BL/6J mouse and assessing an effect of the compound on the wild-type C57BL/6J mouse. According to aspects of the present invention, the control includes administering the compound to an APOE3-expressing mouse and assessing an effect of the compound on the APOE3-expressing mouse.

DETAILED DESCRIPTION OF THE INVENTION

Figure 1:
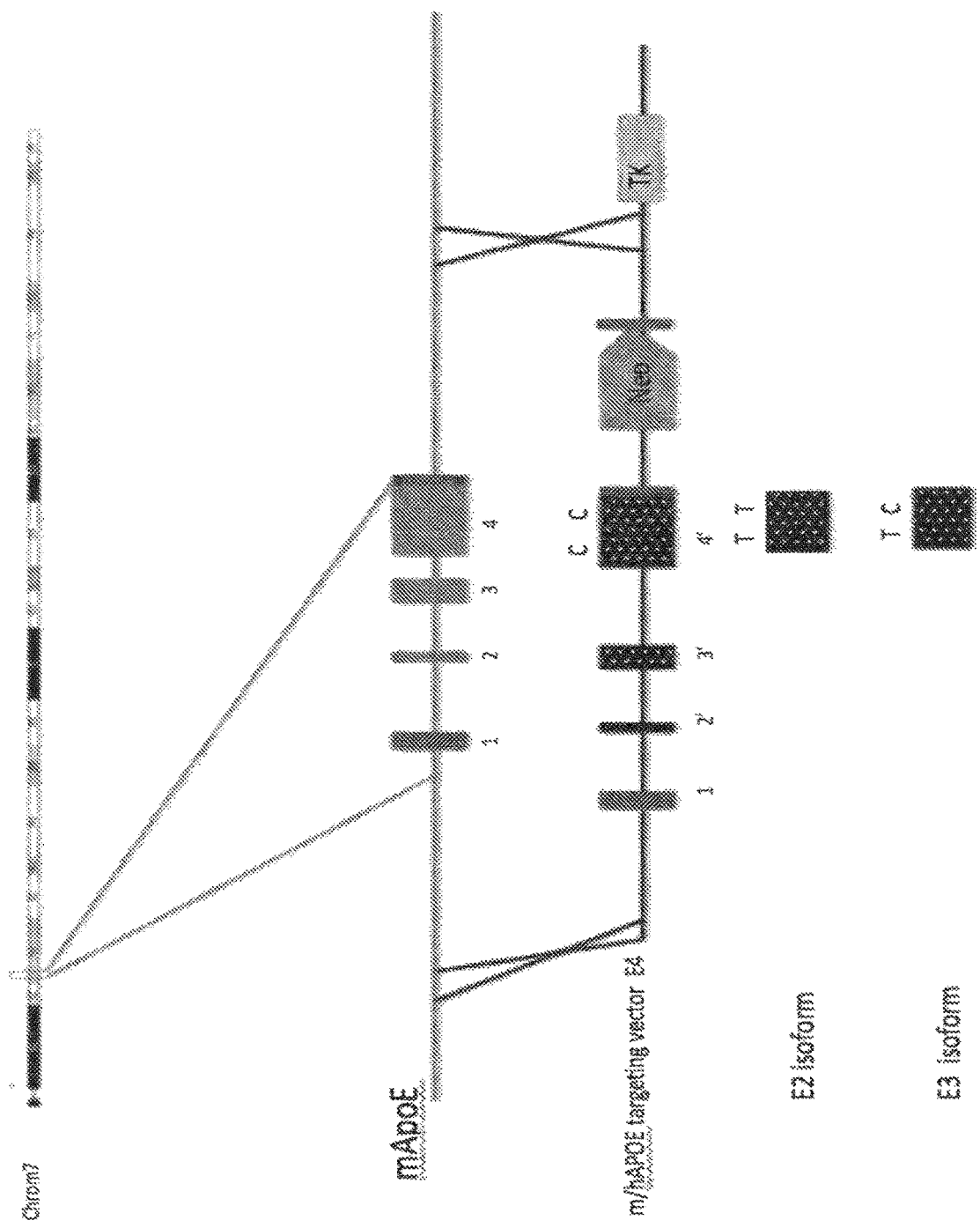
FIG. 1 is a schematic diagram of a humanized ApoE4 expression construct described in detail in examples herein.

The present invention relates generally to a genetically modified mouse which is a model of non-familial late-onset Alzheimer's disease and which encodes two exogenously introduced risk factors for non-familial late-onset AD in its genome, such that the mouse produces human apolipoprotein E4 (APOE4) and mouse Trem2 p.R47H proteins.

Human apolipoprotein is a polymorphic protein with three isoforms designated ApoE2, ApoE3 and ApoE4. These three isoforms differ from each other with respect to the identity of amino acids at positions 130 and 176 in the amino acid sequence of the proteins (corresponding to positions 112 and 158 in the mature APOE protein without the 18 amino acid signal peptide). ApoE2 is characterized by cysteine at both 130 and 176, ApoE3 is characterized by cysteine at 130 and arginine at 176 and ApoE4 is characterized by arginine at both 130 and 176. Individuals having one or more ApoE4 alleles are at greater risk for developing non-familial late-onset AD and a number of mechanisms relating to pathology have been proposed, see for example, DiBattista et al., 2016, Exp, Neurol. 280:97-105; Bu et al., Nature Reviews Neuroscience, 2009, 10:333-344; Huang et al., Cell, 2017, 168:1-15; and Tambini et al., EMBO Reports, 2016, 17:27-36.

Trem2 (triggering receptor expressed on myeloid cells 2) is an immune phagocytic receptor expressed by brain microglia. Trem2 triggers phagocytosis of cell debris and regulates aspects of the inflammatory response. A rare variant in TREM2, p.R47H, is significantly associated with Alzheimer's disease in humans.

In specific embodiments, the present invention relates to a genetically modified mouse whose genome includes a DNA sequence encoding human APOE4 protein and a DNA sequence encoding mouse Trem2 protein having the R47H point mutation.

A human APOE4 DNA sequence (hereinafter APOE4g) encoding human APOE4 protein (hereinafter APOE4p or "human APOE4") is shown herein as SEQ ID NO:2. An encoded APOE4p is shown herein as SEQ ID NO:1.

A mouse mutant Trem2 DNA sequence (hereinafter Trem2g) encoding mouse Trem2 protein having the R47H point mutation (hereinafter Trem2p or "mouse Trem2p") is shown herein as SEQ ID NO:4. An encoded Trem2p is shown herein as SEQ ID NO:3.

One or more genetic modifications can be introduced into a mouse genome to encode a variant of APOE4p and/or a variant of Trem2p in a genetically modified mouse according to embodiments of methods of the present invention.

As used herein, the term "variant" refers to APOE4p or Trem2p containing one or more mutations in its amino acid sequence compared to the corresponding protein of SEQ ID NO:1 or SEQ ID NO:3. For example, such mutations can be one or more amino acid substitutions, additions, and/or deletions, so long as the variant of APOE4p or Trem2p retains the functional characteristics of APOE4p or Trem2p of SEQ ID NO:1 or SEQ ID NO:3, respectively.

In particular embodiments, a variant APOE4p according to embodiments of the present invention has at least 90%, 91%, 92%, 93%, 94%, 95%, 96%, 97%, 98%, 99% or greater identity to SEQ ID NO:1 over its entire length, and has R (Arginine) and R (Arginine) as amino acids 130 and 176 of the APOE4 protein including an 18 amino acid signal peptide, shown herein as SEQ ID NO:1, as well as retains the functional characteristics of APOE4p of SEQ ID NO:1.

In particular embodiments, a variant APOE4p according to embodiments of the present invention has at least 90%, 91%, 92%, 93%, 94%, 95%, 96%, 97%, 98%, 99% or greater identity to SEQ ID NO:15 over its entire length, and has R (Arginine) and R (Arginine) as amino acids 112 and 158 of the APOE4 protein not including the 18 amino acid signal peptide, shown herein as SEQ ID NO:15, as well as retains the functional characteristics of APOE4p of SEQ NO:15.

In particular embodiments, a variant Trem2p according to embodiments of the present invention has at least 90%, 91%, 92%, 93%, 94%, 95%, 96%, 97%, 98%, 99% or greater identity to SEQ ID NO:3 over its entire length and retains the functional characteristics of Trem2p of SEQ ID NO:3.

Mutations can be introduced using standard molecular biology techniques, such as CRISPR technology. Alternative techniques include site-directed mutagenesis and PCR-mediated mutagenesis and the like. One of skill in the art will recognize that one or more amino acid mutations can be introduced without altering the functional properties of APOE4p and mouse Trem2p proteins.

Assays for assessment of functional properties of APOE4p, Trem2p and variants are known in the art.

Conservative amino acid substitutions can be made in APOE4p and Trem2p proteins to produce APOE4p and Trem2p variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

APOE4p and Trem2p variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

It will be appreciated by those of ordinary skill in the art that, due to the degenerate nature of the genetic code, nucleic acid sequences other than SEQ ID NO:2 and SEQ ID NO:4 encode APOE4p and Trem2p, respectively, and that such alternate nucleic acids may be introduced into a mouse genome to produce a genetically modified mouse expressing APOE4p and Trem2p of the disclosure.

The singular terms "a," "an," and "the" are not intended to be limiting and include plural referents unless explicitly stated otherwise or the context clearly indicates otherwise.

The terms "expressing" and "expresses" refer to transcription of a gene to produce a corresponding mRNA and/or translation of the mRNA to produce the corresponding protein.

APOE4p and Trem2p variants are encoded by nucleic acids having a high degree of identity with SEQ ID NO:2 or SEQ ID NO:4, respectively. The complement of a nucleic acid encoding an APOE4p variant specifically hybridizes with SEQ ID NO:2 encoding APOE4p under high stringency conditions. The complement of a nucleic acid encoding a Trem2p variant specifically hybridizes with SEQ ID NO:4 encoding Trem2p under high stringency conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art.

The term "stringency of hybridization conditions" refers to conditions of temperature, ionic strength, and composition of a hybridization medium with respect to particular common additives such as formamide and Denhardt's solution, Determination of particular hybridization conditions relating to a specified nucleic acid is routine and is well known in the art, for instance, as described in J. Sambrook and D. W. Russell, Molecular. Cloning: A Laboratory Manual, Cold Spring Harbor Laboratory Press; 3rd Ed., 2001; and Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarily are considered highly complementary and hybridize under high stringency conditions. Intermediate stringency conditions are exemplified by conditions under which nucleic acids having intermediate complementarily, about 50-84% complementarily, as well as those having a high degree of complementarily, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, et al., (Eds.), Short Protocols in Molecular Biology, Wiley, 2002.

An example of high stringency hybridization conditions is hybridization of nucleic acids over about 100 nucleotides in length in a solution containing 6×SSC, 5× Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-ACCT-3'. Further, the nucleotide sequence 3'-TCGA- is 100% complementary to a region of the nucleotide sequence 5'-TTAGCTGG-3'.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding, position in the second sequence, then the molecules are identical at that position. The percent identity between the two sequences is a function of the number of identical positions shared by the sequences (i.e., % identity-number of identical overlapping positions/total number of positions X100%). In one embodiment, the two sequences are the same length or differ in length by no more than 1%, 2%, 3%, 4%, 5%, 6%, 7%, 8%, 9% or 10% of the total length of the reference sequence.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI. BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller. 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps in calculating percent identity, typically only exact matches are counted.

Nucleic acids encoding APOE4p, Trem2p or a variant of either thereof can be isolated from natural sources, generated recombinantly or made by chemical synthetic techniques using well-known methodology.

Genetically Modified Mice

A genetically modified mouse is provided according to embodiments of the present invention whose genome includes a nucleic acid encoding APOE4p operably linked to a promoter, wherein the animal expresses the encoded APOE4p, and whose genome includes a nucleic acid encoding Trem2p operably linked to a promoter, wherein the animal expresses the encoded Trem2p.

A genetically modified mouse is provided according to embodiments of the present invention whose genome includes a nucleic acid encoding APOE4p operably linked to the endogenous mouse Apoe promoter, wherein the animal expresses the encoded APOE4p and whose genome includes a nucleic acid encoding Trem2p operably linked to the endogenous mouse Trem2 promoter, wherein the animal expresses the encoded Trem2p.

Any of various methods can be used to introduce a genetic modification into a mouse genome to produce a genetically modified mouse expressing APOE4p and Trem2p.

Genome editing methods for generating a genetically modified mouse according to embodiments of the present invention whose genome includes a nucleic acid encoding APOE4p operably linked to a promoter, wherein the animal expresses the encoded APOE4p and whose genome includes a nucleic acid encoding Trem2p operably linked to a promoter, wherein the animal expresses the encoded Trem2p, include, but are not limited to, site directed mutagenesis, recombination-based methods and nuclease genome editing techniques.

Genome editing techniques can be used to modify a genomic sequence by introduction of a discrete mutation at a predetermined target site in the genome.

For example, one or more nucleotides in a genomic sequence can be replaced with one or more different nucleotides using a genome editing technique so that the genomic sequence encodes a protein with a single amino acid difference, or multiple amino acid differences, compared to the unmodified genomic sequence.

Genome editing techniques can also be used to modify a genomic sequence by insertion of a coding sequence into the genome at a predetermined target site, a "knock-in" technique.

As used herein, the terms "target site" and "target sequence" in the general context of a genetic editing technique refer to a nucleic acid sequence that defines a portion of a chromosomal sequence to be edited.

For example, a nucleic acid sequence encoding a protein can be inserted at a predetermined target site in the genome so that the genome includes a nucleic acid encoding the protein and the protein is expressed. The nucleic acid sequence can also contain a promoter to drive expression of the encoded protein or expression of the encoded protein can be driven by an endogenous promoter when the nucleic acid is inserted in a position so that it is operably linked to the endogenous promoter.

According to particular aspects of the present invention, a point mutation is introduced into the genome of a first mouse using a genome editing technique so that the mouse encodes Trem2p, and a nucleic acid encoding human APOE4 is inserted into the Apoe4 gene in the genome of a second mouse by a "knock-in" genome editing technique so that the genome of the second mouse contains a "humanized" APOE4 gene as shown in FIG. 1, containing exon 1 of the mouse Apoe4 gene and exons 2, 3 and 4 of the human APOE4 gene. The first and second mice are then bred, naturally or by artificial methods, to obtain a genetically modified mouse whose genome includes a DNA sequence encoding APOE4p and a DNA sequence encoding Trem2p.

According to particular aspects of the present invention, a point mutation is introduced into the genome of a first mouse using CRISPR, genome editing technique so that the mouse encodes Trem2p, and a nucleic acid encoding human APOE4 is introduced into the Apoe4 gene in the genome of a second mouse by a "knock-in" CRISPR genome editing technique so that the genome of the second mouse contains a "humanized" APOE4 gene as shown in FIG. 1, containing exon 1 of the mouse Apoe4 gene and exons 2, 3 and 4 of the human APOE4 gene. The first and second mice are then bred naturally or by artificial methods to produce a genetically modified mouse whose genome includes a DNA sequence encoding APOE4p and a DNA sequence encoding Trem2p.

Genomic editing is performed, for example, by methods described herein, and as detailed in J. P. Sundberg and T. Ichiki, Eds., Genetically Engineered Mice Handbook, CRC Press; 2006; M. H. Hofker and J. van Deursen, Transgenic Mouse Methods and Protocols, Humana Press, 2002; A. L. Joyner, Gene Targeting: A Practical Approach, Oxford University Press, 2000, Manipulating the Mouse Embryo: A Laboratory Manual, $3^{rd}$ edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer a al., PNAS USA, 2010, vol. 107 (34), 15022-15026; and Doudna, J. et al, (eds.) CRISPR-Cas; A Laboratory Manual, 2016, CSHP. A brief description of several genomic editing techniques is described herein.

Nuclease Techniques for Genetic Modification of Mice

A genetic modification method, such as but not limited to, a nuclease genetic editing technique, can be used to introduce a desired DNA sequence into the genome at a predetermined target site, such as methods using a homing endonuclease, integrase, meganuclease, transposon, nuclease-mediated process using a zinc finger nuclease (ZFN), a Transcription Activator-Like (TAL), a Clustered Regularly interspaced Short Palindromic Repeats (CRISPR)-Cas, or Drosophila Recombination-Associated Protein (DRAP). Briefly, a genetic modification method that can be used includes introducing into an ES cell, iPS cell, somatic cell, fertilized oocyte or embryo, RNA molecules encoding a targeted TALEN, ZFN, CRISPR DRAP and at least one oligonucleotide, then selecting for an ES cell, iPS cell, somatic cell, fertilized oocyte or embryo with the desired genetic modification.

For example, a desired nucleic acid sequence can be introduced into the genome of a mouse at a predetermined target site by a nuclease technique, such as, but not limited to, CRISPR methodology, TAL (transcription activator-like) Effector methodology, Zinc Finger-Mediated Genome Editing or DRAP to produce a genetically modified mouse provided according to embodiments of the present invention whose genome includes a nucleic acid encoding APOE4p operably linked to a promoter, wherein the animal expresses the encoded. APOE4p and whose genome includes a nucleic acid encoding Trem2p operably linked to a promoter, wherein the animal expresses the encoded Trem2p.

As used herein, the terms "target site" and "target sequence" in the context of a nuclease genetic editing technique refer to a nucleic acid sequence that defines a portion of a chromosomal sequence to be edited and to which a nuclease is engineered to recognize and bind, provided sufficient conditions for binding exist.

CRISPR-Cas System

CRISPRs (Clustered Regularly Interspaced Short Palindromic Repeats) are loci containing multiple short direct repeats, that are found in the genomes of approximately 40% of sequenced bacteria and 90% of sequenced archaea and confer resistance to foreign DNA elements, see Horvath, 2010, Science, 327: 167-170; Barrangou et al, 2007, Science, 315: 1709-1712; and Makarova et al, 2011, Nature Reviews Microbiology. 9: 467-477, CRISPR repeats range in size from 24 to 48 base pairs. They usually show some dyad symmetry, implying the formation of a secondary structure such as a hairpin, but are not truly palindromic. CRISPR repeats are separated by spacers of similar length.

The CRISPR-associated (cas) genes are often associated with CRISPR repeat-spacer arrays. More than forty different Cas protein families have been described (Haft et al. 2005, PLoS Comput Biol. 1 (6): e60). Particular combinations of cas genes and repeat structures have been used to define 8 CRISPR subtypes, some of which are associated with an additional gene module encoding repeat-associated mysterious proteins (RAMPs).

There are diverse CRISPR systems in different organisms, and one of the simplest is the type II CRISPR system from *Streptococcus pyogenes*: only a single gene encoding the Cas9 protein and two RNAs, a mature CRISPR RNA (crRNA) and a partially complementary trans-acting RNA (tracrRNA), are necessary and sufficient for RNA-guided silencing of foreign DNAs (Gasiunas et al, 2012, PNAS 109: E2579-E2586; Jinek et al, 2012, Science 337: 816-821). Maturation of crRNA requires tracrRNA and RNase III (Deltcheva et al, 2011, Nature 471: 602-607). However, this requirement, can be bypassed by using an engineered small guide RNA (sgRNA) containing a designed hairpin that mimics the tracrRNA-crRNA complex (Jinek et al, 2012, Science 337: 816-821). Base pairing between the sgRNA and target DNA causes double-strand breaks (DSBs) due to the endonuclease activity of Cas9. Binding specificity is determined by both sgRNA-DNA base pairing and a short DNA motif (protospacer adjacent motif [PAM] sequence: NGG) juxtaposed to the DNA complementary region (Marraffini & Sontheimer, 2010, Nature Reviews Genetics, 11: 181-190). For example, the CRISPR system requires a minimal set of two molecules, the Cas9 protein and the sgRNA, and therefore can be used as a host-independent gene-targeting platform. The Cas9/CRISPR can be harnessed for site-selective RNA-guided genome editing, such as targeting insertion see for example, Carroll, 2012, Molecular Therapy 20: 1658-1660; Chang et al, 2013, Cell Research 23: 465-472; Cho et al, 2013, Nature Biotechnol 31: 230-232; Cong et al, 2013, Science 339: 819-823; Hwang et al, 2013, Nature Biotechnol 31: 227-229; Jiang et al, 2013, Nature Biotechnol 31; 233-239; Mali et al, 2013, Science 339: 823-826; Qi it al, 2013, Cell 152: 1173-1183; Shen et al, 2013, Cell Research 23: 720-723: and Wang et al, 2013, Cell 153: 910-918). In particular, Wang et al. 2013, Cell 153: 910-918 describe targeted insertion using the CRISPR/Cas9 system combined with oligonucleotides.

TAL (Transcription Activator-Like) Effectors

Transcription activator-like (TAL) effectors or TALE (transcription activator-like effector) are derived from a plant pathogenic bacteria genus, *Xanthomonas*, and these proteins mimic plant transcriptional activators and manipulate the plant transcript, see Kay et al., 2007, Science, 318:648-651.

TAL effectors contain a centralized domain of tandem repeats, each, repeat containing approximately 34 amino acids, which are key to the DNA binding specificity of these proteins. In addition, they contain a nuclear localization sequence and an acidic transcriptional activation domain, for a review see Schornack et al 2006, J. Plant Physiol., 163(3): 256-272; Scholze and Boch, 2011, Curr Opin Microbiol, 14:47-53.

Specificity of TAL effectors depends on the sequences found in the tandem repeats. The repeated sequence includes approximately 102 bp and the repeats, are typically 91-100% homologous with each other (Bonas et al, 1989, Mol Gen Genet 218: 127436). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence, see Moscou and Bogdanove 2009 Science 326: 1501: and Boch et al. 2009, Science 326:1509-1512. The two hypervariable residues are known as repeat variable diresidues (RVDs), whereby one RVD recognizes one nucleotide of DNA sequence and ensures that the DNA binding domain of each TAL-effector can target large recognition sites with high precision (15-30 nt). Experimentally, the code for DNA recognition of these TAL-effectors has been determined such that an sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a reporter gene in plant cells (Both et al. 2009, Science 326:1509-1512). These DNA binding domains have been shown to have general applicability in the field of targeted genomic editing or targeted gene regulation in all cell types, see Gaj et al., Trends an Biotechnol, 2013, 31(7):397-405. Moreover, engineered TAL effectors have been shown to function in association with exogenous functional protein effector domains such as a nuclease, not naturally found in natural *Xanthomonas* TAL-effect or proteins in mammalian cells. TAL nucleases (TALNs or TALENs) can be constructed by combining TALs with a nuclease, e.g. FokI nuclease domain at the N-terminus or C-terminus, Kim et al. 1996, PNAS 93; 1156-1160; Christian et al. 2010, Genetics 186:757-761; Li et al., 2011, Nucleic Acids Res 39: 6315-6325; and Miller et al, 2011, Nat Biotechnol 29: 143-148. The functionality of TALENs to cause deletions by NHEJ has been shown in rat, mouse, zebrafish, *Xenopus*, medaka, rat and human cells, Ansai et al., 2013, Genetics, 193: 739-749; Carlson et al., 2012, PNAS, 109: 17382-17387; Hockemeyer et al., 2011, Nature Biotechnol., 29: 731-734; Lei et al, 2012, PNAS, 109: 17484-17489; Moore et al., 2012, PLoS ONE, 7: e37877; Stroud et al., 2013, J. Biol. Chem., 288: 1685-1690; Sung et al, 2013, Nature Biotechnol 31: 23-24; Wefers et al., 2013, PNAS 110: 3782-3787.

For TALEN, methods of making such are further described in the U.S. Pat. Nos. 8,420,782, 8,450,471, 8,450, 107, 8,440,432 and 8,440,431, and US patent application publications 2013/0137161 and 2013/0137174.

Other useful endonucleases may include, for example, HhaI, HindIII, NotI, BbvCI, EcoRI, Bg/I, and AlwI. The fact that some endonucleases FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

In some embodiments, the TALEN may further include a nuclear localization signal or sequence (NLS). A NLS is an amino acid sequence that facilitates targeting the TALEN nuclease protein into the nucleus to introduce a double stranded break at the target sequence in the chromosome.

Nuclear localization signals are known in the art, see, for example, Makkerh et al. 1996, Curr Biol. 6; 1025-1027, NLS include the sequence PKKKRKV (SEQ ID NO: 16) from SV40 Large T-antigen, Kalderon 1984, Cell, 39: 499-509; RPAATKKAGQAKKK (SEQ ID NO:17) from nucleoplasmin, Dingwallet et al., 1988, J Cell Biol., 107, 841-9. Further examples are described in McLane and Corbett 2009, IUBMB Life, 61, 697-70; Dopie et al. 2012, PNAS, 109, E544-E552.

The cleavage domain may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res, 25:3379-3388. Additional enzymes that cleave DNA are known, e.g., SI Nuclease mung bean nuclease; pancreatic DNase I; micrococcal nuclease; yeast HO endonuclease. See also Linn et al. (eds.) Nucleases, Cold Spring Harbor Laboratory Press, 1993. One or more of these enzymes, or functional fragments thereof, may be used as a source of cleavage domains.

Zinc Finger-Mediated Genome Editing

The use of zinc finger nucleases (ZFN) for gene editing, such as for targeted insertion via a homology-directed repair process, has been well established. For example, see Carbery et al., 2010, Genetics, 186: 451-459; Cui et al., 2011, Nature Biotechnol 29: 64-68; Hauschild et al., 2011, PNAS, 108: 12013-12017; Orlando et al., 2010, Nucleic Acids Res., 38: e152-e152; and Porteus & Carroll, 2005, Nature Biotechnology, 23: 967-973.

Components of the ZFN-mediated process include a zinc finger nuclease with a DNA binding domain and a cleavage domain. Such are described for example in Beerli et al. (2002) Nature Biotechnol., 20:135-141; Pabo et al. (2001) Ann. Rev. Biochem., 70:313-340; Isalan et al. (2001) Nature Biotechnol. 19:656-660; Segal et al. (2001) Curr Opin, Biotechnol, 12:632-637; and Choo et al. (2000) Curr Opin, Struct. Biol., 10:411-416; and U.S. Pat. Nos. 6,453,242 and 6,534,261. Methods to design and select a zinc finger binding domain to a target sequence are known in the art, see for example Sera, et al., Biochemistry 2002, 41,7074-7081; U.S. Pat. Nos. 6,607,882; 6,534,261 and 6,453,242.

In some embodiments, the zinc finger nuclease may further include a nuclear localization signal or sequence (NLS), A NLS is an amino acid sequence that facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

The cleavage domain may be obtained from any endonuclease or exonuclease. Non-limiting examples of endonucleases from which a cleavage domain may be derived include, but are not limited to, restriction endonucleases and horning endonucleases. See, for example, 2002-2003 Catalog, New England Biolabs, Beverly, Mass.; and Belfort et al. (1997) Nucleic Acids Res. 25:3379-3388. Additional enzymes that cleave DNA are known (e.g., SI Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains. A cleavage domain also may be derived from an enzyme or portion thereof; as described above, that requires dimerization for cleavage activity.

Two zinc finger nucleases may be required for cleavage, as each nuclease includes a monomer of the active enzyme dimer. Alternatively, a single zinc finger nuclease may include both monomers to create an active enzyme dimer. Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) PNAS 89:4275-4279; Li et al. (1993) PNAS 90:2764-2768; Kim et al. (1994) PNAS 91:883-887; Kim et al. (1994) J. Biol. Chem, 269:31, 978-31, 982. Thus, a zinc finger nuclease may include the cleavage domain from at least one Type IIS restriction enzyme and one or more zinc finger binding domains, winch may or may not be engineered. Exemplary Type IIS restriction enzymes are described for example in international Publication WO 07/014275, the disclosure of Which is incorporated by reference herein in its entirety. Additional restriction enzymes also contain separable binding and cleavage domains, and these also are contemplated by the present disclosure. See, for example, Roberts et al (2003) Nucleic Acids Res. 31: 418-420. An exemplary Type IIS restriction enzyme, whose cleavage domain is separable from the binding domain, is FokI. This particular enzyme is active as a dimer (Bitinaite et al, 1998, PNAS 95: 10,570-10,575). Accordingly, for the purposes of the present disclosure, the portion of the FokI enzyme used in a zinc finger nuclease is considered a cleavage monomer. Thus, for targeted double stranded cleavage using a FokI cleavage domain, two zinc finger nucleases, each including a FokI cleavage monomer, may be used to reconstitute an active enzyme dimer. Alternatively, a single polypeptide molecule containing a zinc finger binding domain and two FokI cleavage monomers may also be used. In certain embodiments, the cleavage domain may include one or more engineered cleavage monomers that minimize or prevent homodimerization, as described, for example, in U.S. Patent Publication Nos. 2005/0064474, 2006/0188987, and 2008/0131962, each of which is incorporated by reference herein in its entirety. By way of non-limiting example, amino acid residues at positions 446, 447, 479, 483, 484, 486, 487, 490, 491, 496, 498, 499, 500, 531, 534, 537 and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499. Thus, in one embodiment, a mutation at amino acid position 490 replaces Glu (E) with Lys (K); a mutation at amino acid residue 538 replaces Ile (1) with Lys (K); a mutation at amino acid residue 486 replaces Gin (Q) with Glu (E); and a mutation at position 499 replaces Ile (1) with Lys (K). Specifically, the engineered cleavage monomers may be prepared by mutating positions 490 from E to K and 538 from I to K in one cleavage monomer to produce an engineered cleavage monomer designated "E490K:I538K" and by mutating positions 486 from Q to E and 499 from I to L in another cleavage monomer to produce an engineered cleavage monomer designated "Q486E:I499L." The above described engineered cleavage monomers are obligate heterodimer mutants in which aberrant cleavage is minimized or abolished. Engineered cleavage monomers may be prepared using a suitable method, for example, by site-directed mutagenesis of wild-type cleavage monomers (FokI) as described in U.S. Patent Publication No. 2005/0064474.

The zinc finger nuclease described above may be engineered to introduce a double stranded break at the targeted site of integration. The double stranded break may be at the targeted site of integration, or it may be up to 1, 2, 3, 4, 5, 10, 15, 20, 25, 30, 35, 40, 45, 50, 100 or 1000 nucleotides away from the site of integration. In some embodiments, the double stranded break may be up to 1, 2, 3, 4, 5, 10, 15, or 20 nucleotides away from the site of integration. In other embodiments, the double stranded break may be up to 10, 15, 20, 25, 30, 35, 40, 45 or 50 nucleotides away from the site of integration. In yet other embodiments, the double stranded break may be up to 50, 100 or 1000 nucleotides away from the site of integration.

The DRAP technology has been described in U.S. Pat. Nos. 6,53464:3, 6,858,710 and 6,830,910 and Watt et al., 2006.

Optionally, a nucleic acid sequence encoding a protein can be inserted at a random target site in the genome so that the genome includes a nucleic acid encoding the protein. Typically, for random insertion, the nucleic acid sequence also contains a promoter to drive expression of the inserted nucleic acid.

In a father option, a nucleic acid encoding the desired protein, APOE4p, Trem2p or both APOE4p and Trem2p, is inserted into a predetermined target site in the genome other than the Apoe4 gene or the Trem2 gene.

For example, a nucleic acid encoding the desired protein, APOE4p, Trem2p or both APOE4p and Trem2p, is inserted into a predetermined target site in the genome known to result in reliable expression, such as the Hprt or the Rosa26 locus.

According to aspects, for genomic editing at a predetermined target site, a targeting construct is made using recombinant DNA techniques and includes 5' and 3' sequences which are homologous to the targeted endogenous gene in the cell. The targeting construct further includes a selectable marker such as neomycin phosphotransferase, hygromycin or puromycin, a nucleic acid encoding the desired protein, APOE4p, Trem2p or both APOE4p and Trem2p, and optionally a polyadenylation signal. To insure correct transcription and translation of the nucleic acid encoding the desired protein, the nucleic acid encoding the desired protein is either in frame with the endogenous gene locus, or a splice acceptor site and internal ribosome entry site (IRES) sequences can be included.

Such a targeting construct is transfected into a desired cell type, such as but not limited to, stem cells and the cells are screened to detect the correct genomic editing event using PCR, Southern blot or sequencing analysis. Cells with the correct genomic editing event can be further analyzed for expression of the encoded protein by protein analysis, such as ELISA or Western blot analysis. If desired, the nucleic acid encoding, the selectable marker can be configured to be removed by treating the stem cells with a recombinase such as Cre recombinase or Flippase (Flp). After recombinase treatment, the cells are analyzed for the presence of the nucleic acid encoding the desired protein.

Cells with the correct genomic editing event are selected and injected into preimplantation embryos as described above, Chimeric males are selected for breeding. Offspring can be analyzed for transmission of the ES cell genome by coat color and genetic analysis, such as PCR, Southern blot or sequencing and can be tested for expression of the desired protein, such as by protein analysis (Western blot, ELISA) or other functional assays. Offspring expressing the correct proteins are intercrossed to create mice homozygous for the genetic modification(s).

Generation of a genetically modified mouse expressing APOE4p and Trem2p may include injection or transfection of appropriate nucleic acids, such as one or more one or more nucleic acids encoding a desired protein and/or one or more expression constructs, such as an expression construct encoding a protein or RNA (such as cas9 or a guide RNA for use in CRISPR), into a preimplantation embryo or stein cells, such as embryonic stem (ES) cells or induced pluripotent stem (iPS) cells.

The terms "expression construct" and "expression cassette" are used herein to refer to a double-stranded recombinant DNA molecule containing a desired nucleic acid coding sequence and containing one or more regulatory elements necessary or desirable for the expression of the operably linked coding sequence.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (pA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The term "operably linked" as used herein refers to a nucleic acid in functional relationship with a second nucleic acid.

A regulatory element is included in an expression cassette is a promoter in particular embodiments. Tire term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific, binding by RNA polymerase and other transcription factors. In specific embodiments, a promoter is generally positioned upstream of the nucleic acid sequence transcribed to produce the desired molecule, and provides a site for specific binding by RNA polymerase and other transcription factors. An included promoter can be a constitutive promoter or can provide inducible expression; and can provide ubiquitous, tissue-specific or cell-type specific expression.

Ubiquitous promoters that can be included in an expression construct include, but are not limited to, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and a CMV (cytomegalovirus) promoter.

These and other promoters are known in the art as exemplified in Abboud, S. L. et al, J. Histochem & Cytochem., 51(7):941-949, 2003; Schorpp et al., Nucl. Acids Res., 24(9):1787-1788, 1996 McBurney, M. W. et al., Devel. Dynamics, 200:278-293, 1994; and Majumder, M. et al., Blood, 87(8):3203-3211, 1996.

In addition to a promoter, one or more enhancer sequences may be included such as, but not limited to, cytomegalovirus (CMV) early enhancer element and an SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA and SCF-pA.

An expression construct may include sequences necessary for amplification in bacterial cells, such as a selection marker (e.g. kanamlycin or ampicillin resistance gene) and a replicon.

For methods of DNA injection of an expression construct into a preimplantation embryo, the expression construct is optionally linearized before injection into mouse preimplantation embryos. Preferably the expression construct is injected into fertilized oocytes. Fertilized oocytes are collected from superovulated females the day after mating (0.5 dpe) and injected with the expression construct. The injected oocytes are either cultured overnight or transferred directly into oviducts of 0.5-day p.c. pseudopregnant females.

Methods for superovulation, harvesting of oocytes, expression construct injection and embryo transfer are known in the art and described in Manipulating the Mouse Embryo: A Laboratory Manual, $3^{rd}$ edition, Cold Spring Harbor Laboratory Press; Dec. 15, 2002, ISBN-10: 0879695919.

Offspring can be tested for the presence of the desired mutation or inserted sequence by DNA analysis, such as PCR, Southern blot or sequencing. Mice which are carrying the desired mutation or inserted sequence can be tested for protein expression such as for example, by ELISA or Western blot analysis.

Alternatively, a nucleic acid or expression construct may be transfected into stem cells (ES cells or iPS cells) using well-known methods, such as electroporation, calcium-phosphate precipitation and lipofection. The cells are screened for the presence of the desired mutation or inserted sequence by DNA analysis, such as PER, Southern blot or sequencing. Cells with the desired mutation or inserted sequence by can be tested for functional expression by protein analysis, such as for example, by ELISA or Western blot analysis.

Mouse ES cells are grown in media optimized for the particular line. Typically ES media contains 15% fetal bovine serum (FBS) or synthetic or semi-synthetic equivalents, 2 mM glutamine, 1 mM Na pyruvate, 0.1 mM non-essential amino acids, 50 U/ml and streptomycin, 0.1 mM 2-mercaptoethanol and 1000 U/ml LIF (plus, for some cell lines chemical inhibitors of differentiation) in Dulbeccocs Modified Eagle Media (DMEM). A detailed description is known in the art (Tremml et al., 2008, Current Protocols in Stem Cell Biology, Chapter 1: Unit 1C.4. For review of inhibitors of ES cell differentiation, see Buehr, M., et al. (2003). Genesis of embryonic stem cells. Philosophical Transactions of the Royal Society B: Biological Sciences 358, 1397-1402.

Selected cells incorporating the desired mutation or inserted sequence can be injected into preimplantation embryos. For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators.

Alternatively, to blastocyst injection, stem cells can be injected into early stage embryos (e.g. 2-cell, 4-cell, pre-morula or morula). Injection may be assisted with a laser or piezo pulses drilled opening the zona pellucida. Approximately 9-10 selected stem cells (ES or iPS cells) are injected per blastocysts, or 8-cell stage embryo, 6-9 stem cells per 4-cell stage embryo, and about 6 stem cells, per 2-cell stage embryo. Following stem cell introduction, embryos are allowed to recover for a few hours at 37° C. in 5% $CO_2$, 5% $O_2$ in nitrogen or cultured overnight before transfer into pseudopregnant recipient females. In a further alternative to stem cell injection, stem cells cart be aggregated with morula stage embryos. All these methods are well established and can be used to produce stem cell chimeras. For a more detailed description see Manipulating the Mouse Embryo: A Laboratory Manual, $3^{rd}$ edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259; Method for making genetic modifications, U.S. Pat. Nos. 7,659,442, 7,294,754, and Kraus et al. 2010, Genesis 48, 394-399.

Pseudopregnant embryo recipients are prepared using methods known in the art. Briefly, fertile female mice between 6-8 weeks of age are mated with vasectomized or sterile, males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation. Chimeric males are selected for breeding. Offspring can be analyzed for transmission of the ES cell genome by coat color and genetic analysis, such as PCR, Southern blot or sequencing. Further the expression of the encoded protein(s) can be analyzed by protein analysis (Western blot, ELISA) or other functional assays.

A genetically modified mouse of the present invention may be heterozygous or homozygous for the genetic modification.

According to aspects of the present invention, a genetically modified mouse of the present invention may be heterozygous or homozygous for the "knock-in" humanized APOE4 modification wherein the mouse expresses APOE4p and also may be heterozygous or homozygous for the mutated genomic sequence encoding Trem2p wherein the mouse expresses Trem2p.

Homozygous genetically modified mice expressing APOE4p can be crossed with homozygous genetically modified mice expressing Trem2p to create a congenic strain homozygous for both modifications and expressing both APOE4p and Trem2p according to embodiments.

Genetically modified mice of the present invention, can be any of various strains.

A genetic modification can be introduced into the genome of an isolated mouse embryonic stem (ES) cell, a mouse induced pluripotent stem (iPS) cell, a mouse somatic cell, a fertilized mouse oocyte (zygote) or a mouse embryo in a knock-in strategy to produce a genetically modified mouse of the present invention.

Embodiments of the invention provide a genetically modified mouse that includes a desired genetic modification in all or substantially all of its cells, as well as a genetically modified mouse that includes a desired genetic modification in some, but not all its cells.

A genetically modified mouse according to aspects of the present, invention can include one or more additional genetic variants associated with increased risk of late-onset Alzheimer disease in humans.

Identification of Treatments and Compounds

Methods for screening for putative treatments for human Alzheimer's disease are provided according to embodiments of the present invention which include: administering a putative treatment for Alzheimer's disease to a genetically modified mouse, wherein the genome of the mouse includes: 1) a DNA sequence encoding human APOE4 protein (APOE4p) operably linked to a promoter; and 2) a DNA sequence encoding mouse Trem2 protein having a mutation p.R47H (Trem2p) operably linked to a promoter, wherein the mouse expresses APOE4p and Trem2p and wherein the mouse is characterized by one or more symptoms or signs associated with expression of APOE4p and Trem2p relevant to non-familial late-onset Alzheimer's disease of the present invention; and assessing an effect of the putative treatment on the mouse.

Methods for screening for putative treatments for human Alzheimer's disease are provided according to embodiments of the present invention which include: administering putative treatment for Alzheimer's disease to a B6(SJL)-$Apoe^{tm1.1(APOE*4)Adiuj}$ $Trem2^{em1/Adiuj}$/J mouse whose genome includes: 1) a DNA sequence encoding human APOE4 protein (APOE4p) operably linked to a promoter; and 2) a DNA sequence encoding mouse Trem2 protein having a mutation p.R47H (Trem2p) operably linked to a promoter, wherein the mouse is homozygous for the DNA sequence encoding APOE4p and for the DNA sequence encoding Trem2p, and wherein the mouse expresses human APOE4p and mouse Trem2p.; and assessing an effect of the putative treatment on the mouse.

Methods for screening for a compound for use in the treatment of Alzheimer's disease, are provided according to aspects of the present invention which include administering a compound to a genetically modified mouse of the present invention; and assessing an effect of the compound in the treatment of one or more symptoms or signs associated with expression of human APOE4p and mouse Trem2p relevant to non-familial late-onset Alzheimer's disease. Assessing an effect of the compound in the treatment of one or more symptoms or signs associated with expression of human APOE4p and mouse Trem2p relevant to non-familial late-onset Alzheimer's disease preferably includes comparing the result of the assessment with a suitable control, such as, but not limited to, the effect of the compound on a control, such as an APOE3-expressing mouse or a wild-type mouse (e.g. a mouse carrying the Apoe gene).

Such signs and symptoms include, but are not limited to, any one or more of: 1) presence of significantly more microglia in the brain of a genetically modified mouse of the present invention compared to a control, such as an APOE3-expressing mouse or wild-type control mouse; 2) presence of significantly more amyloid plaques in the brain of a genetically modified mouse of the present invention compared to a control, such as an APOE3-expressing mouse or wild-type control mouse; 3) presence of significantly more tau aggregates in the brain of a genetically modified mouse of the present invention compared to a control, such as an APOE3-expressing mouse or wild-type control mouse; 4)

presence of significantly more inflammation in the brain of a genetically modified mouse of the present invention compared to a control, such as an APOE3-expressing mouse or wild-type control mouse; 5) presence of significantly more synaptic and/or neuronal loss in the brain of a genetically modified mouse of the present invention compared to a control, such as an APOE3-expressing mouse or wild-type control mouse; 6) presence of significantly more cognitive deficit in the brain of a genetically modified mouse of the present invention compared to a control, such as an APOE3-expressing mouse or wild-type control mouse; 7) presence of significantly more indications of frailty an aging genetically modified mouse of the present invention compared to a control, such as an APOE3-expressing mouse or wild-type control mouse; 8) presence of significantly more blood flow deficit in the brain of a genetically modified mouse of the present invention compared to a control, such as an APOE3-expressing mouse or wild-type control mouse; 9) a significant difference in presence, level, and/or function of one or more biomarkers of non-familial late-onset Alzheimer's disease in blood, serum, or tissue of a genetically modified mouse of the present invention compared to a control, such as an APOE3-expressing mouse or wild-type control mouse; 10) cerebrovascular leakage in a genetically modified mouse of the present invention compared to a control, such as an APOE3-expressing mouse or wild-type control mouse; and 11) levels of one or more blood lipoproteins, such as high density lipoprotein, and low density lipoprotein, and/or cholesterol, in a genetically modified mouse of the present invention compared to a control, such as an APOE3-expressing mouse or Wild-type control mouse.

According to aspects of the present invention, methods for screening for putative treatments for human Alzheimer's disease are provided wherein assessing an effect of a compound includes comparing the effect of the compound on the genetically modified mouse, wherein the genome of the mouse includes: 1) a DNA sequence encoding human APOE4 protein (APOE4p) operably linked to a promoter; and 2) a DNA sequence encoding mouse Trem2 protein having a mutation p.R47H (Trem2p) operably linked to a promoter, wherein the mouse expresses APOE4p and Trem2p and wherein the mouse is characterized by one or more symptoms or signs associated with expression of APOE4p and Trem2p relevant to non-familial late-onset Alzheimer's disease of the present invention, with a control.

According to aspects of the present invention, methods for screening for putative treatments for human Alzheimer's disease are provided wherein assessing an effect of the compound includes comparing the effect of the compound on a B6(SJL)-Apoe$^{tm1.1(APOE*4)Adiuj}$ Trem2$^{em1Adiuj}$/J mouse with a control.

A suitable control includes, for example, administering the compound to a mouse which does not express human APOE4p and mouse Trem2p and assessing an effect of the compound on the mouse. A suitable control includes, for example, administering the compound to an APOE3-expressing mouse or wild-type control mouse. A wild-type control mouse can be any mouse which does not express human APOE4p and mouse Trem2p. A suitable control includes, for example, administering the compound to a wild-type C57BL/6J mouse; and assessing an effect of the compound on the wild-type C57BL/6J mouse.

Symptoms or signs associated with expression of human APOE4p and mouse Trem2p relevant to non-familial late-onset Alzheimer's disease can be assessed by methods well-known in the art including, but not limited to, immunoassay, nucleic acid assay, histochemical staining, cognitive assays, in vivo imaging, physical assessment of the animals, cerebrovascular leakage assessment, and morphological assessment of tissues and/or cells.

Immunoassays that can be used are well-known in the art and include, but are not limited to, enzyme-linked immunosorbent assay (ELISA) such as but not limited to, antigen capture ELISA, indirect ELISA, fixed cell ELBA; immunochromatography; antigen capture; flow cytometry; immunoblot; immunoprecipitation; immunodiffusion; competitive immunoassays, immunocytochemistry; radioimmunoassay; and combinations of any of these. Generalized details of immunoassays are described in standard references, illustratively including Wild, D., The Immunoassay Handbook, 3rd Ed., Elsevier Science, 2005; Gosling, J. P., Imunoassays: A Practical Approach, Practical Approach Series, Oxford University Press, 2005; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Ormerod, M. G., Flow Cytometry: a practical approach, Oxford University Press, 2000; and Givan, A. L., flow Cytometry: first principles, Wiley, New York, 2001.

According to aspects of the present invention, nucleic acid assays to detect a nucleic acid analyte relevant to non-familial late-onset Alzheimer's disease in a genetically modified mouse of the present invention compared to a wild-type mouse includes, but is not limited to, nucleic acid amplification techniques such as, but not limited to, PCR RT-PCR ligation-mediated PCR and phi-29 PCR; nucleic acid hybridization techniques such as, but not limited to, Northern blot, Southern blot, RNase protection assay, dot blot, transcriptome analysis, and in situ hybridization. Nucleic acid assays for both, qualitative and quantitative assay of a nucleic acid in a sample are described in detail in standard references, illustratively including J. Sambrook and D. W. Russell, Molecular Cloning: A Laboratory Manual, Cold Spring Harbor Laboratory Press; 3rd Ed., 2001; F. M. Ausubel et al., Eds., Short Protocols in Molecular Biology, Current Protocols, Wiley, 2002; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Biomarker assays that can be used are well-known in the art and include, but, are not limited to, assays of Aβ and tau species, neurofilaments, neurogranin, interleukins, TNFα, GM-CSF, and soluble Trem2 in cerebrospinal fluid (CSF), blood, serum, or tissue.

Cognitive assays that can be used are well-known in the art and include, but are not limited to, assays of spatial memory, short-term memory, long-term memory, assays of executive function, attentional tasks such as 3 and 5 choice serial reaction time tests, tests of processing speed, set shifting tests, reversal learning tasks, assays of object memory, assays of pattern recognition, assays of passive avoidance memory, assays of habituation, and assays of novel object recognition, water maze testing, fear conditioning tests, radial arm water maze testing, Y-maze testing, T-maze testing, and open field habituation tests.

Physical assessment methods of the animals that can be used are well-known in the art and include, but are not limited to, assessment of indices of frailty in a genetically modified mouse of the present invention compared to a control, such as an APOE3-expressing mouse or a wild-type mouse as a comparison to normal aging.

In vivo imaging methods that can be used are well-known in the art and include, but are not limited to, magnetic resonance imaging (MRI), computed tomography (CT) imaging, X-ray, optical imaging, and ultrasound imaging. Such imaging techniques can be used to assess one or more symptoms or signs associated with expression of human APOE4p and mouse Trem2p relevant to non-familial late-onset Alzheimer's disease including, but not limited to, amyloid or tau aggregation, abnormal blood flow pathological neuronal loss, and abnormal glucose metabolism.

Assessment of changes to one or more of: a transcriptomic profile, a proteomic profile, and a metabolic profile of a genetically modified mouse of the present invention compared to a wild-type mouse and or compared to clinical samples can be performed using methods that are well-known in the art.

Assessment of inflammation can be performed by assay of one or more biomarkers of inflammation, such as, but, not limited to, IL-8, IL-11, TNF-alpha, granulocyte-macrophage colony stimulating factor (GM-CSF), TGF-beta, VEGF, monocyte chemotactic factor-1, macrophage migratory inhibitory factor, s100B, fibrinogen, and interferon gamma-inducible protein 10. Such assays can be performed on samples obtained from a genetically modified mouse of the present invention and a wild-type mouse, such as a sample of brain, spinal cord, blood, plasma, serum, cerebrospinal fluid or other relevant tissue or body fluid.

Morphological assessment of tissues and/or cells can include physical examination of gross anatomy and/or microscopic examination of tissues and/or cells with or without histochemical or cytochemical staining of the tissues and/or cells. Morphological assessment of tissues and/or cells can include assessment of synaptic and neuronal loss.

A method for screening for a compound for use in the treatment of Alzheimer's disease in an individual human subject having or suspected of having Alzheimer's disease is provided according to aspects of the present invention which include administering a compound to a genetically modified mouse of the present invention; and assessing an effect of the compound on amyloid and/or tan which are associated with expression of human APOE4p and mouse Trem2p relevant to non-familial late-onset Alzheimer's disease on the mouse. According to particular embodiments, assessing an effect of the compound on amyloid and/or tan includes assessing the level and/or localization of amyloid and/or tau. According to particular embodiments, assessing an effect of the compound on amyloid and/or tau includes assessing amyloid and/or tau aggregates in a genetically modified mouse of the present invention, such as assessment of aggregate size, number, location or a combination of any two or more thereof.

Cerebrovascular leakage is a key aspect of non-familial late-onset Alzheimer's disease and it is a surprising and unexpected finding of the present invention that expression of human APOE4p and mouse Trem2p results in cerebrovascular leakage.

A method for screening for a compound for use in the treatment of non-familial late-onset Alzheimer's disease in an individual human subject having or suspected of having non-familial late-onset Alzheimer's disease is provided according to aspects of the present invention which include administering a compound to a genetically modified mouse of the present invention; and assessing an effect of the compound on cerebrovascular leakage which is associated with expression of human APOE4p and mouse Trem2p relevant to non-familial late-onset Alzheimer's disease in the mouse. Assessing an effect of the compound on cerebrovascular leakage includes, but is not limited to, assessment of cerebrovascular permeability. The term "cerebrovascular permeability" refers to the capacity of a blood vessel wall to allow for normal movement of small molecules or substances such as water, ions, certain drags and nutrients across the blood vessel wall while acting as a barrier to movement of larger molecules and substances, such as fibrinogen, and albumin. The term "cerebrovascular leakage" refers to an abnormality of blood vessels which results in leakage of larger molecules and substances, such as fibrinogen, and albumin, through blood vessel walls. Assays for assessing cerebrovascular leakage are well-known in the art, including in vitro assays using cells or tissues isolated from a genetically modified mouse of the present invention, and in vivo assays. A non-limiting example of an in vivo assay of cerebrovascular leakage includes intravenous injection of a labeled protein (e.g. Evans Blue-labeled albumin) and assessment of appearance of the dye-labeled protein in brain tissues, see for example, Radu et al., An in vivo Assay to Test Blood Vessel Permeability., J. Vis. Exp. 2013, (73):50062.

The putative treatment can be any treatment modality such as, but not limited to, administration of a compound. The term "compound" as used herein is not limited and encompasses small molecule chemicals and biologicals such as peptides, proteins, glycoproteins, including antibodies, for example.

Embodiments of inventive compositions and methods are illustrated in the following examples. These examples are provided for illustrative purposes and are not considered limitations on the scope of inventive compositions and methods.

EXAMPLES

Generation of a Genetically Modified Mouse having a DNA Sequence Encoding APOE4p in its Genome The mouse Apoe4 gene is located on chromosome 7 at 19,696,109-19,699,166. An APOE4 gene-targeting construct was made that included 4980 bp (SEQ ID NO:9) of mouse sequence, which defined the mouse 5' homology arm including exon 1 of mouse ApoE, 4292 bp (SEQ ID NO:10) of human APOE4 sequence including human protein coding exons 2-4 of the human gene as well as an additional 1.5 kb of flanking human sequence after the 3'UTR to include any potential regulatory sequences.

FIG. 1 shows a schematic diagram of the humanized ApoE4 construct (see "m/hAPOE targeting vector E4"). On FIG. 1, (C C) above exon 4' shows the nt present in exon 4 for arginine at p.R310 and R176, respectively, isoform E4. Isoform E2 with (T T) codes for cysteine at both C130 and C176, while E3 (T C) codes for cysteine at C130R and arginine at R176 sites.

Human APOE4 exon 4 contains sequence that codes for the ApoE4 isoform of the gene and encodes the nucleotide sequence for arginine at R130 and R176, It is noted that APOE4 includes an 18 amino acid signal peptide at the N-terminus of the protein such that APOE4 including the signal peptide is 317 amino acids and the variant amino acids which differ among APOE2, APOE3 and APOE4 are at positions 130 and 176. In the mature. APOE proteins (299 amino acids), the variant amino acids which differ among APOE2, APOE3 and APOE4 are at positions 112 and 158.

A Frt neo Frt selection cassette (FNF cassette, SEQ ID NO:11) was inserted after the human sequence followed by a NdeI restriction site (for ease of Southern screening). The FNF cassette is followed by 5166 bp of mouse sequence (SEQ ID NO 12), the 3' homology arm. The resulting 14,438 bp synthesized construct was cloned into pBlight vector using recombineering techniques, producing a construct called mApoE_hAPOE4_PGKneo_mAPOE for gene targeting in embryonic stem cells.

The ApoE4 gene-targeting construct was introduced into cultured embryonic stem (ES) cells of a C57Bl6 mouse strain by electroporation. Homologous recombination produced loci that retained all normal mouse regulatory sequences (plus non-coding exon one) together with the human APOE4 protein-encoding exons 2-4. Transfected ES cells were screened by Southern blot in ensure correct targeting. Three clones were identified that were correctly targeted. ES cells containing the correctly targeted locus were introduced into C57BL/6J embryos, and the resultant chimeric mice were bred with C57BL/6J mice. Offspring carrying the modified locus in the germ-line were interbred to generate the homozygous genetically modified genome. All F1 matings produced normal litter sizes with a Mendelian distribution of the locus.

Generation of a Genetically Modified Mouse having a DNA Sequence Encoding Trem3 in its Genome The Trem2 R47H KI allele was generated at The Jackson Laboratory by pronuclear injection of Cas9 RNA (100 ng) and a single guide sequence (50 ng) GAAGCACTGGGGGAGACGCA (SEQ ID NO:7) with 183 nt donor oligo (40 ng) (GCCCTCAACACCACGGTGCTGCAGGGCATGGCCGGCCAGTCCTTGAGGGTGTCA TGTACT-TATGACGCCTTGAAGCACTGGGGGA-GAC$\underline{A}$CAA$\underline{a}$GC$\underline{a}$TGGTGTCGGCAGC TGGGTGAGGAGGGCCCATGCCAGCGTGTGGT-GAGCACACACGGTGTGTGGCTGC TGGCCTTCCT-GAAGAAGCGG, SEQ ID NO:8) containing a nucleotide G>A point mutation (underlined, uppercase "A" at nt 89 in SEQ ID NO:8) for amino acid sequence change at R47H and 2 silent mutations (lysine AAG>AAA (underlined lower case "a" at nt 93 in SEQ ID NO:8) and alanine GCC>GCA (underlined lower case "a" at nt 96 in SEQ ID NO: 8)) into the gene (to prevent re-cutting of the donor sequence in homologous directed repair), The CRISPR strategy resulted in the specific R47H knock in, and silent mutations present in the Trem2 gene of founder mice.

Offspring carrying the modified allele in the germ-line were interbred to generate the homozygous genetically modified genome. All F1 matings produced normal litter sizes with a Mendelian distribution of the locus. The resulting inbred strain of mouse is designated C57BL/6J-Trem2$^{em1Adpme}$/J (common name Trem2 R47H KI (JAX)) and expresses Trem2p.

Generation of a Genetically Modified Mouse having a DNA Sequence Encoding APOE4p and a DNA Sequence Encoding Trem2p its Genome In this example, a genetically modified mouse was generated by crossing an inbred strain of mouse, B6(SJL)-Apoe$^{tm1.1(APOE*4)Adpme}$/J (common name APOE*4 KI (JAX)) expressing human APOE4p with an inbred strain of mouse, C57BL/61J-Trem2$^{em1Adpme}$/J (common name Trem2 R47H KI (JAX)) expressing mouse Trem2p. The resulting genetically modified mice, homozygous for both the humanized APOE4 allele and the R47H allele of the mouse Trem2 gene, are designated B6(SJL)-Apoe$^{tm1.1(APOE*4)Adiuj}$ Trem2$^{em1Adiuj}$/J (formerly B6(SJL)-Apoe$^{tm1.1(APOE*4)Adpme}$ Trem2$^{em1Adpme}$/J, abbreviated as APOE4 X Trem2 R47H (JAX) mice), common name: B6J.APOE4/Trem2, which express both human APOE4 and mouse Trem2p.

Validation of Genetically Modified Mouse Model of Non-Familial Late-Onset Alzheimer's Disease Tissue Harvesting, Protein Isolation and Sectioning Mice were administered a lethal dose of Ketamine/Xylazine by intraperitoneal injection, and transcardially perfused with 1×PBS (phosphate buffered saline). Brains were dissected, and the right hemisphere was snap frozen for protein isolation, while the left hemisphere was fixed in 4% paraformaldehyde overnight at 4° C. The fixed hemispheres were rinsed with 1×PBS, cryoprotected in 10% sucrose, followed by 30% sucrose at 4° C., and finally embedded in OCT (optimal cutting temperature compound). Frozen brains were sectioned at 25 μm and stored at −80° C. until required. Protein was extracted with Trizol Reagent (Life Technologies, Cat #15596-018) following manufacturer's guidelines. Protein pellets were resuspended in a solution of 1:1 8M urea and 1% SDS.

Immunofluorescence, Thioflavin S Staining and Image Capture

Cryosections were rinsed with PBT (1×PBS with 1% Triton-100) for 5 minutes (mins) then incubated with 500 μL of Liberate Antibody Binding Solution (L.A.B.-Polysciences Inc.) solution for 20 minutes at room temperature (RT) for antigen retrieval. Slides were then incubated overnight at 4° C. in the following primary antibodies: rabbit polyclonal anti-GFAP (1:200, Dako); rabbit polyclonal anti-IBA1 (1:250, Wako); rabbit polyclonal anti-NeuN (1:100, Cell Signaling Inc); mouse monoclonal anti-non-phosphorylated neurofilament (1:200, Covance) and sheep polyclonal anti-TREM2 (1:200, RD Systems). The sheep polyclonal anti-TREM2 antibody was previously verified using Trem2 deficient mice. All antibodies were diluted in PBTB (1×PBS, 1% TritonX-100 and 1% BSA) containing 10% normal goat or donkey serum. After primary incubation, sections were washed 3 times in PBT and incubated with appropriate secondary antibodies (goat anti-rabbit Alexa Fluor 488/594/633, goat anti-mouse Alexa Fluor 488, donkey anti-sheep Alexa Fluor 594, 1:1000 dilution, Life Technologies) for 2 hrs at RT.

All sections were then counterstained with DAPI and mounted with Aqua PolyMount (Polysciences). For Thioflavin S staining, sections stained with IBA1 and OFAP were further counterstained with 1% Thioflavin S (diluted in a 1:1 water:ethanol ratio). Slides were incubated for 8 mins at RT in 1% Thioflavin-S, washed in 80% ethanol, then 95% ethanol and finally in dH$_2$O and mounted, images were taken using either the Leica SP5 confocal microscope or the Zeiss Axio Imager.Z2. For each antibody, all images were captured using identical parameters for accurate quantification.

Initial observations were performed in sections from both males and females, Quantification of cell numbers was performed on brain sections from at least 4-6 male mice, as there was no overt difference between sexes. For plaque counts, the number of plaques present in the entorhinal cortical region for each mouse was determined. For IBA1+ cells, 5 equally spaced images were captured (using 20× optical lens) of either the cortex, in the region of the entorhinal cortex, or the hippocampus, from a central brain section of each mouse. For NeuN+ cells, 5 equally spaced images were captured (using 20× optical lens). For IBA1+ cells associated with plaques, images of 8+ plaques per brain were imaged (using 20× optical lens).

Images were processed and all cells in the 20× image were counted using the cell counter plugin for ImageJ/FIJI. A single cell was determined as a DAPI stained nucleus associated with a cell specific antibody stain (e.g. IBA1 or NEUN). Cell numbers in the 5 images from each mouse were totaled and then averaged across mice. Mouse number and diet were masked to the investigator for all cell counting assays.

Western Blot Analysis Demonstrates Expression of Human APOE4 in B6(SJL)-Apoe$^{tm1.1(APOE*4)Adiuj}$ Trem2$^{em1Adiuj}$/J (Common Name: B6J.APOE4/Trem2) Mice Brain extracts (~25 micrograms protein) were diluted in 2× Laemmli sample buffer (Bio-Rad 1610737) and run on a 4-20% gradient (BioRad mini-protean TGX 456-1096) and transferred to a nitrocellulose membrane (InVitrogen IB301001).

Blots were blocked with 5% non-fat milk powder and probed overnight at +4° C. with a human APOE4-specific antibody (Novus Biologicals NBP1-49529) at 1:100 dilution. Blots were then probed with secondary antibody (Millipore goat anti-mouse HRP AP191P) at 1:30,000 dilution for 2 hours at room temperature. Blots were detected using ECL chemiluminescent reagents (GE Healthcare RPN 2109) on Amersham Hyperfilm ECL (GE Healthcare 28906838).

Figure 2:
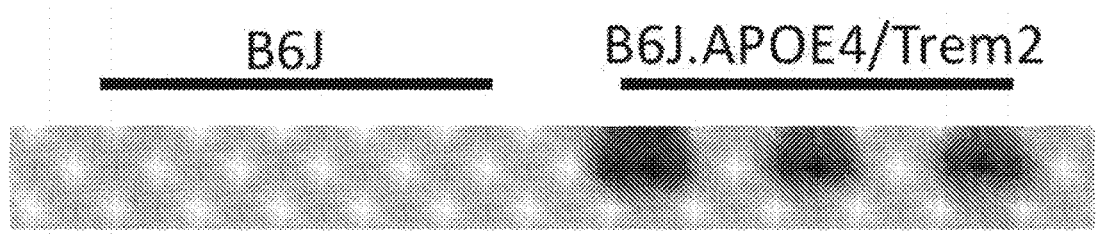
FIG. 2 is an image of a Western blot of brain tissue from B6(SJL)-Apoe$^{tm1.1(APOE*4)Adiuj}$ Trem2$^{em1Adiuj}$/J (common name: B6J.APOE4/Trem2) mice (lanes 4-6) and control (wild-type (WT) C57BL/6J (abbreviated B6J) mice (lanes 1-3) brain tissue.

An antibody that is specific for the human APOE4 variant (Novus Biologicals NBP1-49529 at 1:100 dilution) was used to probe Western blots of about 25 micrograms of protein from C57BL/6J (abbreviated B6J) or B6J.APOE4/Trem2 brain tissue. FIG. 2 is an image of a Western blot of brain tissue from B6J.APOE4/Trem2 (lanes 4-6) and control (WT (B6J); lanes 1-3) brain tissue. As shown in FIG. 2, human APOE4 protein expression was detected only in the protein from B6J.APOE4/Trem2 mice.

Blood Chemistry Shows Altered Metabolism in the B6J.APOE4/Trem2 Mice

APOE variants have been shown to differentially regulate lipoprotein and cholesterol metabolism. Although the mechanisms by which the APOE4 variant increases the risk for Alzheimer's disease is not known, these effects on altered metabolism are thought to play a role, Blood samples obtained from 12 month old B6J.APOE4/Trem2 (abbreviated APOE4/Trem2 in FIGS. 3A, 3B and 3C) mice and 12 month old C57BL/6J control mice were assayed for high density lipoprotein (HDL), low density lipoprotein (LDL) and total cholesterol according to standard blood chemistry methods.

Blood, extracted at harvest, was stored in EDTA coated vials on ice and further centrifuged at 5000 RPM for 15 mins. The plasma was removed and aliquoted for long term storage at −80° C. Plasma aliquots were profiled for the following: Total cholesterol (mg/dL), LDL (mg/dL), HDL (mg/dL)). High density lipoprotein cholesterol (HDL) was assayed using the Wako L-Type HDL-C kit (Wako 99100101) as per manufacturer's instructions. LDL was assayed using Beckman Coulter LDL-Cholesterol kit (Beckman Coulter OSR6196) as per manufacturer's instructions, Total cholesterol was assayed using the Beckman Coulter Cholesterol kit (Beckman Coulter OSR6116).

Figure 3A:
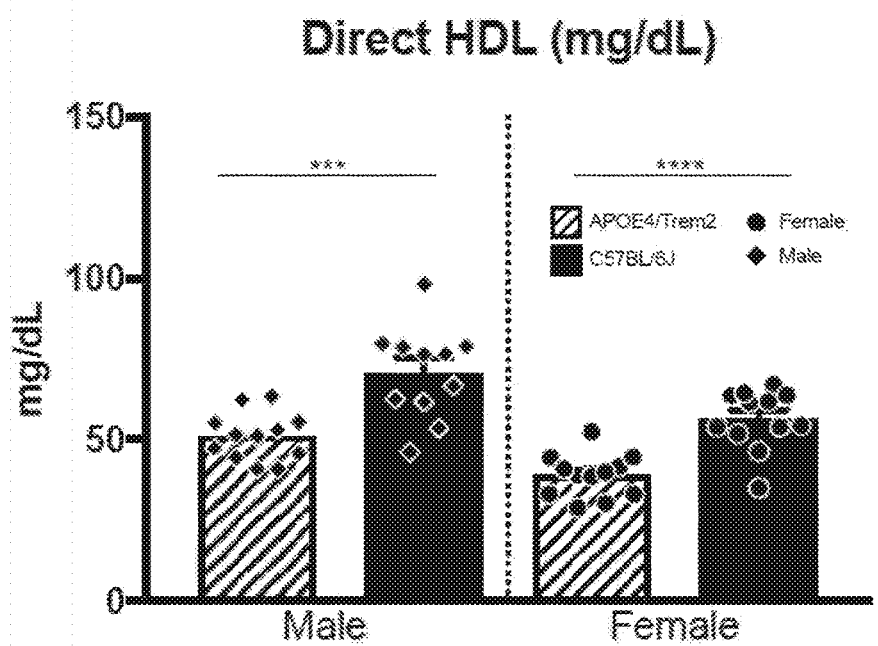
FIG. 3A is a graph showing results of an assay for high density lipoprotein (HDL) in blood samples obtained from 12 month old B6J.APOE4/Trem2 mice and 12 month old C57BL/6J control mice.
Figure 3B:
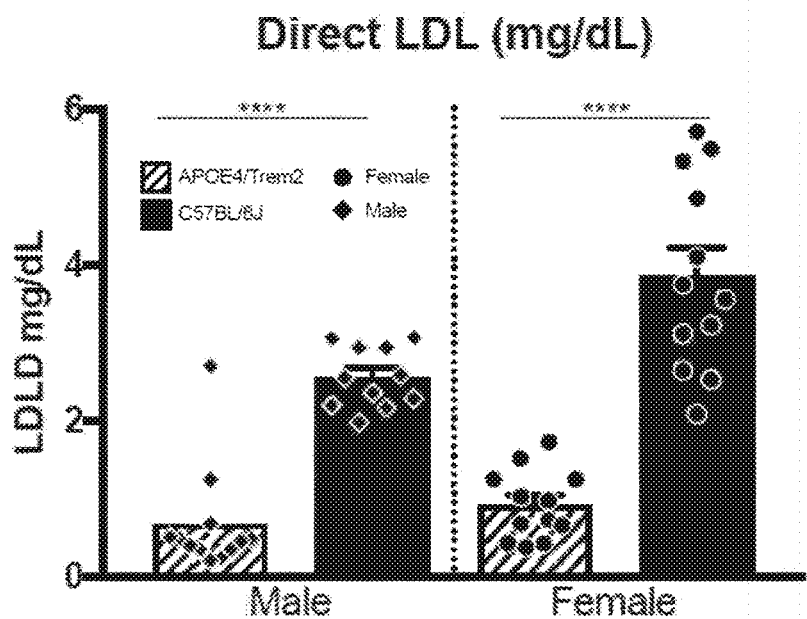
FIG. 3B is a graph showing results of an assay for low density lipoprotein (LDL) in blood samples obtained from 12 month old B6J.APOE4/Trem2 mice and 12 month old C57BL/6J control mice.
Figure 3C:
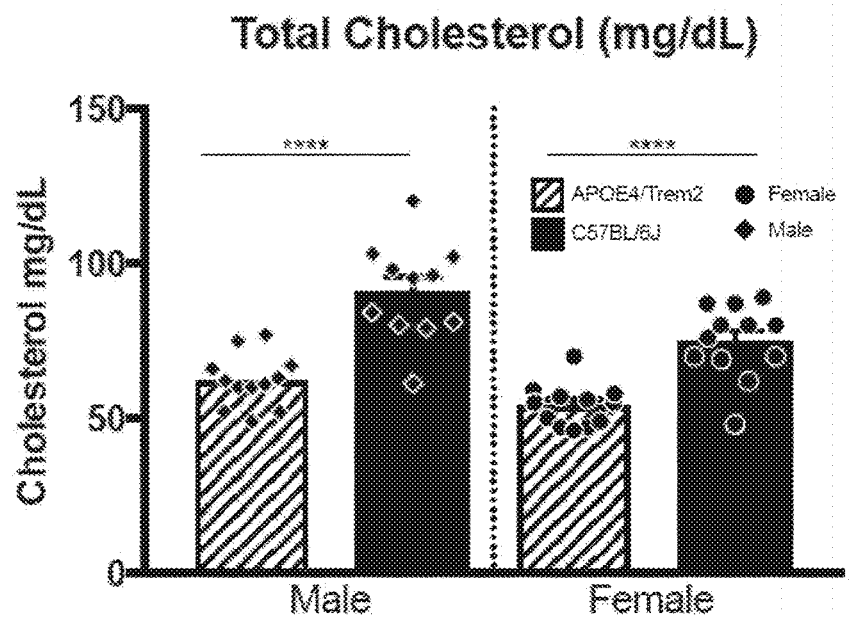
FIG. 3C is a graph showing results of an assay for total cholesterol in blood samples obtained from 12 month old B6J.APOE4/Trem2 mice and 12 month old C57BL/6J control mice.

Results are shown in FIGS. 3A, 3B, and 3C, respectively. These data show that the B6J.APOE4/Trem2 mouse has APOE4-dependent alterations in cholesterol metabolism, including reduced total cholesterol and reduced levels of both LDL and HDL.

Immunohistochemistry Shows Cerebrovascular Leakage and Inflammation in the B6J.APOE4/Trem2 Mice All mice were bred and housed in a 12/12 hours light/dark cycle. Eight month old mice were injected intraperitoneally with a lethal quantity of ketamine/xylazine according to IACUC approved procedures. Mice were perfused with 1×PBS (phosphate buffered saline) and whole brains were removed. One hemisphere was fixed in 4% paraformaldehyde overnight at +4° C. Following fixation, the tissue was rinsed in 1×PBS, incubated in 10% sucrose overnight at +4° C., then incubated in 30% sucrose overnight at 4° C. Brains were then frozen in optimal cutting temperature (OCT) compound and stored at −80° C. until sectioned. Frozen brains were sectioned at 25 microns and mounted on glass slides, and stored at −80° C. until required for immunofluorescence staining.

Slides were dried and post fixed in 4% PFA. Sections were subsequently immersed in diH$_2$O for 3 mins at 37° C., then transferred and incubated in 0.5 mg/mL pepsin in 0.2N HCl for 15 mins at 37° C. Sections were further washed in diH$_2$O for 3 mins, transferred to a humidified chamber, and washed in 1×PBS. Sections were incubated overnight in Rabbit anti-fibrin (1:200) and Goat anti-ColIV (anti-collagen IV) (1:40) at +4° C. in 1×PBT. Slides were washed in 1×PBT and incubated in the appropriate secondary antibodies at a concentration of 1:1000 (Donkey anti-rabbit IgG 594, Donkey anti-goat 488 for 2 hours at room temperature. Tissue was counterstained with DAPI and mounted using Aqua-Poly mount (Polyscience Inc). Staining was imaged on the Zeiss AxioImager at a magnification of 20×.

Figure 4:
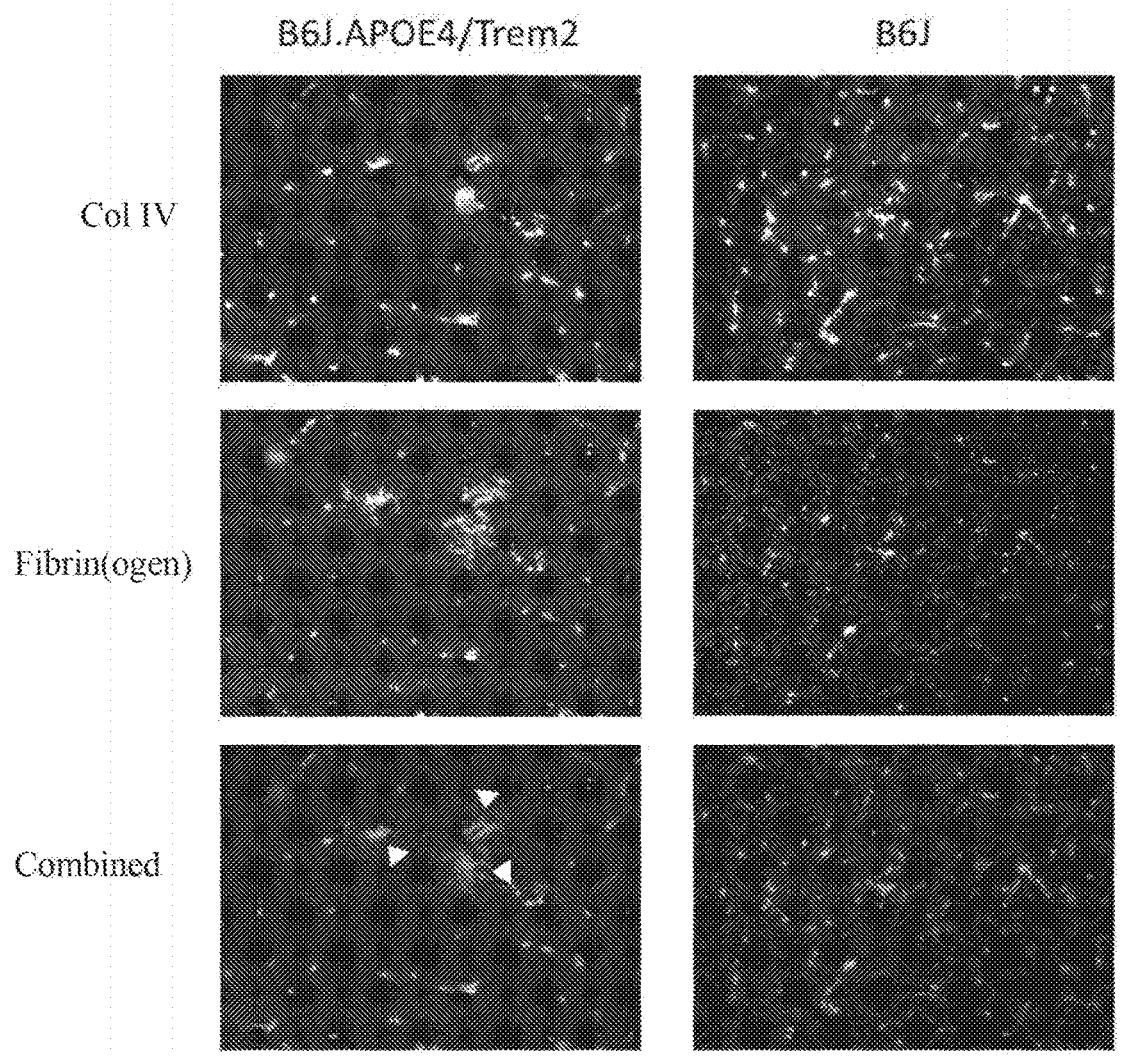
FIG. 4 shows representative images of B6J.APOE4/Trem2 tissue at 7-8 months of age immunostained to show Collagen IV (Col IV) and Fibrin(ogen) along with representative images from similar sagittal sections of brain from control C57BL/6J (abbreviated B6J) mice which were similarly immunostained.

Sagittal brain sections of B6J.APOE4/Trem2 mice were immunostained for fibrinogen (fibrin) to detect cerebrovascular leakage. Representative images of B6J.APOE4/Trem2 tissue at 7-8 months of age are shown in FIG. 4 along with representative images from similar sagittal sections of brain from control C57BL/6J (abbreviated B6J) mice. Arrows indicate cerebrovascular leakage as indicated by fibrin immunostaining outside of blood vessels. Blood vessels are shown by immunostaining for collagen IV (Col IV).

Vascular damage may be a key aspect of late-onset Alzheimer's disease pathology. Some existing mouse models of familial Alzheimer's disease have demonstrated cerebral amyloid angiopathy (CAA), but B6J.APOE4/Trem2 mice are the first model that does not over-express familial Alzheimer's disease mutations to show vascular deficits.

Transcriptional Analysis Demonstrates AD-Relevant Changes in Gene Expression in the B6J.APOE4/Trem2 Model Gene expression analysis was carried out with the NanoString Neuropathology gene panel. This assay measures the expression of 770 neuropathology-related genes. Female mice around eight months of age were assayed for the B6J.APOE4/Trem2 strain and the C57BL/6J (abbreviated B6J) strain, with three biological replicates of each strain.

Total RNA was extracted from brain homogenates. Tissues were lysed and homogenized in TRIzol Reagent (Ambion), then RNA was isolated using the miRNeasy kit (Qiagen), according to manufacturers' protocols, including the optional DNase digest step. Sample concentration and quality were assessed using the Nanodrop 2000 spectrophotometer (Thermo Scientific) and the RNA 6000 Nano LabChip assay (Agilent Technologies).

RNA was hybridized and multiplexed with NanoString probes according to manufacturer's instructions. Counts for target genes were normalized to housekeeping genes to account for variability in RNA content. Data were analyzed using Nanostring nSolver Analysis Software.

Figure 5:
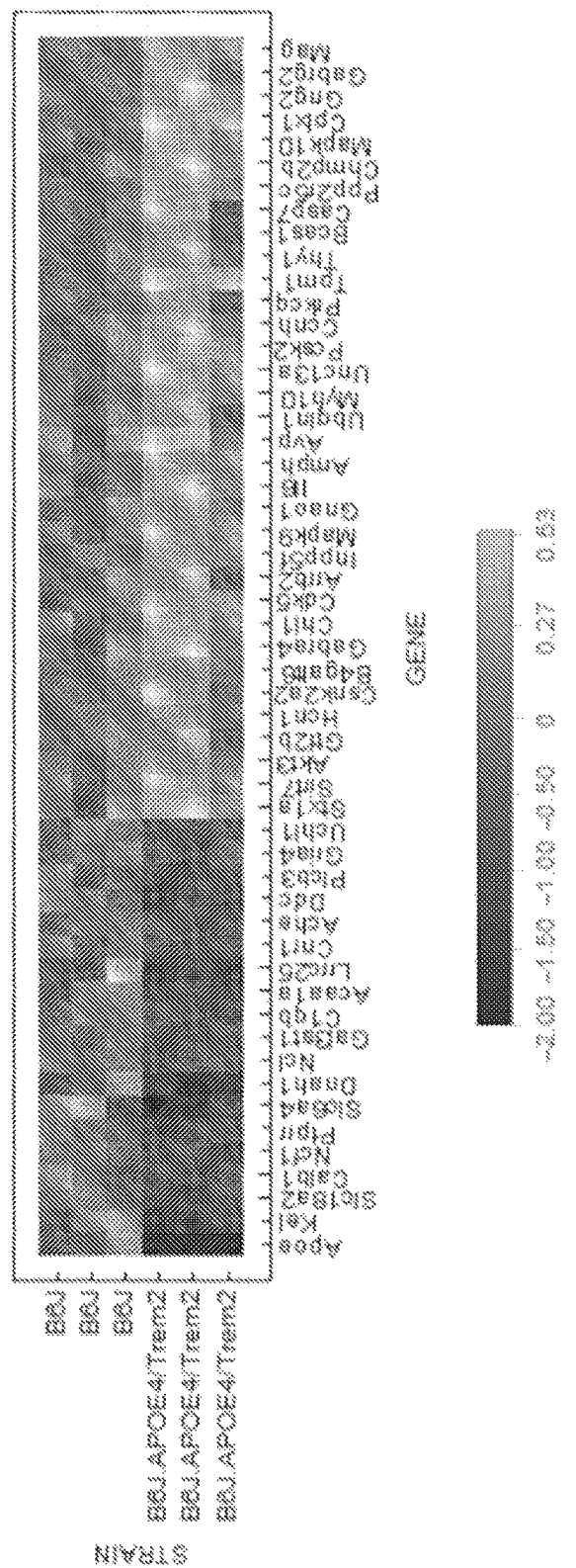
FIG. 5 is a gene expression heatmap of differentially-expressed genes is B6J.APOE4/Trem2 mice compared to wild-type control B6J mice.

Expression of each gene in the B6J.APOE4/Trem2 strain was compared to the control C57BL/6J strain and genes with significant (p<0.05) expression were identified with a linear regression model as shown in FIG. 5. FIG. 5 is a gene expression heatmap of differentially-expressed genes in B6J.APOE4/Trem2 compared to C57BL/6J. Expression values are in Log 2 fold change relative to the C57BL/6J average of each gene.

The probe used in this panel detects mouse Apoe but not human APOE. Because in this model mouse Apoe has been replaced by the human APOE4 variant, no Apoe expression is detected and this is shown as the most strongly down-regulated transcript.

The list of differentially-expressed genes contains multiple genes related to brain function and neurodegeneration. The Gene Ontology Biological Process and Panther Pathway annotations database was queued to identify processes and pathways represented by these genes. The relevant processes include, but are not limited to, the results in Table I which shows pathways and processes represented by the differentially-expressed genes in the B6J.APOE4/Trem2 strain. Notably, these interlinked processes and pathways include many highly relevant to neurodegeneration.

TABLE I

| Process or Pathway | Genes |
|---|---|
| Alzheimer's disease-amyloid secretase pathway | Pcsk2, Mapk10, Mapk9, Prkcq |
| 5HT2 type receptor mediated signaling pathway | Slc18a2, Plcb2, Slc6a4, Gng2, Prkcq |
| Inflammation mediated by chemokine and cytokine signaling pathway | Akt3, Gnao1, Plcb3, Arrb2, Il6, Myh10, Gng2 |
| Modulation of chemical synaptic transmission | Cnr1, Stx1a, Arrb2, Unc13a, Cdk5, Calb1, Slc6a4, Gria4 |
| Neuron development | Cnr1, Thy1, Mapk10, Hcn1, Cdk5, Chl1, Il6, Mapk9, Myh10, Uchl1 |
| Cognition | Cnr1, Amph, Cdk5, Calb1, Chl1, Slc6a4, Chmp2b |
| Apoptosis signaling | Akt3, Mapk10, Mapk9, Casp7, Prkcq |
| Aging | Cnr1, Slc18a2, Gnao1 |

Scientific and technical terms used herein are intended to have the meanings commonly understood by those of ordinary skill in the art. Such terms are found defined and used in context in various standard references illustratively including J. Sambrook and D. W. Russell, Molecular Cloning A Laboratory Manual, C. Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Herdewijn, P. (Ed.), Oligonucleotide Synthesis: Methods and Applications, Methods in Molecular Biology, Humana Press, 2004; A. Nagy, M. Gertsenstein, K. Vintersten, Behringer (Eds) 2002, Manipulating the Mouse Embryo: A Laboratory Manual, $3^{rd}$ edition, Cold Spring Harbor Laboratory Press, ISBN-10; 0879695919; and K. Turksen (Ed), Embryonic stein cells: methods and protocols in Methods in Molecular Biology, 2002; 185, Humana Press; Current Protocols in Stem Cell Biology, ISBN; 9780470151808.

Sequences

The amino acid sequence of APOE4p is shown along with exemplary nucleic acid sequences encoding APOE4p.

```
SEQ ID NO: 1: APOE4p (317 amino acids)
MKVLWAALLVTFLAGCQAKVEQAVETEPEPELRQQTEWQSGQRWELALGRFWDY

LRWVQTLSEQVQEELLSSQVTQELRALMDETMKELKAYKSELEEQLTPVAEETRAR

LSKELQAAQARLGADMEDVRGRLVQYRGEVQAMLGQSTEELRVRLASHLRKLRKR

LERDADDLQKRLAVYQAGAREGAERGLSAIRERLGPLVEQGRVRAATVGSLAGQPL

QERAQAWGERLRARMEEMGSRTRDRLDEVKEQVAEVRAKLEEQAQQIRLQAEAFQ

ARLKSWFEPLVEDMQRQWAGLVEKVQAAVGTSAAPVPSDNH

SEQ ID NO: 2: Exons 2, 3 and 4 of the human APOE4 genomic DNA sequence
encoding human APOE4p including the 18 amino acid signal peptide
ACTGGCCAATCACAGGCAGGAAGATGAAGGTTCTGTGGGCTGCGTTGCTGGTCA

CATTCCTGGCAGGTATGGGGGCGGGGCTTGCTCGGTTCCCCCCGCTCCTCCCCCT

CTCATCCTCACCTCAACCTCCTGGCCCCATTCAGGCAGACCCTGGGCCCCCTCTTC

TGAGGCTTCTGTGCTGCTTCCTGGCTCTGAACAGCGATTTGACGCTCTCTGGGCCT

CGGTTTCCCCCATCCTTGAGATAGGAGTTAGAAGTTGTTTTGTTGTTGTTGTTTGT

TGTTGTTGTTTTGTTTTTTTGAGATGAAGTCTCGCTCTGTCGCCCAGGCTGGAGTG

CAGTGGCGGGATCTCGGCTCACTGCAAGCTCCGCCTCCCAGGTCCACGCCATTCT
```

-continued

```
CCTGCCTCAGCCTCCCAAGTAGCTGGGACTACAGGCACATGCCACCACACCCGA

CTAACTTTTTTGTATTTTCAGTAGAGACGGGGTTTCACCATGTTGGCCAGGCTGGT

CTGGAACTCCTGACCTCAGGTGATCTGCCCGTTTCGATCTCCCAAAGTGCTGGGA

TTACAGGCGTGAGCCACCGCACCTGGCTGGGAGTTAGAGGTTTCTAATGCATTGC

AGGCAGATAGTGAATACCAGACACGGGGCAGCTGTGATCTTTATTCTCCATCACC

CCCACACAGCCCTGCCTGGGGCACACAAGGACACTCAATACATGCTTTTCCGCTG

GGCGCGGTGGCTCACCCCTGTAATCCCAGCACTTTGGGAGGCCAAGGTGGGAGG

ATCACTTGAGCCCAGGAGTTCAACACCAGCCTGGGCAACATAGTGAGACCCTGT

CTCTACTAAAAATACAAAAATTAGCCAGGCATGGTGCCACACACCTGTGCTCTCA

GCTACTCAGGAGGCTGAGGCAGGAGGATCGCTTGAGCCCAGAAGGTCAAGGTTG

CAGTGAACCATGTTCAGGCCGCTGCACTCCAGCCTGGGTGACAGAGCAAGACCC

TGTTTATAAATACATAATGCTTTCCAAGTGATTAAACCGACTCCCCCCTCACCCTG

CCCACCATGGCTCCAAAGAAGCATTTGTGGAGCACCTTCTGTGTGCCCCTAGGTA

CTAGATGCCTGGACGGGGTCAGAAGGACCCTGACCCACCTTGAACTTGTTCCACA

CAGGATGCCAGGCCAAGGTGGAGCAAGCGGTGGAGACAGAGCCGGAGCCCGAG

CTGCGCCAGCAGACCGAGTGGCAGAGCGGCCAGCGCTGGGAACTGGCACTGGGT

CGCTTTTGGGATTACCTGCGCTGGGTGCAGACACTGTCTGAGCAGGTGCAGGAGG

AGCTGCTCAGCTCCCAGGTCACCCAGGAACTGAGGTGAGTGTCCCCATCCTGGCC

CTTGACCCTCCTGGTGGGCGGCTATACCTCCCCAGGTCCAGGTTTCATTCTGCCCC

TGTCGCTAAGTCTTGGGGGGCCTGGGTCTCTGCTGGTTCTAGCTTCCTCTTCCCAT

TTCTGACTCCTGGCTTTAGCTCTCTGGATATCTCTCTCTCAGCTTTGTCTCTCTCTC

TTCCCTTCTGACTCAGTCTCTCACACTCGTCCTGGCTCTGTCTCTGTCCTTCCCTAG

CTCTTTTATATAGAGACAGAGAGATGGGGTCTCACTGTGTTGCCCAGGCTGGTCT

TGAACTTCTGGGCTCAAGCGATCCTCCCGCCTCGGCCTCCCAAAGTGCTGGGATT

AGAGGCATGAGCCACCTTGCCCGGCCTCCTAGCTCCTTCTTCGTCTCTGCCTCTGC

CCTCTGCATCTGCTCTCTGCATCTGTCTCTGTCTCCTTCTCTCGGCCTCTGCCCCGT

TCCTTCTCTCCCTCTTGGGTCTCTCTGGCTCATCCCCATCTCGCCCGCCCCATCCC

AGCCCTTCTCCCCGCCTCCCACTGTGCGACACCCTCCCGCCCTCTCGGCCGCAGG

GCGCTGATGGACGAGACCATGAAGGAGTTGAAGGCCTACAAATCGGAACTGGAG

GAACAACTGACCCCGGTGGCGGAGGAGACGCGGGCACGGCTGTCCAAGGAGCT

GCAGGCGGCGCAGGCCCGGCTGGGCGCGGACATGGAGGACGTGCGCGGCCGCC

TGGTGCAGTACCGCGGCGAGGTGCAGGCCATGCTCGGCCAGAGCACCGAGGAGC

TGCGGGTGCGCCTCGCCTCCCACCTGCGCAAGCTGCGTAAGCGGCTCCTCCGCGA

TGCCGATGACCTGCAGAAGCGCCTGGCAGTGTACCAGGCCGGGGCCCGCGAGGG

CGCCGAGCGCGGCCTCAGCGCCATCCGCGAGCGCCTGGGGCCCCTGGTGGAACA

GGGCCGCGTGCGGGCCGCCACTGTGGGCTCCCTGGCCGGCCAGCCGCTACAGGA

GCGGGCCCAGGCCTGGGGCGAGCGGCTGCGCGCGCGGATGGAGGAGATGGGCA

GCCGGACCCGCGACCGCCTGGACGAGGTGAAGGAGCAGGTGGCGGAGGTGCGC

GCCAAGCTGGAGGAGCAGGCCCAGCAGATACGCCTGCAGGCCGAGGCCTTCCAG

GCCCGCCTCAAGAGCTGGTTCGAGCCCCTGGTGGAAGACATGCAGCGCCAGTGG

GCCGGGCTGGTGGAGAAGGTGCAGGCTGCCGTGGGCACCAGCGCCGCCCCTGTG
```

-continued

CCCAGCGACAATCACTGAACGCCGAAGCCTGCAGCCATGCGACCCCACGCCACC

CCGTGCCTCCTGCCTCCGCGCAGCCTGCAGCGGGAGACCCTGTCCCCGCCCCAGC

CGTCCTCCTGGGGTGGACCCTAGTTTAATAAAGATTCACCAAGTTTCACGCA

SEQ ID NO: 3: Trem2p (249 amino acids, R47H mutation)
MGPLHQFLLLLITALSQALNTTVLQGMAGQSLRVSCTYDALKHWGRHKAWCRQLG

EEGPCQRVVSTHGVWLLAFLKKRNGSTVIADDTLAGTVTITLKNLQAGDAGLYQCQ

SLRGREAEVLQKVLVEVLEDPLDDQDAGDLWVPEESSSFEGAQVEHSTSRQVSSCGS

PLAYHLPPLSKESRDLLPTIILHSSPPGLRSPEQVSCSQHPLGCGQGQAEAGNTCGQR

AGLWPRCWAPTSDPHWTRRYVREF

SEQ ID NO: 4: mutated mouse genomic DNA sequence encoding Trem2p
(1056 nucleotides)
ACTTCAAGGGAAAAGCAAGATCTTGCACAAGGTCCCCTCCGGCTGGCTGCTGGC

AAAGGAAAGGTGCCATGGGACCTCTCCACCAGTTTCTCCTGCTGCTGATCACAGC

CCTGTCCCAAGCCCTCAACACCACGGTGCTGCAGGGCATGGCCGGCCAGTCCTTG

AGGGTGTCATGTACTTATGACGCCTTGAAGCACTGGGGGAGACACAAaGCaTGGT

GTCGGCAGCTGGGTGAGGAGGGCCCATGCCAGCGTGTGGTGAGCACACACGGTG

TGTGGCTGCTGGCCTTCCTGAAGAAGCGGAATGGGAGCACAGTCATCGCAGATG

ACACCCTTGCTGGAACCGTCACCATCACTCTGAAGAACCTCCAAGCCGGTGACGC

GGGCCTCTACCAGTGTCAGAGTCTCCGAGGCCGAGAGGCTGAGGTCCTGCAGAA

AGTACTGGTGGAGGTGCTGGAGGACCCTCTAGATGACCAAGATGCTGGAGATCT

CTGGGTCCCCGAGGAGTCATCGAGTTTCGAGGGTGCCCAAGTGGAACACAGCAC

CTCCAGGCAGGTTTCATCCTGTGGGTCACCTCTAGCCTACCACCTTGGTCCTCTTT

CCAAGGAATCAAGAGACCTCCTTCCCACCCACCTCCATTCTTCTCCTCCTGGCCT

GCGTTCTCCTGAGCAAGTTTCTTGCAGCCAGCATCCTCTGGGCTGTGGCCAGGGG

CAGGCAGAAGCCGGGAACACCTGTGGTCAGAGGGCTGGACTGTGGCCAAGATGC

TGGGCACCAACTTCAGATCCTCACTGGACCCGGAGGTACGTGAGAGAATTCTGA

GTGGGAGGAGAACTACAGCTTAAGTCCAGCCAGGAGTCAATCCAGCCTGCATGC

TCTCCCCTCCTCCACCAAGACTTCTGTTTCTGCTACTTTTGCTTCAGAGGCCGCCT

CTGCCTCAAGCCCACCTATCCTGGGAGCAGGAATACTGGTGTGTACATCTGTGTT

GAGTGGGGAAGACAGCTGGATGGTTGTCTGTCAACTTCTGCACTTTGGACATTAA

ACATTCTCCACACACCAA

SEQ ID NO: 5: Trem2p (249 amino acids, mouse wild type protein,
no R47H mutation)
MGPLHQFLLLLITALSQALNTTVLQGMAGQSLRVSCTYDALKHWGRRKAWCRQLG

EEGPCQRVVSTHGVWLLAFLKKRNGSTVIADDTLAGTVTITLKNLQAGDAGLYQCQ

SLRGREAEVLQKVLVEVLEDPLDDQDAGDLWVPEESSSFEGAQVEHSTSRQVSSCGS

PLAYHLPPLSKESRDLLPTHLHSSPPGLRSPEQVSCSQHPLGCGQGQAEAGNTCGQR

AGLWPRCWAPTSDPHWTRRYVREF

SEQ ID NO: 6: mouse wild type genomic DNA sequence encoding Trem2
mouse wild type protein (1056 nucleotides)
ACTTCAAGGGAAAAGCAAGATCTTGCACAAGGTCCCCTCCGGCTGGCTGCTGGC

AAAGGAAAGGTGCCATGGGACCTCTCCACCAGTTTCTCCTGCTGCTGATCACAGC

CCTGTCCCAAGCCCTCAACACCACGGTGCTGCAGGGCATGGCCGGCCAGTCCTTG

AGGGTGTCATGTACTTATGACGCCTTGAAGCACTGGGGGAGACGCAAGGCCTGG

```
TGTCGGCAGCTGGGTGAGGAGGGCCCATGCCAGCGTGTGGTGAGCACACACGGT

GTGTGGCTGCTGGCCTTCCTGAAGAAGCGGAATGGGAGCACAGTCATCGCAGAT

GACACCCTTGCTGGAACCGTCACCATCACTCTGAAGAACCTCCAAGCCGGTGAC

GCGGGCCTCTACCAGTGTCAGAGTCTCCGAGGCCGAGAGGCTGAGGTCCTGCAG

AAAGTACTGGTGGAGGTGCTGGAGGACCCTCTAGATGACCAAGATGCTGGAGAT

CTCTGGGTCCCCGAGGAGTCATCGAGTTTCGAGGGTGCCCAAGTGGAACACAGC

ACCTCCAGGCAGGTTTCATCCTGTGGGTCACCTCTAGCCTACCACCTTCCTCCTCT

TTCCAAGGAATCAAGAGACCTCCTTCCCACCCACCTCCATTCTTCTCCTCCTGGCC

TGCGTTCTCCTGAGCAAGTTTCTTGCAGCCAGCATCCTCTGGGCTGTGGCCAGGG

GCAGGCAGAAGCCGGGAACACCTGTGGTCAGAGGGCTGGACTGTGGCCAAGATG

CTGGGCACCAACTTCAGATCCTCACTGGACCCGGAGGTACGTGAGAGAATTCTG

AGTGGGAGGAGAACTACAGCTTAAGTCCAGCCAGGAGTCAATCCAGCCTGCATG

CTCTCCCCTCCTCCACCAAGACTTCTGTTTCTGCTACTTTTGCTTCAGAGGCCGCC

TCTGCCTCAAGCCCACCTATCCTGGGAGCAGGAATACTGGTGTGTACATCTGTGT

TGAGTGGGGAAGACAGCTGGATGGTTGTCTGTCAACTTCTGCACTTTGGACATTA

AACATTCTCCACACACCAA
```

SEQ ID NO: 7: Trem2 CRISPR guide
```
GAAGCACTGGGGGAGACGCA
```

SEQ ID NO:8: Trem2 repair oligo (183 nucleotides) containing a nucleotide G>A point mutation (at nucleotide 89 in this oligo sequence) for amino acid sequence change at R47H and 2 silent mutations (lysine AAG>AAA (at nucleotide 93 in this oligo sequence) and alanine GCC>GCA (at nucleotide 96 in this oligo sequence)) into the gene to prevent re-cutting of the donor sequence in homologous directed repair:

```
GCCCTCAACACCACGGTGCTGCAGGGCATGGCCGGCCAGTCCTTGAGGGT

GTCATGTACTTATGACGCCTTGAAGCACTGGGGGAGACACAaGCaTGGTG

TCGGCAGCTGGGTGAGGAGGGCCCATGCCAGCGTGTGGTGAGCACACACG

GTGTGTGGCTGCTGGCCTTCCTGAAGAAGCGG
```

SEQ ID NO:9: 5' homology arm (4980 nucleotides: mouse Apoe4 exon 1 and 757 nucleotides of mouse Apoe4 intron 2 sequence) included in the "humanized" mouse ApoE construct inserted into the mouse genome.

```
CCTGTATCTCAGGGTTGAGAGGGAAGAGAGTGGGGTTTCCAGATGCCCAC

ATCCCTTGATACCTAGTCCTCACCCAACTCTGCTCTCCTAGTGAACAACT

GGTTGGCTACAGTAACGCTGGGCCAGGCAGGCATGCATGCGACGTATTAC

CACAAAGCCAGTGACCAGGTGAGCCGGAGGGAGCGCCTAGCTGTGGGTCC

CAGGCTGGGTTTGCTGGTGCAGTTGGTATGCCCAGGAGTCCTAATGGGCC

ACTCACATGTGTGCCGGGCCCTCTCTCCCCCAGCTGCAGGTGGGTGTGGA

GTTTGAGGCCAGCACCAGGATGCAGGACACCAGTGCCTCCTTTGGGTATC

AGCTGGACCTGCCCAAGGCCAACTTCCTTTTTAAAGGTAAGGAAGGCTCA

GCTTCCCTCCTGGGGAACAGGCCAGATAAGACTCAGCTGTCTGTGGTAGA

GTCCATGGGAAATAGGGAGGTTGAACATGTGCTGGTGGAGTGGGCGGGGA

CTCTGTGCAGCTCCAAATTACTCTGGGTGGCTTGTCAAACAGTGGGGCTC

CTACCCTGGCATGTTTAGTACATGTTGGGGGCCTCGCTTTAAGCCCTCTC

TTCCCATTCCCATCTAGCAAGCTCTCTGGCCCTCCCCACTCACTCTTACC

TTACTTGGAGTTCTTCTATTGTGTGATGAAACACTATGATGGTAAACAGC

TTAGGGAGCAAAGAGGTTATGTTGGGTTACAACTCTCAGGTGGCATGCCT

ACCACTGAGGAGAAGATGGGGCAGGACTCAGCAGAAAGCTGAAGGCAAGC

TGATGCAGAAGGCCTTGTGGGAGTGCTGCTTGTTGGCTTGCTCCTTATGG

CTTCCTCAGCCTGCTCTTATAGCCTCCGGACCATTAGCCCAGGGTGCCCC

ACTGAAAATAATCTGGGTACTCCCACATCAATCACTTAGAAAGTGCCCTA

CAGGCTTGCCTGCTGCCCTAGCTAATGGAGACATATGTATTGAGGTTCCC

TCAGCTGGATCTCTTGAGTTCAAGACCAGCCTGGTCTACAGAGCAAGTTC

TGGGACAGCCAGGGCTACCCAGAGAAACCCTGTCTCAGAAAAGAAAAAAA

AGAAAAAGGTGGGGGTGGGGTGACTAGCTTGTATAAAACTAGCCAGCACA

GCAGGGAAGCTGTGTGAATAGTGACAGCCAGGTTCAGAACCTCATTCTGC

GCAGTGACATGGGTTTGTCAAGCCTGGGCGGTGTTGAGCCACTTAAAGGG

TTGCTGTGATGGTCTGGAGTGGCCTTGGTTGTGACTTAGGACATACGGGT

CCGTTGTGGCTACCATAGAGATGGGTGGCCAGGCACATCAAGCCACCCAG

TCTCTGCCCCGCTCTCGGCCCACAGGCTCTGTGAACAGTAACTGGATCGT

GGGCGCCACGCTGGAGAAGAAGCTTCCGCCCTTGCCCCTGACACTGTCCC
```

```
TCTGCGCCTTCCTGAACCACCGCAAGAATAAGTTCCTGTGTGGCTTCGGC
CTCACCATCGGCTGAGCCCTCCTGTCCTTCCTGTGCAGACCATCGCTGGG
CCGGCTGCCCTCCCCTCCTCTCCCTCTCTCTTGGGGTTGGGGCAGTGGGA
AGGAGGGGACCTCCCATGCCCAAGGATCCCCAGCGCCAGGGGACAGTGCC
CAGGGGGCCTGGGGTCCCGGAGGGAGTCCTGGGATCTGAAGGGCATTCGA
TTGTGAGCGCCCAGGCAGAGGCGCAGAGGCGGCTGTACACAGGCTCAGAA
AGGAAAGACTTGATGTCCTCCTGAGGGCAGCAGAGGAGCGCCGAGCCGCC
TGTCACTTCCCCCTCCACCCCTCCATAGAAATCATGTTTATAAGTTATGG
AAAACCGGGACATTTTACAGAAAAAAAAAAACTTAAAAAACAAAAAATAT
ACGTGGAAAAAAAAATAGGATCTGGGAGGCCTCGGTTTTCTCCAGTTGTT
GACATGGTTGCCAGCAGGCGGCGCCGAGGGTTCAGAAAGCACAGCAGCAC
CAAGCAGTTTAGAGAAAGCTTGGCCAGGCATGGTCACACCCTCTGCTCTT
GGGGACTTACACTGCCGGAACATCAGAGGCCTGGCCTCACCAGGAGGGTG
GCTCCAGGTCACTCGCCTCTGTGCAGTCTGGCCCCGAGAGCTGGCAGAGG
ACTTTGTCTCTGTAAACAGGGTGGGGCAGGGAGACGGGGCTCAGGAGCC
TCCCTGTCCCAAAACGGGCTGAGGTGGTAGCTTGTGCTGACTTTCTCCCA
GTGGGAAGGTCAGAGGTCTCAGAAACTTCAGGAAGAAACGGAGTTCCTGG
AAGTTCAGCACAATAAGGAAAGTTACTCTGGGAGGAACGGGCCCTAGCAC
CTTCCCAGGCTGAAACAGGAAATGTCAAGTTGTTTTGTTTTTAAATTTT
GTTGAAGATGTAGCTCTGGGCCTCACGTGTCAGGCAGGTGCTGCTGGGTT
CCCTATAGTGCTTTTCCGTGAGGCCTGCTCTGGGGTGTGCGATAAGGGCC
TCAGATTGGGCTCTGCATCTCACTGCTGCACCTCATGGCATCCCAAGGGA
AGCAAAGACTCACGATGAACTGGTCAGTGTCCTAGACCGCAGCACTAAGA
CCCTCTCTACTGCCTGGGCTGGAGATGGGAGCTGGCCCTTAGCAACCCAT
GAAAATCATCTCACCACACCCAGTCCTTGCCAGTGTTTTCTGAAGCCAAA
GCTAACAGGCCTGGGCCTGGCCAGGCACCCTGTACGTACCCTTGGAGCCA
GGTGTTCCGCCTCTGCCCATCCTGCAGAATCATGTTTTGCCGTGTCTGGT
GCCAAACACTGCTATGTGGCTTCTCTCCTGCCATCAACAGCTGGGAACAG
GGAACCTTGTGCAGGCAGTGCTTCTAGCAAGCTTGCTGTGGTCTCTGAGC
CCCTTGTCCTACCTGACTTCCCAGGTACAATGGCTTTCCCACTTTTTGGG
GGTTTTGTTGTTGTTGGGTTTTTTTTGTTTTCAAGACAGGGTTTCTCT
GTGTAGTCCTGTCGGTCCTGGAACTCACTTTGTAGACCAGGCTGGCCTCC
AACTCAGAAATTCACCTGCCTCTGCCTCCAAGTGCTGGGATTATGGGATT
AAAGGCATGTGCCACCACGCCCAGCTGGCTTTTCCACTTTTTAGCCAGGA
CTTCATTCTATTACCTGAGCTCGGGATCTTCCTGCCTCAGCTTTGCATAT
GGCTAGCACTATAGACCCATGTTCCAGTGAATGACTTATGGCTTGTCTTT
TTTTTTTTTTTTTTTTTTATGTGCATTAGTGTTTTGCCTGCATGTA
TGCCTTCGTGAGGGTAGCAGATCTTGGTGTTACAGTTGTGAGCTGCTGTG
TGGGTGCTGCGATTTTGAACCTAGGTCCTGTGAAATGCAGTCAGTGCTCC
TAACCTCTGAGTCATCTCTCCAGCTCCTGCTCTTCTGCTTTTATGAGGAA
AAAGAAAAGAGAAGTGGCTTGAGAGTGGAAAATGCACATGCAGGGGTGCA
CACCTGCAGTCCCAGCATGCTACAGCAGAGGCAGAAGGACCTTTGTGGGT
TAGAGGGCAGCCTGAGAATCTTATCTCAAAACAACTTTTTAAAATGTGCT
CTGTAGGGGTAGCTCTTCCCTCCCAAGGTGACACATCTGGCAATCGCCAG
AAACAGATCAGGAGCATCAACGCTTGGTTTCCCAGGGCTTGGCTTAATGT
ATGGCTTCAAACCCATCGGGAGCCACCACTGAACAGCTCCTGAAGGAACT
GGAGCACGTCCCAGCCTTGGAATGGAAAGAGTTCACCTGTGGTGGAGGAA
TCAACAACGAGGGATCCCAGAACAACGATCTTCACCCCAGAAGCTGAGCC
TCTTAGCCCCCACCCACCCATTTCCATTTAGGCTGCCAGCTCTTTTCTTT
ACAATGCACCAGACCCCGCGGGGAAAGGGAAGGAGCGGTTCTCAGTGCCC
CAGTACCAAGGCCTGGATTATTCAATGAGGTGTCCGCTCCCTTTGTTGGC
GGGGGAGGGGAGCGGGGGGTCACAAGGCATCCAAACTCCACCTCTTTCCT
CTGCCCTGCTGTGAAGGGGAGAGAACAACCCGCCTCGTGACAGGGGGCT
GGCACAGCCCGCCCTAGCCCTGAGGAGGGGGCGGGACAGGGGGAGTCCTA
TAATTGGACCGGTCTGGGATCCGATCCCCTGCTCAGACCCTGGAGGCTAA
GGACTTGTTTCGGAAGGAGCTGGTAAGACAAGCTGGGCTGGGGATTCACC
CAGGGACCTTGGTAGGATGTGGGCTGGGAACCTTGAGATCCCCCGGAGTC
CAGGAAACAGGCACAAGAATTGGAAAAGCAGGCAGCACGATAGAAGTCTT
GGGGGACAAACTAAGGACTCGAGGTAACTAGCCTTTGCCAGAGTCAGAGC
AGGTGGAGGGGTTACCTCCAGGAAGGAGTACGGGACTGTCGGTGCACGGC
GTACCGGCTCAACTAGGAACCATCCTATGGCGAAAAAACTCGGGATGAGC
CTTAGGCTGCTTTTATATAAATACCTACTGATTTCCATCACAGTCCCCAA
GTAACCCGGACTGGTTTCAAACTGTGGCTCCTCATGGCTGAGCTCCCTAA
GTTCTGTAGTTGTGGGAGGGTACCACTTCGCAGGGATGGAGGACGATTAA
AAATCGTGTTAAATTAACACAAAATGGAAAGCAGGACTTAGCCGGGAAGA
AAGAGGAATGTAAGCTGGACCACCCGCTGGCCCTCTGTGAAGTGGAATTT
GAACCCTAGGAGAGGGAGCTGGAATTTTTGGCAGCGGATCCACCCCGGGG
TGCCGAGATAGCGAACTCGGCAAGGGGAGGTAAACAGACCTTTGGGAAGA
GCGGGTGCTCTGTTTTGGAGATGTTTGTGATGGCTCACAGATCTGAGAAG
GGAAGATGGGGTTCTCTGGGTGGCCGGAGTCCCTCCACCCCCGCCCCCTG
GTGTTCAAAGACAATTTTTCCCTCCGCAG
```

SEQ ID NO:10: DNA sequence including exons 2, 3 and 4 of the human APOE4 gene and 1500 nucleotides 3'UTR of the human, APOE4 gene after exon 4 (4292 nucleotides) included in the "humanized." mouse ApoE construct inserted into the mouse genome.

```
ACTGGCCAATCACAGGCAGGAAGATGAAGGTTCTGTGGGCTGCGTTGCTG
GTCACATTCCTGGCAGGTATGGGGGCGGGGCTTGCTCGGTTCCCCCCGCT
CCTCCCCCTCTCATCCTCACCTCAACCTCCTGGCCCCATTCAGGCAGACC
CTGGGCCCCCTCTTCTGAGGCTTCTGTGCTGCTTCCTGGCTCTGAACAGC
GATTTGACGCTCTCTGGGCCTCGGTTTCCCCCATCCTTGAGATAGGAGTT
AGAAGTTGTTTTGTTGTTGTTGTTGTTGTTGTTTTGTTTTTTGAG
```

```
ATGAAGTCTCGCTCTGTCGCCCAGGCTGGAGTGCAGTGGCGGGATCTCGG
CTCACTGCAAGCTCCGCCTCCCAGGTCCACGCCATTCTCCTGCCTCAGCC
TCCCAAGTAGCTGGGACTACAGGCACATGCCACCACACCCGACTAACTTT
TTTGTATTTTCAGTAGAGACGGGGTTTCACCATGTTGGCCAGGCTGGTCT
GGAACTCCTGACCTCAGGTGATCTGCCCGTTTCGATCTCCCAAAGTGCTG
GGATTACAGGCGTGAGCCACCGCACCTGGCTGGGAGTTAGAGGTTTCTAA
TGCATTGCAGGCAGATAGTGAATACCAGACACGGGGCAGCTGTGATCTTT
ATTCTCCATCACCCCCACACAGCCCTGCCTGGGGCACACAAGGACACTCA
ATACATGCTTTTCCGCTGGGCGCGGTGGCTCACCCCTGTAATCCCAGCAC
TTTGGGAGGCCAAGGTGGGAGGATCACTTGAGCCCAGGAGTTCAACACCA
GCCTGGGCAACATAGTGAGACCCTGTCTCTACTAAAAATACAAAAATTAG
CCAGGCATGGTGCCACACACCTGTGCTCTCAGCTACTCAGGAGGCTGAGG
CAGGAGGATCGCTTGAGCCCAGAAGGTCAAGGTTGCAGTGAACCATGTTC
AGGCCGCTGCACTCCAGCCTGGGTGACAGAGCAAGACCCTGTTTATAAAT
ACATAATGCTTTCCAAGTGATTAAACCGACTCCCCCCTCACCCTGCCCAC
CATGGCTCCAAAGAAGCATTTGTGGAGCACCTTCTGTGTGCCCCTAGGTA
CTAGATGCCTGGACGGGGTCAGAAGGACCCTGACCCACCTTGAACTTGTT
CCACACAGGATGCCAGGCCAAGGTGGAGCAAGCGGTGGAGACAGAGCCGG
AGCCCGAGCTGCGCCAGCAGACCGAGTGGCAGAGCGGCCAGGGCTGGAA
CTGGCACTGGGTCGCTTTTGGGATTACCTGCGCTGGGTGCAGACACTGTC
TGAGCAGGTGCAGGAGGAGCTGCTCAGCTCCCAGGTCACCCAGGAACTGA
GGTGAGTGTCCCCATCCTGGCCCTTGACCCTCCTGGTGGGCGGCTATACC
TCCCCAGGTCCAGGTTTCATTCTGCCCCTGTCGCTAAGTCTTGGGGGCC
TGGGTCTCTGCTGGTTCTAGCTTCCTCTTCCCATTTCTGACTCCTGGCTT
TAGCTCTCTGGATATCTCTCTCTCAGCTTTGTCTCTCTCTCTTCCCTTCT
GACTCAGTCTCTCACACTCGTCCTGGCTCTGTCTCTGTCCTTCCCTAGCT
CTTTTATATAGAGACAGAGAGATGGGTCTCACTGTGTTGCCCAGGCTGG
TCTTGAACTTCTGGGCTCAAGCGATCCTCCCGCCTCGGCCTCCCAAAGTG
CTGGGATTAGAGGCATGAGCCACCTTGCCCGGCCTCCTAGCTCCTTCTTC
GTCTCTGCCTCTGCCCTCTGCATCTGCTCTCTGGATCTGTCTCTGTCTCC
TTCTCTCGGCCTCTGCCCCGTTCCTTCTCTCCCTCTTGGGTCTCTCTGGC
TCATCCCCATCTCGCCCGCCCCATCCCAGCCCTTCTCCCCGCCTCCCACT
GTGCGACACCCTCCCGCCCTCTCGGCCGCAGGGCGCTGATGGACGAGACC
ATGAAGGAGTTGAAGGCCTACAAATCGGAACTGGAGGAACAACTGACCCC
GGTGGCGGAGGAGACGCGGGCACGGCTGTCCAAGGAGCTGCAGGCGGCGC
AGGCCCGGCTGGGCGCGGACATGGAGGACGTGCGCGGCCGCCTGGTGCAG
TACCGCGGCGAGGTGCAGGCCATGCTCGGCCAGAGCACCGAGGAGCTGCG
GGTGCGCCTCGCCTCCCACCTGCGCAAGCTGCGTAAGCGCTCCTCCGCG
ATGCCGATGACCTGCAGAAGCGCCTGGCAGTGTACCAGGCCGGGGCCCGC
GAGGGCGCCGAGCGCGGCCTCAGCGCCATCCGCGAGCGCCTGGGGCCCCT
GGTGGAACAGGGCCGCGTGCGGGCCGCCACTGTGGGCTCCCTGGCCGGCC
AGCCGCTACAGGAGCGGGCCCAGGCCTGGGGCGAGCGGCTGCGCGCGCGG
ATGGAGGAGATGGGCAGCCGGACCCGCGACCGCCTGGACGAGGTGAAGGA
GCAGGTGGCGGAGGTGCGCGCCAAGCTGGAGGAGCAGGCCCAGCAGATAC
GCCTGCAGGCCGAGGCCTTCCAGGCCCGCCTCAAGAGCTGGTTCGAGCCC
CTGGTGGAAGACATGCAGCGCCAGTGGGCCGGGCTGGTGGAGAAGGTGCA
GGCTGCCGTGGGCACCAGCGCCGCCCCTGTGCCCAGCGACAATCACTGAA
CGCCGAAGCCTGCAGCCATGCGACCCCACGCCACCCCGTGCCTCCTGCCT
CCGCGCAGCCTGCAGCGGGAGACCCTGTCCCCGCCCAGCCGTCCTCCTG
GGGTGGACCCTAGTTTAATAAAGATTCACCAAGTTTCACGCATCTGCTGG
CCTCCCCCTGTGATTTCCTCTAAGCCCCAGCCTCAGTTTCTCTTTCTGCC
CACATACTGGCCACACAATTCTCAGCCCCCTCCTCTCCATCTGTGTCTGT
GTGTATCTTTCTCTCTGCCCTTTTTTTTTTTTAGACGGAGTCTGGCTC
TGTCACCCAGGCTAGAGTGCAGTGGCACGATCTTGGCTCACTGCAACCTC
TGCCTCTTGGGTTCAAGCGATTCTGCTGCCTCAGTAGCTGGGATTACAGG
CTCACACCACCACACCCGGCTAATTTTTGTATTTTTAGTAGAGACGAGCT
TTCACCATGTTGGCCAGGCAGGTCTCAAACTCCTGACCAAGTGATCCACC
CGCCGGCCTCCCAAAGTGCTGAGATTACAGGCCTGAGCCACCATGCCCGG
CCTCTGCCCCTCTTTCTTTTTAGGGGGCAGGGAAAGGTCTCACCCTGTC
ACCCGCCATCACAGCTCACTGCAGCCTCCACCTCCTGGACTCAAGTGATA
AGTGATCCTCCCGCCTCAGCCTTTCCAGTAGCTGAGACTACAGGCGCATA
CCACTAGGATTAATTTGGGGGGGGGGTGGTGTGTGTGGAGATGGGGTCT
GGCTTTGTTGGCCAGGCTGATGTGGAATTCCTGGGCTCAAGCGATACTCC
CACCTTGGCCTCCTGAGTAGCTGAGACTACTGGCTAGCACCACCACACCC
AGCTTTTTATTATTATTTGTAGAGACAAGGTCTCAATATGTTGCCCAGGC
TAGTCTCAAACCCCTGGGCTCAAGAGATCCTCCGCCATCGGCCTCCCAAA
GTGCTGGGATTCCAGGCATGGGCTCCGAGCCCGGCCTGCCCAACTTAAT
AATACTTGTTCCTCAGAGTTGCAACTCCAAATGACCTGAGATTGGTGCCT
TTATTCTAAGCTATTTTCATTTTTTTCTGCTGTCATTATTCTCCCCCTT
CTCTCCTCCAGTCTTATCTGATATCTGCCTCCTTCCCACCCACCCTGCAC
CCCATCCCACCCCTCTGTCTCTCCCTGTTCTCCTCAGGAGACTCTGGCTT
CCTGTTTTCCTCCACTTCTATCTTTTATCTCTCCCTCCTACGGTTTCTTT
TCTTTCTCCCCGGCCTGCTTGTTTCTCCCCCAACCCCCTTCATCTGGATT
TCTTCTTCTGCCATTCAGTTTGGTTTGAGCTCTCTGCTTCTCCGGTTCCC
TCTGAGCTAGCTGTCCCTTCACCCACTGTGAACTGGGTTTCCCTGCCCAA
CCCTCATTCTCTTTCTTTCTTTCTTTTTTTTTTTTTTTTTTTTT
TTTTGAGACAGAGTCTTGCTCTGTTGCCCAGCCTGGAGTGCAGTGGTGCA
ATCTTGGTTCACTGCAACCTCCACTTCCCAGATTCAAGCAATTCTCCTGC
CTCAGCCTCCAGAGTAGCTGGGATTACAGGCGTGTCCACCACACCCGAC
TAATTTTTGTATTTTTGGTAGAGACAAGGCTTCGGCATTGTT
```

SEQ ID NO:11: a Frt PGKneo Fit cassette followed by an NdeI restriction enzyme site (CATATG) (1834 nucleotides) inserted in the "humanized" mouse ApoE construct between nucleotides 9272 and 9273 to allow for selection prior to recombinase-mediated removal of this cassette.

GAAGTTCCTATTCTCTAGAAAGTATAGGAACTTCAGGTCTGAAGAGGAGT
TTACGTCCAGCCAAGCTAGCTTGGCTGCAGGTCGTCGAAATTCTACCGGG
TAGGGGAGGCGCTTTTCCCAAGGCAGTCTGGAGCATGCGCTTTAGCAGCC
CCGCTGGGCACTTGGCGCTACACAAGTGGCCTCTGGCCTCGCACACATTC
CACATCCACCGGTAGGCGCCAACCGGCTCCGTTCTTTGGTGGCCCCTTCG
CGCCACCTTCTACTCCTCCCCTAGTCAGGAAGTTCCCCCCCGCCCCGCAG
CTCGCGTCGTGCAGGACGTGACAAATGGAAGTAGCACGTCTCACTAGTCT
CGTGCAGATGGACAGCACCGCTGAGCAATGGAAGCGGGTAGGCCTTTGGG
GCAGCGGCCAATAGCAGCTTTGCTCCTTCGCTTTCTGGGCTCAGAGGCTG
GGAAGGGGTGGGTCCGGGGCGGGCTCAGGGGCGGGCTCAGGGGCGGGGC
GGGCGCCCGAAGGTCCTCCGGAGGCCCGGCATTCTGCACGCTTCAAAAGC
GCACGTCTGCCGCGCTGTTCTCCTCTTCCTCATCTCCGGGCCTTTCGACC
TGCAGCCTGTTGACAATTAATCATCGGCATAGTATATCGGCATAGTATAA
TACGACAAGGTGAGGAACTAAACCATGGGATCGGCCATTGAACAAGATGG
ATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTG
TCAGCGCAGGGGCGCCCGGTTCTTTTTGTCAAGACCGACCTGTCCGGTGC
CCTGAATGAACTGCAGGACGAGGCAGCGCGGCTATCGTGGCTGGCCACGA
CGGGCGTTCCTTGCGCAGCTGTGCTCGACGTTGTCACTGAAGCGGGAAGG
GACTGGCTGCTATTGGGCGAAGTGCCGGGGCAGGATCTCCTGTCATCTCA
CCTTGCTCCTGCCGAGAAAGTATCCATCATGGCTGATGCAATGCGGCGGC
TGCATACGCTTGATCCGGCTACCTGCCCATTCGACCACCAAGCGAAACAT
CGCATCGAGCGAGCACGTACTCGGATGGAAGCCGGTCTTGTCGATCAGGA
TGATCTGGACGAAGAGCATCAGGGGCTCGCGCCAGCCGAACTGTTCGCCA
GGCTCAAGGCGCGCATGCCCGACGGCGATGATCTCGTCGTGACCCATGGC
GATGCCTGCTTGCCGAATATCATGGTGGAAAATGGCCGCTTTTCTGGATT
CATCGACTGTGGCCGGCTGGGTGTGGCGGACCGCTATCAGGACATAGCGT
TGGCTACCCGTGATATTGCTGAAGAGCTTGGCGGCGAATGGGCTGACCGC
TTCCTCGTGCTTTACGGTATCGCCGCTCCCGATTCGCAGCGCATCGCCTT
CTATCGCCTTCTTGACGAGTTCTTCTGAGGGGATCAATTCTCTAGAGCTC
GCTGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATT
CTATTCTGGGGGGTGGGGTGGGGCAGGACAGCAAGGGGGAGGATTGGGAA
GACAATAGCAGGCATGCTGGGGATGCGGTGGGCTCTATGGCTTCTGAGGC
GGAAAGAACCAGCTGGGGCTCGACTAGAGCTTGCGGAACCCTTCGAAGTT
CCTATTCTCTAGAAAGTATAGGAACTTCCATATG

SEQ ID NO:12: 3' homology arm (5166 nucleotides) included in the "humanized" mouse ApoE construct inserted into the mouse genome.

AAACCTGATGGAGAAGATACAGGCCTCTGTGGCTACCAACCCCATCATCA
CCCCAGTGGCCCAGGAGAATCAATGAGTATCCTTCTCCTGTCCTGCAACA
ACATCCATATCCAGCCAGGTGGCCCTGTCTCAAGCACCTCTCTGGCCCTC
TGGTGGCCCTTGCTTAATAAAGATTCTCCGAGCACATTCTGAGTCTCTGT
GAGTGATTCCAATCAGCTTCAGCCTCAGTTTATTGTTTTTTGCCTTACCT
AGCACACATTCCATGGCCCTGTCACTATCTGTAGAGGGAGGTGGTTTTGC
AGCAATAGAAATGAAGCCTAGGACCTAGCAACATAAAAGAACAAGTGATC
TACCACTGAGCCACGCCCACAGCCCCTCACTGGGGGATTCTAGGCAGGGG
CTCTACCACTGAGCCACCCGCAGCCCCTCACTGGGGAATCATATCTACCA
CTGAGTCACGCCCCTCCAGCCCCTCACTACGGGAATTCTAGTCAGTAGCT
CTACCACTGAGCCACACCCACAGCCTCTGGGGCTCTTCACCGCCCCTAC
CCCTGGATTCTAGGCATGGGCTCATTTTATTTATTTATTTATTTAAGATT
TGTTTATCTTATGTATAAGGTACACTGCAGCTGTCTTCAGGCGTCAGGTC
CCATTACAGATGGTTGTGAGCCACCATGTGGTTGCTGGGAATTGAACTCA
GGACTTATAGAAGAGTAGTCAGTGCTCTTAACTGCTGAGCCATCTCTCCA
GCACCCAGTACAGGCTCTTCTATTTAGCTATATCCACCCTTCTTTTTAGT
CTGAAATAGGATCTCAACTGATTTTCCTTGCACTCCCTCTAGCCTAGTTT
GGTCTTGAATATTTGAATCTTTGTTTTCAAATCAATCTCTACAGGAACTG
AGAAAGGCATGTACCACTTCATGTGGGTCAGTTGGGCTACTTTTCCCAAC
TTCCCAAGCACCCACTGCACAGCTATGCCTTGAATCAATCAACATGTAAG
AGACCAGGGTCGCCAGGCGGTGTTTACTTTTCTGGTTGTCTTATCTCTCC
TCCTCCGCTCTAGTCTTATCTGACACCCTCTCCTTGCCTTGTCTCTCCTC
TTTTTCCCTTCTAGGCTTCCTTTTCTGGCTTCCTGTTTTCCTGATCCTCT
GTTATCTCACCCTCCCGCGGTTTCTTTTGCTCTGGGCCTTTGGTTGGCGG
TTTCTACGGTTTCTACGTGGCTTTTGGAACCTCAGCCTTTCTCCCTTGCT
CTGAAGTTAGCTGGATCTTTGCTCCCTCTGGGTCATGGGGCCTTAGCCCC
ATTCTTTCTCCCCTGCCTGTGCTGCATGCCTTTTGACTTTCCCAGCAAGT
GTATGGAGAGTGAGTTCAGGCTGGGGACACAAAACCATTCTCCCCATGTC
CTGGTACTCAAAGGGGTCATGGTGGAAGCTGGAGAGCCCCTGGCTGGCTT
CTCCTCCCACCCCCTCAGTTCTCAGGGACTCAGCAGGGCTCCCACTAACA
GGGGCAGGCTAGGGCTTGAGCTGTGTCTTGGGTCGGGCCAAGGCTTCAGA
ACTCAACTGCCTCTGGCACACCCCGAGCCTGCAGCTTTTCCTGGCATCAA
ACTCAGCATTATCTGGAGGCAGGCACCACTCCCACACATGACTCATTAGG
CCCAATGAGAAGATGGGTCGGTGGGCTAGTGACAGGGCCCTAGACAGCCA
CACTTCATGCCCAGGGGCTAGGAGCACACCCCCAGAGCCTCACTACTCTC
AAATATCAAGATGAGGGGAGAGTATAGAGGGAATGTCTCCCTCTGAAGAC
CTGAATTATTGTGATGTTATTTGAGCCACGCTGGCCTTGAACTCTGAACC
CTCCTGCCTCATCTTCAAAGGCTGGAATTACAGGTTCGCGCCACTAGGCC

```
TATCTGAGAACTTAGTTAATTCTACAGAAGAGAGTTTGTTTTCACTGGTT
TGAAACGAGGCCTCGTGTACCCAGAGCTACTCTTTTGCCAACTCACTGTA
GAGCCAAGGATGACCTTGAACTCTGGTCTTCCTGGCTCCGAGTCCTCGGT
ACTGGGTAGACAATGTGTGATCCTAACCCCCAGTTTTATGTGGTGCTATA
CAGATGGCATCCAGGGTTTCCTGCATGCTGGACAGGTCATCAACCAACCG
AGCCACATCCTCCTCATCATCATCACTTTGTTGTTGGTTTTCAATCCAGA
GCTCATGGAGCCCAAGCTGGCCTCAATCTATATAACCAAGACTGTGCCTG
GTCTTCCTGTCTCTACCTAACAAATGATGGTGGGATGCAGGGATGTACAA
CCAGGAGCAGAGCCTTACTTCTAAACGAAGAAGGAACCCCACCTCCCTGT
GGGCAGACCTGGAGGTGGGGCAAGGACCACAGAAAGACATTACAGAACTA
GGATCGTGAAGGAAGTCATGGAGGCCAGCCTGTTGTACAGAGTGAGTTCC
AGGACAGCCAGGGCTACACAGAGGAAAACAAGAAGGAAAAAAAAAAAAAA
AAAAAGAACTGAATGACTAGCAGTTTTAGAACCTTAGCTGTGTGCTTCCC
GTACCCTACCTGTGGCACAGGAAGCCCTTGTTGCTAAGAGTAGGATGACA
CTGGAAGCACCAAGCACTGGGCAGAGTAAGGGGGAAATCTGTTACATTAT
TCAGATGGGCGCTTGAGGACTGAGCAGGACTCCTTTCAAGAAGCAAAAGG
GTCAGGCCTGGTGCCCACAGGGACTGGAAGCTAGCTAGCGCCGAGTTGGC
CCCAGAGATGTCGCAACCCAGCCAGGGTCGAGAATCTGTTCCACCCCTTT
CACAACCATCCCCTGTTGTCGTCGTCCCCACCCCCACCCCCGCCCCAAC
TGACACGTGGGTTGCAGGGGCACCAGGCCAGCCAACCTAGAGTCTGGGCC
CCTTAGCCACCAGCTGCCAGGGGTCACTGTCGGTCAATGACAGCTCTGG
GGGAGGGGGGAGAAGGGCCTTGGACTCTAGCCTGAGAGAAAGGATGTTG
TGGAAGGAGGGGCAGGGAGGCAAGTTTAGGGCCTGCAGGGGCCTAGGAG
GCCCCACAAGACCTAAAAACGGGGAAGGGGGTTGTGCCAGTTAGGGGA
CACTATGGAGCTCTGCAAGCTAAGAGGCTCTTAGCTTCTTTGCAGTTTTG
ACTAGCTGAAGAGGCAACTTCTAAGGAAGGGAGATGAGGGGATGCCAAGA
TCCCAGAGAGCATCCGAGGAGGTCTGAGGGTGTGCAGATGCAAAGGCATT
GGAGGTGAAGGGAGCCAGGGTGCAGCATCCGGGACAGAATGTGAGCTGAG
GCTCCTGGTCAAGGAGAAGGTAGAAGAGCTAACCTGAGGATGCAGTGT
GAGCTAGGGGTGAGATGGGGGTGAGGGGAGTTGTTTGTAAGACCCCCCCC
CTTAAGGTGGGACAGCCTCAGAGAGAGAGTGAGTAGGCAGAGCAGCCAAG
GCTGGGTGGAGATCAATGAGATTTGGAAGTGAGGATGCTGACCAGTGACG
AGCCTTGGGCCTAAATAAAAAGCCTGGATGTGGGATCTGCCTCCCAGTAT
CGACCAGAATGACAGAAGAGAGTGGGCTGGTTGTGTTGGTGTTGGTGCAT
GCCTGTAATCCCAGCAACTCACTAGAGAGGCAGAGGCAGGAGCATCAACA
ATTCCAGGCCAGCCAAAAGCCTATGTAAAAAAAAAAAAAAGAGAAAAAA
GAAAAAGAAAAAGTAGGTGGACACAGAGACAAGGGGAGGCTCAGGGGG
AGGGCGACCAGCTTGCTCCGCCCCTCCCCAACCGGTTAAACCTCTGTGC
AGGATCCTCCCACCGCGATGGGCCTCCTGAGAGATCCTTAGATCCAGGTT
AGTGCATAGGAAAGTGTCCCCCCACTACCTACAGCTAAGGGATTGGGGTG
GTGGGATCATGGTGGAGGGCGGTGGTGAATACTAGCGATGTCCCCCGCTA
CCCGTGCGTCTGCCTCCAGGGTGCCCCTCCAACCAGGATGAGGCTCTTCA
TCGCTCTTCCTGTCCTGATTGTGGTCGTAGCCATGACCTTGGAAGGTAAG
AAAGAGCCTTGGAAGGTAAGAAAGAGGCTTGGAAGTGTGAAGTTGGCCTT
GTGCCTGCGGCCCAGGCTTAGAAGACCCTCGAGGAGGGCTCTGAGGTCCC
TTTCTGTGTCATCATTCCACTACCGCCCTCCCATCGTCCCCATCCCACC
TGCCAGGTGCCTTATTTTTGTGTCAAAGTGGGTGCTGAAGGAGGCAACTC
TGTCCAGAAAAGACGCAGTAACCAATGACCTAGGATACCACCCTTTGGAA
TTGGCTAATCTTCCTAGAAGGGGCGGAGCGTAAAAACAAGGAGGTGAGAG
GTGCAGTAAAATCAAGTGTCCAATACCCTCCCCCATGCTAATGAGTTTGC
TCGCAACCCTCTCGCGGCAGGCCCAGCCCCCGCCCAGGCGGCCCCGGATT
TGTCCGGAACATTGGAGAGCATACCGGATAAACTGAAGGAGTTTGGGAAC
ACTTTGGAAGACAAGGCCCGGGCAGCCATTGAACATATCAAACAGAAGGA
AATTTTGACCAAGACCCGGTTAGGACCTTTCAGGGCACGGGCGGGTGGTG
TGTGTGTGTGCGTGCGCGCGCCCGTGTGTAAAAGCCCTAGCAGACA
GTTCCACACTGACACAATGGGGAAACTGCACCAGAGTGTTTGACACTTTC
CCTGAAGTCATAGAACTGTATCTGAAGTCATTGAACTGGATGTCAAAGTG
CTCGTAGTGTGGAGACAGGCGGTGTAACTCCCAGCCAACTGTTAGAGATG
TTTCCAAGTCCTAGTGAAGGGCCAAGCTAGGCGGCTGACTGGTTAGGACA
GACCCTGACCCCTCCCTGTGTACTCTTGAGACAGGTCATGACTTGAGTCT
CCGAGACAGAGAAAGAATGTAGGAGAGTTGGGGCAGGGGCACAGCAGAAG
CTGTACAGGCCTGGGCTCTGCAGTTTACACTGGCCAAAGAGAGATTAGGG
CATGCTGGGTTAAGAACTAGCCAGGCAGTGGTGGCGCACACCTTTGATCC
CAGTATTCATGAGGCAGAGGCAGGCAGATCTCTTTGAGGCCAGCCTGATT
GGAGCTAGTTCTAGGAAAGCCAGGGCTACACAGAGAAACCCTGTCTCAAC
ACCACCACCACCCCCC

SEQ ID NO: 13: wild-type amino acid sequence-mouse
Apoe
MKALWAVLLVTLLTGCLAEGEPEVTDQLEWQSNQPWEQALNRFWDYLRWV
QTLSDQVQEELQSSQVTQELTALMEDTMTEVKAYKKELEEQLGPVAEETR
ARLGKEVQAAQARLGADMEDLRNRLGQYRNEVHIMLGQSTEEIRARLSTH
LRKMRKRLMRDAEDLQKRLAVYKAGAREGAERGVSAIRERLGPLVEQGRQ
RTANLGAGAAQPLRDRAQAFGDRIRGRLEEVGNQARDRLEEVREHMEEVR
SKMEEQTQQIRLQAEIFQARLKGWFEPIVEDMHRQWANLMEKIQASVATN
PIITPVAQENQ SEQ ID NO: 14: amino acid sequence-human APOE3
MKVLWAALLVTFLAGCQAKVEQAVETEPEPELRQQTEWQSGQRWEEALGR
FWDYLRWVQTLSEQVQEELLSSQVTQELRALMDETMKELKAYKSELEEQL
TPVAEETRARLSKELQAAQARLGADMEDVCGRLVQYRGEVQAMLGQSTEE
LRVRLASHLRKLRKRLLRDADDEQKRLAVYQAGAREGAERGLSAIRERLG
PLVEQGRVRAATVGSLAGQPLQERAQAWGERLRARMEEMGSRTRDRLDEV
KRQVAEVRAKLEEQAQQIRLQAEAFQARLKSWFEPLVEDMQRQWAGLVEK
VQAAVGTSAAPVPSDNH
```

-continued

SEQ ID NO: 15: APOE4p (299 amino acids)
KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVRGRLVQYRGEVQAMLGQSTEELRVRLASHLRKLRKRLLR

DADDLQKRLAVYQAGAREGAERGLSAIRERLGPLVEQGRVRAATVGSLAG

QPLQERAQAWGERLRARMEEMGSRTRDRLDEVKEQVAEVRAKLEEQAQQI

RLQAEAFQARLKSWFEPLVEDMQRQWAGLVEKVQAAVGTSAAPVPSDNH

Any patents or publications mentioned in this specification are incorporated herein by reference to the same extent as if each individual publication is specifically and individually indicated to be incorporated by reference.

The genetically modified mice and methods of use described herein are presently representative of preferred embodiments, exemplary, and not intended as limitations on the scope of the invention. Changes therein and other uses will occur to those skilled in the art Such changes and other uses can be made without departing from the scope of the invention as set forth in the claims.

What is claimed is:

1. A mouse whose genome comprises: (a) a genetically modified endogenous apolipoprotein E (apoE) allele comprising a nucleic acid encoding a humanized apolipoprotein E4 APOE4 protein (APOE4p), wherein the nucleic acid encoding the humanized APOE4p comprises exon 1 of the mouse ApoE4 gene, and exons 2-4 of the human APOE4 gene; and (b) a genetically modified endogenous allele comprising a nucleic acid encoding a mouse triggering receptor expressed on myeloid cells 2 (TREM2) protein modified to include a R47H substitution (TREM2p) relative to mouse wild type TREM2, wherein the mouse is homozygous for the modified apoE allele encoding the human APOE4p and is homozygous for the modified apoE allele encoding the mouse TREM2p, and the mouse exhibits one or more signs of non-familial late-onset Alzheimer's disease associated with expression of the human APOE4p and the mouse TREM2p.

2. The mouse of claim 1, wherein the one or more signs of non-familial late-onset Alzheimer's disease are selected from APOE4-dependent alterations in cholesterol metabolism, cerebrovascular leakage, and inflammation, relative to a control mouse that does not comprise the nucleic acid encoding a human APOE4p and the nucleic acid encoding a mouse TREM2p.

3. The mouse of claim 1, wherein one or more of the following genes is differentially expressed in the mouse, relative to a control mouse that does not comprise the nucleic acid encoding a human APOE4p and the nucleic acid encoding a mouse TREM2p: Pcsk2, Mapk10, Mapk9, Prkcq, Slc18a2, Plcb2, Slc6a4, Gng2, Prkcq, Akt3, Gnao1, Plcb3, Arrb2, Il6, Myh10, Gng2, Cnr1, Stx1a, Arrb2, Unc13a, Cdk5, Calb1, Slc6a4, Gria4, Cnr1, Thy1, Mapk10, Hcn1, Cdk5, Chl1, Il6, Mapk9, Myh10, Uchl1, Cnr1, Amph, Cdk5, Calb1, Chl1, Slc6a4, Chmp2b, Akt3, Mapk10, Mapk9, Casp7, Prkcq, Cnr1, Slc18a2, and Gnao1.

4. The mouse of claim 2, wherein the one or more signs of non-familial late-onset Alzheimer's disease is APOE4-dependent alterations in cholesterol metabolism.

5. The mouse of claim 2, wherein the one or more signs of non-familial late-onset Alzheimer's disease is cerebrovascular leakage.

6. The mouse of claim 2, wherein the one or more signs of non-familial late-onset Alzheimer's disease is inflammation.

* * * * *

SEQUENCE LISTING

```
<160> NUMBER OF SEQ ID NOS: 17

<210> SEQ ID NO 1
<211> LENGTH: 317
<212> TYPE: PRT
<213> ORGANISM: Homo sapiens

<400> SEQUENCE: 1

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Arg Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
```

275                 280                 285
Asp Met Gln Arg Gln Trp Ala Gly Leu Val Glu Lys Val Gln Ala Ala
            290                 295                 300
Val Gly Thr Ser Ala Ala Pro Val Pro Ser Asp Asn His
305                 310                 315

<210> SEQ ID NO 2
<211> LENGTH: 2792
<212> TYPE: DNA
<213> ORGANISM: Homo sapiens

<400> SEQUENCE: 2

| | | | | | |
|---|---|---|---|---|---|
| actggccaat | acaggcagg | aagatgaagg | ttctgtgggc | tgcgttgctg | gtcacattcc | 60 |
| tggcaggtat | gggggcgggg | cttgctcggt | tcccccgct | cctccccctc | tcatcctcac | 120 |
| ctcaacctcc | tggccccatt | caggcagacc | ctgggcccc | tcttctgagg | cttctgtgct | 180 |
| gcttcctggc | tctgaacagc | gatttgacgc | tctctgggcc | tcggtttccc | ccatccttga | 240 |
| gataggagtt | agaagttgtt | ttgttgttgt | tgtttgttgt | tgttgttttg | ttttttttgag | 300 |
| atgaagtctc | gctctgtcgc | ccaggctgga | gtgcagtggc | gggatctcgg | ctcactgcaa | 360 |
| gctccgcctc | ccaggtccac | gccattctcc | tgcctcagcc | tcccaagtag | ctgggactac | 420 |
| aggcacatgc | caccacaccc | gactaacttt | tttgtatttt | cagtagagac | ggggtttcac | 480 |
| catgttggcc | aggctggtct | ggaactcctg | acctcaggtg | atctgcccgt | ttcgatctcc | 540 |
| caaagtgctg | ggattacagg | cgtgagccac | cgcacctggc | tgggagttag | aggtttctaa | 600 |
| tgcattgcag | gcagatagtg | aataccagac | acggggcagc | tgtgatcttt | attctccatc | 660 |
| accccacac | agccctgcct | ggggcacaca | aggacactca | atacatgctt | ttccgctggg | 720 |
| cgcggtggct | caccctgta | atcccagcac | tttgggaggc | caaggtggga | ggatcacttg | 780 |
| agcccaggag | ttcaacacca | gcctgggcaa | catagtgaga | ccctgtctct | actaaaaata | 840 |
| caaaaattag | ccaggcatgg | tgccacacac | ctgtgctctc | agctactcag | gaggctgagg | 900 |
| caggaggatc | gcttgagccc | agaaggtcaa | ggttgcagtg | aaccatgttc | aggccgctgc | 960 |
| actccagcct | gggtgacaga | gcaagaccct | gtttataaat | acataatgct | ttccaagtga | 1020 |
| ttaaaccgac | tcccccctca | ccctgcccac | catggctcca | agaagcatt | tgtggagcac | 1080 |
| cttctgtgtg | ccctaggta | ctagatgcct | ggacggggtc | agaaggaccc | tgacccacct | 1140 |
| tgaacttgtt | ccacacagga | tgccaggcca | aggtggagca | agcggtggag | acagagccgg | 1200 |
| agcccgagct | gcgccagcag | accgagtggc | agagcggcca | gcgctgggaa | ctggcactgg | 1260 |
| gtcgcttttg | ggattacctg | cgctgggtgc | agacactgtc | tgagcaggtg | caggaggagc | 1320 |
| tgctcagctc | ccaggtcacc | caggaactga | ggtgagtgtc | cccatcctgg | cccttgaccc | 1380 |
| tcctggtggg | cggctatacc | tccccaggtc | caggtttcat | tctgcccctg | tcgctaagtc | 1440 |
| ttgggggggcc | tgggtctctg | ctggttctag | cttcctcttc | ccatttctga | ctcctggctt | 1500 |
| tagctctctg | gatatctctc | tctcagcttt | gtctctctct | cttcccttct | gactcagtct | 1560 |
| ctcacactcg | tcctggctct | gtctctgtcc | ttccctagct | cttttatata | gagacagaga | 1620 |
| gatggggtct | cactgtgttg | cccaggctgg | tcttgaactt | ctgggctcaa | gcgatcctcc | 1680 |
| cgcctcggcc | tcccaaagtg | ctgggattag | aggcatgagc | caccttgccc | ggcctcctag | 1740 |
| ctccttcttc | gtctctgcct | ctgccctctg | catctgctct | ctgcatctgt | ctctgtctcc | 1800 |
| ttctctcggc | ctctgccccg | ttccttctct | ccctcttggg | tctctctggc | tcatcccat | 1860 |
| ctcgcccgcc | ccatcccagc | ccttctcccc | gcctcccact | gtgcgacacc | ctcccgccct | 1920 |

```
ctcggccgca gggcgctgat ggacgagacc atgaaggagt tgaaggccta caaatcggaa    1980
ctggaggaac aactgacccc ggtggcggag gagacgcggg cacggctgtc caaggagctg    2040
caggcggcgc aggcccggct gggcgcggac atggaggacg tgcgcggccg cctggtgcag    2100
taccgcggcg aggtgcaggc catgctcggc cagagcaccg aggagctgcg ggtgcgcctc    2160
gcctcccacc tgcgcaagct gcgtaagcgg ctcctccgcg atgccgatga cctgcagaag    2220
cgcctggcag tgtaccaggc cggggcccgc gagggcgccg agcgcggcct cagcgccatc    2280
cgcgagcgcc tggggcccct ggtggaacag gccgcgtgc gggccgccac tgtgggctcc    2340
ctggccggcc agccgctaca ggagcgggcc caggcctggg gcgagcggct gcgcgcgcgg    2400
atggaggaga tgggcagccg gacccgcgac cgcctggacg aggtgaagga gcaggtggcg    2460
gaggtgcgcg ccaagctgga ggagcaggcc agcagatac gcctgcaggc cgaggccttc    2520
caggcccgcc tcaagagctg gttcgagccc ctggtggaag acatgcagcg ccagtgggcc    2580
gggctggtgg agaaggtgca ggctgccgtg gcaccagcg ccgcccctgt gcccagcgac    2640
aatcactgaa cgccgaagcc tgcagccatg cgaccccacg ccaccccgtg cctcctgcct    2700
ccgcgcagcc tgcagcggga gaccctgtcc ccgccccagc cgtcctcctg gggtggaccc    2760
tagtttaata aagattcacc aagtttcacg ca                                  2792
```

<210> SEQ ID NO 3
<211> LENGTH: 249
<212> TYPE: PRT
<213> ORGANISM: Artificial Sequence
<220> FEATURE:
<223> OTHER INFORMATION: Mouse Trem2 protein having the R47H point mutation

<400> SEQUENCE: 3

```
Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg His Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
        115                 120                 125

Leu Glu Asp Pro Leu Asp Asp Gln Asp Ala Gly Asp Leu Trp Val Pro
    130                 135                 140

Glu Glu Ser Ser Ser Phe Glu Gly Ala Gln Val Glu His Ser Thr Ser
145                 150                 155                 160

Arg Gln Val Ser Ser Cys Gly Ser Pro Leu Ala Tyr His Leu Pro Pro
                165                 170                 175

Leu Ser Lys Glu Ser Arg Asp Leu Leu Pro Thr His Leu His Ser Ser
            180                 185                 190

Pro Pro Gly Leu Arg Ser Pro Glu Gln Val Ser Cys Ser Gln His Pro
```

```
            195                 200                 205
Leu Gly Cys Gly Gln Gly Gln Ala Glu Ala Gly Asn Thr Cys Gly Gln
    210                 215                 220

Arg Ala Gly Leu Trp Pro Arg Cys Trp Ala Pro Thr Ser Asp Pro His
225                 230                 235                 240

Trp Thr Arg Arg Tyr Val Arg Glu Phe
                245

<210> SEQ ID NO 4
<211> LENGTH: 1056
<212> TYPE: DNA
<213> ORGANISM: Artificial Sequence
<220> FEATURE:
<223> OTHER INFORMATION: DNA encoding mouse Trem2 protein having the
      R47H point mutation

<400> SEQUENCE: 4
acttcaaggg aaaagcaaga tcttgcacaa ggtcccctcc ggctggctgc tggcaaagga       60
aaggtgccat gggacctctc caccagtttc tcctgctgct gatcacagcc ctgtcccaag      120
ccctcaacac cacggtgctg cagggcatgg ccggccagtc cttgagggtg tcatgtactt      180
atgacgcctt gaagcactgg gggagacaca agcatggttc tcggcagctg gtgaggagg       240 gcccatgcca gcgtgtggtg agcacacacg gtgtgtggct gctggccttc ctgaagaagc      300
ggaatgggag cacagtcatc gcagatgaca cccttgctgg aaccgtcacc atcactctga      360
agaacctcca agccggtgac gcgggcctct accagtgtca gagtctccga ggccgagagg      420
ctgaggtcct gcagaaagta ctggtggagg tgctggagga ccctctagat gaccaagatg      480
ctggagatct ctgggtcccc gaggagtcat cgagtttcga gggtgcccaa gtggaacaca      540
gcacctccag gcaggtttca tcctgtgggt cacctctagc ctaccacctt cctcctcttt      600
ccaaggaatc aagagacctc cttcccaccc acctccattc ttctcctcct ggcctgcgtt      660
ctcctgagca agtttcttgc agccagcatc tctgggctg tggccagggg caggcagaag       720
ccgggaacac ctgtggtcag agggctggac tgtggccaag atgctgggca ccaacttcag      780
atcctcactg gacccggagg tacgtgagag aattctgagt gggaggagaa ctacagctta      840
agtccagcca ggagtcaatc cagcctgcat gctctcccct cctccaccaa gacttctgtt      900
tctgctactt tgcttcaga ggccgcctct gcctcaagcc cacctatcct gggagcagga       960
atactggtgt gtacatctgt gttgagtggg gaagacagct ggatggttgt ctgtcaactt     1020
ctgcactttg gacattaaac attctccaca caccaa                               1056

<210> SEQ ID NO 5
<211> LENGTH: 249
<212> TYPE: PRT
<213> ORGANISM: Mus musculus

<400> SEQUENCE: 5

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
                20                  25                  30

Arg Val Ser Cys Thr Tyr Asp Ala Leu Lys His Trp Gly Arg Arg Lys
            35                  40                  45

Ala Trp Cys Arg Gln Leu Gly Glu Glu Gly Pro Cys Gln Arg Val Val
        50                  55                  60

Ser Thr His Gly Val Trp Leu Leu Ala Phe Leu Lys Lys Arg Asn Gly
```

```
                    65                  70                  75                  80
Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
                100                 105                 110

Leu Arg Gly Arg Glu Ala Glu Val Leu Gln Lys Val Leu Val Glu Val
                115                 120                 125

Leu Glu Asp Pro Leu Asp Asp Gln Asp Ala Gly Asp Leu Trp Val Pro
            130                 135                 140

Glu Glu Ser Ser Ser Phe Glu Gly Ala Gln Val Glu His Ser Thr Ser
145                 150                 155                 160

Arg Gln Val Ser Ser Cys Gly Ser Pro Leu Ala Tyr His Leu Pro Pro
                165                 170                 175

Leu Ser Lys Glu Ser Arg Asp Leu Leu Pro Thr His Leu His Ser Ser
                180                 185                 190

Pro Pro Gly Leu Arg Ser Pro Glu Gln Val Ser Cys Ser Gln His Pro
                195                 200                 205

Leu Gly Cys Gly Gln Gly Gln Ala Glu Ala Gly Asn Thr Cys Gly Gln
            210                 215                 220

Arg Ala Gly Leu Trp Pro Arg Cys Trp Ala Pro Thr Ser Asp Pro His
225                 230                 235                 240

Trp Thr Arg Arg Tyr Val Arg Glu Phe
                245

<210> SEQ ID NO 6
<211> LENGTH: 1056
<212> TYPE: DNA
<213> ORGANISM: Mus musculus

<400> SEQUENCE: 6
acttcaaggg aaaagcaaga tcttgcacaa ggtcccctcc ggctggctgc tggcaaagga      60
aaggtgccat gggacctctc caccagtttc tcctgctgct gatcacagcc ctgtcccaag     120
ccctcaacac cacggtgctg cagggcatgg ccggccagtc cttgagggtg tcatgtactt     180
atgacgcctt gaagcactgg gggagacgca aggcctggtt tcggcagctg ggtgaggagg     240
gcccatgcca gcgtgtggtg agcacacacg tgtgtggct gctggccttc ctgaagaagc     300
ggaatgggag cacagtcatc gcagatgaca cccttgctgg aaccgtcacc atcactctga     360
agaacctcca gccggtgac gcgggcctct accagtgtca gagtctccga ggccgagagg     420
ctgaggtcct gcagaaagta ctggtggagg tgctggagga ccctctagat gaccaagatg     480
ctggagatct ctgggtcccc gaggagtcat cgagtttcga gggtgcccaa gtggaacaca     540
gcacctccag gcaggtttca tcctgtgggt cacctctagc ctaccacctt cctcctcttt     600
ccaaggaatc aagagacctc cttcccaccc acctccattc ttctcctcct ggcctgcgtt     660
ctcctgagca agtttcttgc agccagcatc tctgggctg tggccagggg caggcagaag     720
ccgggaacac ctgtggtcag agggctggac tgtggccaag atgctgggca ccaacttcag     780
atcctcactg gacccggagg tacgtgagag aattctgagt gggaggagaa ctacagctta     840
agtccagcca ggagtcaatc cagcctgcat gctctcccct cctccaccaa gacttctgtt     900
tctgctactt ttgcttcaga ggccgcctct gcctcaagcc acctatcct gggagcagga      960 atactggtgt gtacatctgt gttgagtggg aagacagct ggatggttgt ctgtcaactt     1020
ctgcactttg gacattaaac attctccaca caccaa                              1056
```

```
<210> SEQ ID NO 7
<211> LENGTH: 20
<212> TYPE: DNA
<213> ORGANISM: Artificial Sequence
<220> FEATURE:
<223> OTHER INFORMATION: Trem2 CRISPR guide

<400> SEQUENCE: 7
gaagcactgg gggagacgca                                                   20

<210> SEQ ID NO 8
<211> LENGTH: 183
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (89)..(89)
<223> OTHER INFORMATION: n may be g or a
<220> FEATURE:
<221> NAME/KEY: misc_feature
<222> LOCATION: (93)..(93)
<223> OTHER INFORMATION: n may be g or a
<220> FEATURE:
<221> NAME/KEY: misc_feature
<222> LOCATION: (96)..(96)
<223> OTHER INFORMATION: n may be g or c

<400> SEQUENCE: 8
gccctcaaca ccacggtgct gcagggcatg gccggccagt ccttgagggt gtcatgtact        60
tatgacgcct tgaagcactg ggggagacnc aangcntggt gtcggcagct gggtgaggag       120
ggcccatgcc agcgtgtggt gagcacacac ggtgtgtggc tgctggcctt cctgaagaag       180
cgg                                                                    183

<210> SEQ ID NO 9
<211> LENGTH: 4980
<212> TYPE: DNA
<213> ORGANISM: Mus musculus

<400> SEQUENCE: 9
cctgtatctc agggttgaga gggaagagag tggggtttcc agatgcccac atcccttgat        60
acctagtcct cacccaactc tgctctccta gtgaacaact ggttggctac agtaacgctg       120
ggccaggcag gcatgcatgc gacgtattac cacaaagcca gtgaccaggt gagccggagg       180
gagcgcctag ctgtgggtcc caggctgggt ttgctggtgc agttggtatg cccaggagtc       240
ctaatgggcc actcacatgt gtgccgggcc ctctctcccc cagctgcagg tgggtgtgga       300
gtttgaggcc agcaccagga tgcaggacac cagtgcctcc tttgggtatc agctggacct       360
gcccaaggcc aacttccttt ttaaaggtaa ggaaggcctc agcttccctc ctggggaaca       420
ggccagataa gactcagctg tctgtggtag agtccatggg aaataggag gttgaacatg       480 tgctggtgga gtgggcgggg actctgtgca gctccaaatt actctgggtg gcttgtcaaa       540
cagtggggct cctaccctgg catgtttagt acatgttggg ggcctcgctt taagccctct       600
cttcccattc ccatctagca agctctctgg ccctccccac tcactcttac cttacttgga       660
gttcttctat tgtgtgatga aacactatga tggtaaacag cttagggagc aaagaggtta       720
tgttgggtta caactctcag gtggcatgcc taccactgag gagaagatgg ggcaggactc       780
agcagaaagc tgaaggcaag ctgatgcaga aggccttgtg ggagtgctgc ttgttggctt       840
gctccttatg gcttcctcag cctgctctta tagcctccgg accattagcc cagggtgccc       900
```

-continued

```
cactgaaaat aatctgggta ctcccacatc aatcacttag aaagtgccct acaggcttgc    960
ctgctgccct agctaatgga gacatatgta ttgaggttcc ctcagctgga tctcttgagt   1020
tcaagaccag cctggtctac agagcaagtt ctgggacagc cagggctacc cagagaaacc   1080
ctgtctcaga aaagaaaaaa aagaaaaagg tgggggtggg gtgactagct tgtataaaac   1140
tagccagcac agcagggaag ctgtgtgaat agtgacagcc aggttcagaa cctcattctg   1200
cgcagtgaca tgggttttgtc aagcctgggc ggtgttgagc cacttaaagg gttgctgtga   1260
tggtctggag tggccttggt tgtgacttag gacatacggg tccgttgtgg ctaccataga   1320
gatgggtggc caggcacatc aagccaccca gtctctgccc cgctctcggc ccacaggctc   1380
tgtgaacagt aactggatcg tgggcgccac gctggagaag aagcttccgc ccttgcccct   1440
gacactgtcc ctctgcgcct tcctgaacca ccgcaagaat aagttcctgt gtggcttcgg   1500
cctcaccatc ggctgagccc tcctgtcctt cctctgcaga ccatcgctgg gccggctgcc   1560
ctcccctcct ctccctctct cttggggttg gggcagtggg aaggagggga cctcccatgc   1620
ccaaggatcc ccagcgccag gggacagtgc ccaggggggcc tggggtcccg gagggagtcc   1680
tgggatctga agggcattcg attgtgagcg cccaggcaga ggcgcagagg cggctgtaca   1740
caggctcaga aaggaaagac ttgatgtcct cctgagggca gcagaggagc gccgagccgc   1800
ctgtcacttc cccctccacc cctccataga aatcatgttt ataagttatg gaaaaccggg   1860
acattttaca gaaaaaaaaa aacttaaaaa acaaaaaata tacgtggaaa aaaaaatagg   1920
atctgggagg cctcggtttt ctccagttgt tgacatggtt gccagcaggc ggcgccgagg   1980
gttcagaaag cacagcagca ccaagcagtt tagagaaagc ttggccaggc atggtcacac   2040
cctctgctct tggggactta cactgccgga acatcagagg cctggcctca ccaggagggt   2100
ggctccaggt cactcgcctc tgtgcagtct ggccccgaga gctggcagag gactttgtct   2160
ctgtaaacag ggtgggggca gggagacggg gctcaggagc ctccctgtcc caaaacgggc   2220
tgaggtggta gcttgtgctg actttctccc agtgggaagg tcagaggtct cagaaacttc   2280
aggaagaaac ggagttcctg gaagttcagc acaataagga aagttactct gggaggaacg   2340
ggccctagca ccttcccagg ctgaaacagg aaatgtcaag ttgttttgtt ttttaaattt   2400
tgttgaagat gtagctctgg gcctcacgtg tcaggcaggt gctgctgggt tccctatagt   2460
gcttttccgt gaggcctgct ctggggtgtg cgataagggc ctcagattgg gctctgcatc   2520
tcactgctgc acctcatggc atcccaaggg aagcaaagac tcacgatgaa ctggtcagtg   2580
tcctagaccg cagcactaag accctctcta ctgcctgggc tggagatggg agctggccct   2640
tagcaaccca tgaaaatcat ctcaccacac ccagtccttg ccagtgtttt ctgaagccaa   2700
agctaacagg cctgggcctg gccaggcacc ctgtacgtac ccttggagcc aggtgttccg   2760
cctctgccca tcctgcagaa tcatgttttg ccgtgtctgg tgccaaacac tgctatgtgg   2820
cttctctcct gccatcaaca gctgggaaca gggaaccttg tgcaggcagt gcttctagca   2880
agcttgctgt ggtctctgag ccccttgtcc tacctgactt cccaggtaca atggctttcc   2940
cacttttggg gggttttgtt gttgttgggt tttttttgt ttttcaagac agggtttctc   3000
tgtgtagtcc tgtcggtcct ggaactcact ttgtagacca ggctggcctc caactcagaa   3060
attcacctgc ctctgcctcc aagtgctggg attatgggat taaaggcatg tgccaccacg   3120
cccagctggc ttttccactt tttagccagg acttcattct attacctgag ctcgggatct   3180
tcctgcctca gctttgcata tggctagcac tatagaccca tgttccagtg aatgacttat   3240
```

```
ggcttgtcctt tttttttttt tttttttttt tttatgtgca ttagtgtttt gcctgcatgt   3300
atgccttcgt gagggtagca gatcttggtg ttacagttgt gagctgctgt gtgggtgctg   3360
cgattttgaa cctaggtcct gtgaaatgca gtcagtgctc ctaacctctg agtcatctct   3420
ccagctcctg ctcttctgct tttatgagga aaaagaaaag agaagtggct tgagagtgga   3480
aaatgcacat gcaggggtgc acacctgcag tcccagcatg ctacagcaga ggcagaagga   3540
cctttgtggg ttagagggca gcctgagaat cttatctcaa acaacttttt taaaatgtgc   3600
tctgtagggg tagctcttcc ctcccaaggt gacacatctg gcaatcgcca gaaacagatc   3660
aggagcatca acgcttggtt tcccaggget tggcttaatg tatggcttca aacccatcgg   3720
gagccaccac tgaacagctc ctgaaggaac tggagcacgt cccagccttg aatggaaag   3780
agttcacctg tggtgagga atcaacaacg agggatccca gaacaacgat cttcaccccca   3840
gaagctgagc ctcttagccc ccacccaccc atttccattt aggctgccag ctcttttctt   3900
tacaatgcac cagaccccgc gggaaaggg aaggagcggt tctcagtgcc ccagtaccaa   3960
ggcctggatt attcaatgag gtgtccgctc cctttgttgg cggggaggg gagcgggggg   4020
tcacaaggca tccaaactcc acctctttcc tctgccctgc tgtgaagggg gagagaacaa   4080
cccgcctcgt gacaggggc tggcacagcc cgccctagcc ctgaggaggg ggcgggacag   4140
ggggagtcct ataattggac cggtctggga tccgatcccc tgctcagacc ctggaggcta   4200
aggacttgtt tcggaaggag ctggtaagac aagctgggct ggggattcac ccagggacct   4260
tggtaggatg tgggctggga accttgagat cccccggagt ccaggaaaca ggcacaagaa   4320
ttggaaaagc aggcagcacg atagaagtct tgggggacaa actaaggact cgaggtaact   4380
agcctttgcc agagtcagag caggtggagg ggttacctcc aggaaggagt acgggactgt   4440
cggtgcacgg cgtaccggct caactaggaa ccatcctatg gcgaaaaaac tcgggatgag   4500
ccttaggctg cttttatata aatacctact gatttccatc acagtcccca agtaacccgg   4560
actggtttca aactgtggct cctcatggct gagctcccta agttctgtag ttgtgggagg   4620
gtaccacttc gcagggatgg aggacgatta aaaatcgtgt taaattaaca caaaatggaa   4680
agcaggactt agccgggaag aaagaggaat gtaagctgga ccacccgctg gccctctgtg   4740
aagtggaatt tgaaccctag gagagggagc tggaattttt ggcagcggat ccaccccggg   4800
gtgccgagat agcgaactcg gcaaggggag gtaaacagac cttttgggaag agcgggtgct   4860
ctgttttgga gatgtttgtg atggctcaca gatctgagaa gggaagatgg ggttctctgg   4920
gtggccggag tccctccacc cccgccccct ggtgttcaaa gacaattttt ccctccgcag   4980

<210> SEQ ID NO 10
<211> LENGTH: 4292
<212> TYPE: DNA
<213> ORGANISM: Homo sapiens

<400> SEQUENCE: 10
actggccaat cacaggcagg aagatgaagg ttctgtgggc tgcgttgctg gtcacattcc     60
tggcaggtat gggggcgggg cttgctcggt tcccccccgct cctcccccctc tcatcctcac    120
ctcaacctcc tggcccccatt caggcagacc ctgggccccc tcttctgagg cttctgtgct    180
gcttcctggc tctgaacagc gatttgacgc tctctgggcc tcggtttccc ccatccttga    240
gataggagtt agaagttgtt ttgttgttgt tgtttgttgt tgttgttttg ttttttttgag    300
atgaagtctc gctctgtcgc ccaggctgga gtgcagtggg ggatctcgg ctcactgcaa     360
gctccgcctc ccaggtccac gccattctcc tgcctcagcc tcccaagtag ctgggactac    420
```

```
aggcacatgc caccacaccc gactaacttt tttgtatttt cagtagagac ggggtttcac    480
catgttggcc aggctggtct ggaactcctg acctcaggtg atctgcccgt ttcgatctcc    540
caaagtgctg ggattacagg cgtgagccac cgcacctggc tgggagttag aggtttctaa    600
tgcattgcag gcagatagtg aataccagac acggggcagc tgtgatcttt attctccatc    660 accccacac agccctgcct ggggcacaca aggacactca atacatgctt ttccgctggg    720
cgcggtggct caccctgta atcccagcac tttgggaggc caaggtggga ggatcacttg    780
agcccaggag ttcaacacca gcctgggcaa catagtgaga ccctgtctct actaaaaata    840
caaaaattag ccaggcatgg tgccacacac ctgtgctctc agctactcag gaggctgagg    900
caggaggatc gcttgagccc agaaggtcaa ggttgcagtg aaccatgttc aggccgctgc    960
actccagcct gggtgacaga gcaagaccct gtttataaat acataatgct ttccaagtga   1020
ttaaaccgac tccccctca ccctgcccac catggctcca agaagcatt tgtggagcac    1080 cttctgtgtg ccctaggta ctagatgcct ggacggggtc agaaggaccc tgacccacct   1140
tgaacttgtt ccacacagga tgccaggcca aggtggagca agcggtggag acagagccgg   1200
agcccgagct cgccagcag accgagtggc agagcggcca cgctgggaa ctggcactgg    1260 gtcgcttttg ggattacctg cgctgggtgc agacactgtc tgagcaggtg caggaggagc   1320
tgctcagctc ccaggtcacc caggaactga ggtgagtgtc cccatcctgg cccttgaccc   1380
tcctggtggg cggctatacc tccccaggtc caggtttcat tctgcccctg tcgctaagtc   1440 ttgggggcc tgggtctctg ctggttctag cttcctcttc ccatttctga ctcctggctt   1500
tagctctctg gatatctctc tctcagcttt gtctctctct cttcccttct gactcagtct   1560
ctcacactcg tcctggctct gtctctgtcc ttccctagct ctttatata gagacagaga   1620 gatggggtct cactgtgttg cccaggctgg tcttgaactt ctgggctcaa gcgatcctcc   1680
cgcctcggcc tcccaaagtg ctgggattag aggcatgagc caccttgccc ggcctcctag   1740
ctccttcttc gtctctgcct ctgccctctg catctgctct ctgcatctgt ctctgtctcc   1800
ttctctcggc ctctgccccg ttccttctct ccctcttggg tctctctggc tcatccccat   1860
ctcgcccgcc ccatcccagc ccttctcccc gcctcccact gtgcgacacc ctcccgcccc   1920
ctcggccgca gggcgctgat ggacgagacc atgaaggagt tgaaggccta caatcggaa    1980 ctggaggaac aactgacccc ggtggcgag gagacgcggg cacggctgtc caaggagctg    2040
caggcggcgc aggcccggct gggcgcggac atggaggacg tgcgcggccg cctggtgcag   2100
taccgcggca aggtgcaggc catgctcggc cagagcaccg aggagctgcg ggtgcgcctc    2160
gcctcccacc tgcgcaagct gcgtaagcgg ctcctccgcg atgccgatga cctgcagaag   2220
cgcctggcag tgtaccaggc cggggcccgc gagggcgccg agcgcggcct cagcgccatc   2280
cgcgagcgcc tggggcccct ggtggaacag gccgcgtgc gggccgccac tgtgggctcc    2340
ctggccggcc agccgctaca ggagcgggcc caggcctggg gcgagcggct gcgcgcgcgg   2400
atggaggaga tgggcagccg gacccgcgac cgcctggacg aggtgaagga gcaggtggcg   2460
gaggtgcgcg ccaagctgga ggagcaggcc cagcagatac gcctgcaggc cgaggccttc   2520
caggcccgcc tcaagagctg gttcgagccc ctggtggaag acatgcagcg ccagtgggcc   2580
gggctggtgg agaaggtgca ggctgccgtg gcaccagcg ccgcccctgt gcccagcgac   2640
aatcactgaa cgccgaagcc tgcagccatg cgaccccacg ccaccccgtg cctcctgcct   2700
ccgcgcagcc tgcagcggga gaccctgtcc ccgcccagc cgtcctcctg gggtggaccc   2760
```

```
tagtttaata aagattcacc aagtttcacg catctgctgg cctccccctg tgatttcctc    2820
taagccccag cctcagtttc tctttctgcc cacatactgg ccacacaatt ctcagccccc    2880
tcctctccat ctgtgtctgt gtgtatcttt ctctctgccc tttttttttt ttttagacgg    2940
agtctggctc tgtcacccag gctagagtgc agtggcacga tcttggctca ctgcaacctc    3000
tgcctcttgg gttcaagcga ttctgctgcc tcagtagctg ggattacagg ctcacaccac    3060
cacacccggc taattttgt atttttagta gagacgagt ttcaccatgt tggccaggca    3120
ggtctcaaac tcctgaccaa gtgatccacc cgccggcctc ccaaagtgct gagattacag    3180
gcctgagcca ccatgcccgg cctctgcccc tctttctttt ttaggggggca gggaaaggtc    3240 tcaccctgtc acccgccatc acagctcact gcagcctcca cctcctggac tcaagtgata    3300
agtgatcctc ccgcctcagc ctttccagta gctgagacta caggcgcata ccactaggat    3360
taatttgggg ggggggggtgg tgtgtgtgga gatggggtct ggctttgttg gccaggctga    3420
tgtggaattc ctgggctcaa gcgatactcc caccttggcc tcctgagtag ctgagactac    3480
tggctagcac caccacaccc agcttttat tattatttgt agagacaagg tctcaatatg    3540
ttgcccaggc tagtctcaaa cccctgggct caagagatcc tccgccatcg gcctcccaaa    3600
gtgctgggat tccaggcatg gggctccgag cccggcctgc ccaacttaat aatacttgtt    3660
cctcagagtt gcaactccaa atgacctgag attggtgcct ttattctaag ctattttcat    3720 ttttttttctg ctgtcattat tctcccccctt ctctcctcca gtcttatctg atatctgcct    3780
ccttcccacc cacccctgcac cccatcccac ccctctgtct ctccctgttc tcctcaggag    3840
actctggctt cctgttttcc tccacttcta tctttatct ctccctccta cggtttcttt    3900
tctttctccc cggcctgctt gtttctcccc caaccccctt catctggatt tcttcttctg    3960
ccattcagtt tggtttgagc tctctgcttc tccggttccc tctgagctag ctgtcccttc    4020
acccactgtg aactgggttt ccctgcccaa ccctcattct cttctttct tctttttttt    4080 tttttttttt tttttttttt ttttgagaca gagtcttgct ctgttgccca gcctggagtg    4140
cagtggtgca atcttggttc actgcaacct ccacttccca gattcaagca attctcctgc    4200
ctcagcctcc agagtagctg ggattacagg cgtgtcccac cacacccgac taattttgt    4260 attttttggta gagacaaggc ttcggcattg tt                                 4292
```

<210> SEQ ID NO 11
<211> LENGTH: 1834
<212> TYPE: DNA
<213> ORGANISM: Artificial Sequence
<220> FEATURE:
<223> OTHER INFORMATION: A Frt PGKneo Frt cassette followed by an NdeI
      restriction enzyme site (CATATG)

<400> SEQUENCE: 11

```
gaagttccta ttctctagaa agtataggaa cttcaggtct gaagaggagt ttacgtccag      60
ccaagctagc ttggctgcag gtcgtcgaaa ttctaccggg taggggaggc gcttttccca     120
aggcagtctg gagcatgcgc tttagcagcc ccgctgggca cttggcgcta cacaagtggc     180
ctctggcctc gcacacattc cacatccacc ggtaggcgcc aaccggctcc gttcttggt     240 ggccccttcg cgccaccttc tactcctccc ctagtcagga agttcccccc cgccccgcag     300
ctcgcgtcgt gcaggacgtg acaaatggaa gtagcacgtc tcactagtct cgtgcagatg     360
gacagcaccg ctgagcaatg gaagcgggta ggcctttggg gcagcggcca atagcagctt     420
tgctccttcg ctttctgggc tcagaggctg ggaagggggtg ggtccggggg cgggctcagg     480
```

-continued

```
ggcgggctca ggggcggggc gggcgcccga aggtcctccg gaggcccggc attctgcacg    540
cttcaaaagc gcacgtctgc cgcgctgttc tcctcttcct catctccggg cctttcgacc    600
tgcagcctgt tgacaattaa tcatcggcat agtatatcgg catagtataa tacgacaagg    660
tgaggaacta aaccatggga tcggccattg aacaagatgg attgcacgca ggttctccgg    720
ccgcttgggt ggagaggcta ttcggctatg actgggcaca acagacaatc ggctgctctg    780
atgccgccgt gttccggctg tcagcgcagg ggcgcccggt tctttttgtc aagaccgacc    840
tgtccggtgc cctgaatgaa ctgcaggacg aggcagcgcg gctatcgtgg ctggccacga    900
cgggcgttcc ttgcgcagct gtgctcgacg ttgtcactga agcgggaagg gactggctgc    960
tattgggcga agtgccgggg caggatctcc tgtcatctca ccttgctcct gccgagaaag   1020
tatccatcat ggctgatgca atgcggcggc tgcatacgct tgatccggct acctgcccat   1080
tcgaccacca agcgaaacat cgcatcgagc gagcacgtac tcggatggaa gccggtcttg   1140
tcgatcagga tgatctggac gaagagcatc aggggctcgc gccagccgaa ctgttcgcca   1200
ggctcaaggc gcgcatgccc gacggcgatg atctcgtcgt gacccatggc gatgcctgct   1260
tgccgaatat catggtggaa aatggccgct tttctggatt catcgactgt ggccggctgg   1320
gtgtggcgga ccgctatcag gacatagcgt tggctacccg tgatattgct gaagagcttg   1380
gcggcgaatg ggctgaccgc ttcctcgtgc tttacggtat cgccgctccc gattcgcagc   1440
gcatcgcctt ctatcgcctt cttgacgagt tcttctgagg ggatcaattc tctagagctc   1500
gctgatcagc ctcgactgtg ccttctagtt gccagccatc tgttgtttgc ccctcccccg   1560
tgccttcctt gaccctggaa ggtgccactc ccactgtcct ttcctaataa aatgaggaaa   1620
ttgcatcgca ttgtctgagt aggtgtcatt ctattctggg gggtggggtg gggcaggaca   1680
gcaaggggga ggattgggaa gacaatagca ggcatgctgg gatgcggtg ggctctatgg   1740 cttctgaggc ggaaagaacc agctggggct cgactagagc ttgcggaacc cttcgaagtt   1800
cctattctct agaaagtata ggaacttcca tatg                                1834
```

<210> SEQ ID NO 12
<211> LENGTH: 5166
<212> TYPE: DNA
<213> ORGANISM: Mus musculus

<400> SEQUENCE: 12

```
aaacctgatg gagaagatac aggcctctgt ggctaccaac cccatcatca ccccagtggc     60
ccaggagaat caatgagtat ccttctcctg tcctgcaaca acatccatat ccagccaggt    120
ggccctgtct caagcacctc tctggccctc tggtggccct tgcttaataa agattctccg    180
agcacattct gagtctctgt gagtgattcc aatcagcttc agcctcagtt tattgttttt    240
tgccttacct agcacacatt ccatggccct gtcactatct gtagagggag gtggttttgc    300
agcaatagaa atgaagccta ggacctagca acataaaaga acaagtgatc taccactgag    360
ccacgcccac agccctcac tgggggattc taggcagggg ctctaccact gagccacccg    420
cagcccctca ctggggaatc atatctacca ctgagtcacg cccctccagc ccctcactac    480
gggaattcta gtcagtagct ctaccactga gccacaccca cagcctctgg ggctcttcac    540 cgcccctac ccctggattc taggcatggg ctcatttat ttatttattt atttaagatt    600
tgtttatctt atgtataagg tacactgcag ctgtcttcag gcgtcaggtc ccattacaga    660
tggttgtgag ccaccatgtg gttgctggga attgaactca ggacttatag aagagtagtc    720
agtgctctta actgctgagc catctctcca gcacccagta caggctcttc tatttagcta    780
```

```
tatccaccct tcttttagt ctgaaatagg atctcaactg attttccttg cactccctct    840
agcctagttt ggtcttgaat atttgaatct ttgttttcaa atcaatctct acaggaactg    900
agaaaggcat gtaccacttc atgtgggtca gttgggctac ttttcccaac ttcccaagca    960
cccactgcac agctatgcct tgaatcaatc aacatgtaag agaccagggt cgccaggcgg   1020
tgtttacttt tctggttgtc ttatctctcc tcctccgctc tagtcttatc tgacaccctc   1080
tccttgcctt gtctctcctc ttttccctt ctaggcttcc ttttctggct tcctgttttc    1140
ctgatcctct gttatctcac cctcccgcgg tttcttttgc tctgggcctt ggttggcgg    1200 tttctacggt ttctacgtgg cttttggaac ctcagccttt ctcccttgct ctgaagttag   1260
ctggatcttt gctccctctg ggtcatgggg ccttagcccc attctttctc ccctgcctgt   1320
gctgcatgcc ttttgacttt cccagcaagt gtatggagag tgagttcagg ctggggacac   1380
aaaaccattc tccccatgtc ctggtactca aagggtcat ggtggaagct ggagagcccc    1440
tggctggctt ctcctcccac cccctcagtt ctcaggact cagcagggct cccactaaca    1500
ggggcaggct agggcttgag ctgtgtcttg ggtcgggcca aggcttcaga actcaactgc   1560
ctctggcaca ccccgagcct gcagcttttc ctggcatcaa actcagcatt atctggaggc   1620
aggcaccact cccacacatg actcattagg cccaatgaga agatgggtcg gtgggctagt   1680
gacagggccc tagacagcca cacttcatgc ccaggggcta ggagcacacc cccagagcct   1740
cactactctc aaatatcaag atgaggggag agtatagagg gaatgtctcc ctctgaagac   1800
ctgaattatt gtgatgttat ttgagccacg ctggccttga actctgaacc ctcctgcctc   1860
atcttcaaag gctggaatta caggttcgcg ccactaggcc tatctgagaa cttagttaat   1920
tctacagaag agagtttgtt ttcactggtt tgaaacgagg cctcgtgtac ccagagctac   1980
tcttttgcca actcactgta gagccaagga tgaccttgaa ctctggtctt cctggctccg   2040
agtcctcggt actgggtaga caatgtgtga tcctaacccc cagttttatg tggtgctata   2100
cagatggcat ccagggtttc ctgcatgctg gacaggtcat caaccaaccg agccacatcc   2160
tcctcatcat catcactttg ttgttggttt tcaatccaga gctcatggag cccaagctgg   2220
cctcaatcta taaccaag actgtgcctg gtcttcctgt ctctacctaa caaatgatgg     2280
tgggatgcag ggatgtacaa ccaggagcag agccttactt ctaaacgaag aaggaacccc   2340
acctccctgt gggcagacct ggaggtgggg caaggaccac agaaagacat tacagaacta   2400
ggatcgtgaa ggaagtcatg gaggccagcc tgttgtacag agtgagttcc aggacagcca   2460
gggctacaca gaggaaaaca agaaggaaaa aaaaaaaaa aaaagaact gaatgactag     2520 cagttttaga accttagctg tgtgcttccc gtaccctacc tgtggcacag gaagcccttg   2580
ttgctaagag taggatgaca ctggaagcac caagcactgg gcagagtaag ggggaaatct   2640
gttacattat tcagatgggc gcttgaggac tgagcaggac tcctttcaag aagcaaaagg   2700
gtcaggcctg gtgcccacag ggactggaag ctagctagcg ccgagttggc cccagagatg   2760
tcgcaaccca gccagggtcg agaatctgtt ccaccccttt cacaaccatc cccctgttgt   2820
cgtcgtcccc accccaccc ccgccccaac tgacacgtgg gttgcagggg caccaggcca    2880
gccaacctag agtctgggcc ccttagccac cagctgccag ggggtcactg tcggtcaatg   2940
acagctctgg gggagggggg gagaagggcc ttggactcta gcctgagaga aaggatgttg   3000
tggaaggagg gggcagggag gcaagtttag ggcctgcagg ggcctaggag gcccacaag    3060 acctaaaaac gggggaaggg gggttgtgcc agttagggga cactatggag ctctgcaagc   3120
```

```
taagaggctc ttagcttctt tgcagttttg actagctgaa gaggcaactt ctaaggaagg    3180
gagatgaggg gatgccaaga tcccagagag catccgagga ggtctgaggg tgtgcagatg    3240
caaaggcatt ggaggtgaag ggagccaggg tgcagcatcc gggacagaat gtgagctgag    3300
gctcctggtc aaggagaagg tagagaagag ctaacctgag gatgcagtgt gagctagggg    3360
tgagatgggg gtgaggggag ttgtttgtaa acccccccc cttaaggtgg gacagcctca    3420
gagagagagt gagtaggcag agcagccaag gctgggtgga gatcaatgag atttggaagt    3480
gaggatgctg accagtgacg agccttgggc ctaaataaaa agcctggatg tgggatctgc    3540
ctcccagtat cgaccagaat gacagaagag agtgggctgg ttgtgttggt gttggtgcat    3600
gcctgtaatc ccagcaactc actagagagg cagaggcagg agcatcacaa attccaggcc    3660
agccaaaaag cctatgtaaa aaaaaaaaaa agagaaaaaa gaaaaaagaa aaagtaggtg    3720
gacacagaga caaggggggag gctcagggg agggcgacca gcttgctccg cccctcccc    3780
aaccggttaa acctctgtgc aggatcctcc caccgccatg ggcctcctga gagatcctta    3840
gatccaggtt agtgcatagg aaagtgtccc cccactacct acagctaagg gattggggtg    3900
gtgggatcat ggtggagggc ggtggtgaat actagcgatg tcccccgcta cccgtgcgtc    3960
tgcctccagg gtgcccctcc aaccaggatg aggctcttca tcgctcttcc tgtcctgatt    4020
gtggtcgtag ccatgacctt ggaaggtaag aaagagcctt ggaaggtaag aaagaggctt    4080
ggaagtgtga agttggcctt tgcctgcgcg cccaggctta aagaccctc gaggagggct    4140
ctgaggtccc tttctgtgtc atcattccac taccgccctc ccatcgtccc catcccacc    4200
tgccaggtgc cttattttg tgtcaaagtg ggtgctgaag gaggcaactc tgtccagaaa    4260
agacgcagta accaatgacc taggatacca cccttggaa ttggctaatc ttcctagaag    4320
gggcggagcg taaaaacaag gaggtgagag gtgcagtaaa atcaagtgtc caataccctc    4380
ccccatgcta atgagtttgc tcgcaaccct ctcgcggcag gcccagcccc cgcccaggcg    4440
gccccggatt tgtccggaac attggagagc ataccgata aactgaagga gtttgggaac    4500
actttggaag acaaggcccg ggcagccatt gaacatatca aacagaagga aattttgacc    4560
aagacccggt taggaccttt cagggcacgg gcgggtggtg tgtgtgtgtg tgcgtgcgcg    4620
cgcgcccgtg tgtaaaagcc ctagcagaca gttccacact gacacaatgg ggaaactgca    4680
ccagagtgtt tgacactttc cctgaagtca tagaactgta tctgaagtca ttgaactgga    4740
tgtcaaagtg ctcgtagtgt ggagacaggc ggtgtaactc ccagccaact gttagagatg    4800
tttccaagtc ctagtgaagg gccaagctag gcggctgact ggttaggaca gaccctgacc    4860
cctccctgtg tactcttgag acaggtcatg acttgagtct ccgagacaga gaaagaatgt    4920
aggagagttg gggcagggc acagcagaag ctgtacaggc ctgggctctg cagtttacac    4980
tggccaaaga gagattaggg catgctgggt taagaactag ccaggcagtg gtggcgcaca    5040
ccttgatcc cagtattcat gaggcagagg caggcagatc tctttgaggc cagcctgatt    5100
ggagctagtt ctaggaaagc cagggctaca cagagaaacc ctgtctcaac accaccacca    5160
cccccc                                                              5166
```

<210> SEQ ID NO 13  
<211> LENGTH: 311  
<212> TYPE: PRT  
<213> ORGANISM: Mus musculus

<400> SEQUENCE: 13

Met Lys Ala Leu Trp Ala Val Leu Leu Val Thr Leu Leu Thr Gly Cys

```
            1               5                  10                 15
        Leu Ala Glu Gly Glu Pro Glu Val Thr Asp Gln Leu Glu Trp Gln Ser
                        20                 25                 30

Asn Gln Pro Trp Glu Gln Ala Leu Asn Arg Phe Trp Asp Tyr Leu Arg
                        35                 40                 45

Trp Val Gln Thr Leu Ser Asp Val Gln Glu Glu Leu Gln Ser Ser
                        50                 55                 60

Gln Val Thr Gln Glu Leu Thr Ala Leu Met Glu Asp Thr Met Thr Glu
         65                         70                 75                 80

Val Lys Ala Tyr Lys Lys Glu Leu Glu Glu Gln Leu Gly Pro Val Ala
                        85                 90                 95

Glu Glu Thr Arg Ala Arg Leu Gly Lys Glu Val Gln Ala Ala Gln Ala
                        100                105                110

Arg Leu Gly Ala Asp Met Glu Asp Leu Arg Asn Arg Leu Gly Gln Tyr
                        115                120                125

Arg Asn Glu Val His Thr Met Leu Gly Gln Ser Thr Glu Glu Ile Arg
                        130                135                140

Ala Arg Leu Ser Thr His Leu Arg Lys Met Arg Lys Arg Leu Met Arg
        145                150                155                160

Asp Ala Glu Asp Leu Gln Lys Arg Leu Ala Val Tyr Lys Ala Gly Ala
                        165                170                175

Arg Glu Gly Ala Glu Arg Gly Val Ser Ala Ile Arg Glu Arg Leu Gly
                        180                185                190

Pro Leu Val Glu Gln Gly Arg Gln Arg Thr Ala Asn Leu Gly Ala Gly
                        195                200                205

Ala Ala Gln Pro Leu Arg Asp Arg Ala Gln Ala Phe Gly Asp Arg Ile
                        210                215                220

Arg Gly Arg Leu Glu Glu Val Gly Asn Gln Ala Arg Asp Arg Leu Glu
        225                230                235                240

Glu Val Arg Glu His Met Glu Glu Val Arg Ser Lys Met Glu Glu Gln
                        245                250                255

Thr Gln Gln Ile Arg Leu Gln Ala Glu Ile Phe Gln Ala Arg Leu Lys
                        260                265                270

Gly Trp Phe Glu Pro Ile Val Glu Asp Met His Arg Gln Trp Ala Asn
                        275                280                285

Leu Met Glu Lys Ile Gln Ala Ser Val Ala Thr Asn Pro Ile Ile Thr
                        290                295                300

Pro Val Ala Gln Glu Asn Gln
        305                310

<210> SEQ ID NO 14
<211> LENGTH: 317
<212> TYPE: PRT
<213> ORGANISM: Homo sapiens

<400> SEQUENCE: 14

Met Lys Val Leu Trp Ala Ala Leu Leu Val Thr Phe Leu Ala Gly Cys
        1               5                  10                 15

Gln Ala Lys Val Glu Gln Ala Val Glu Thr Glu Pro Glu Pro Glu Leu
                        20                 25                 30

Arg Gln Gln Thr Glu Trp Gln Ser Gly Gln Arg Trp Glu Leu Ala Leu
                        35                 40                 45

Gly Arg Phe Trp Asp Tyr Leu Arg Trp Val Gln Thr Leu Ser Glu Gln
                        50                 55                 60
```

Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 15
<211> LENGTH: 299
<212> TYPE: PRT
<213> ORGANISM: Homo sapiens

<400> SEQUENCE: 15

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Gly Arg Leu Val Gln Tyr Arg Gly Glu Val Gln Ala Met Leu Gly Gln
        115                 120                 125

```
Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
        210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
    290                 295

<210> SEQ ID NO 16
<211> LENGTH: 7
<212> TYPE: PRT
<213> ORGANISM: Simian virus 40

<400> SEQUENCE: 16

Pro Lys Lys Lys Arg Lys Val
1               5

<210> SEQ ID NO 17
<211> LENGTH: 14
<212> TYPE: PRT
<213> ORGANISM: Xenopus laevis

<400> SEQUENCE: 17

Arg Pro Ala Ala Thr Lys Lys Ala Gly Gln Ala Lys Lys Lys
1               5                   10
```

UNITED STATES PATENT AND TRADEMARK OFFICE
CERTIFICATE OF CORRECTION

| | |
|---|---|
| PATENT NO. | : 11,957,115 B2 |
| APPLICATION NO. | : 16/496261 |
| DATED | : April 16, 2024 |
| INVENTOR(S) | : Gareth Howell et al. |

It is certified that error appears in the above-identified patent and that said Letters Patent is hereby corrected as shown below:

In the Claims

At Column 80, in Claim 3, on Line 63:
"Plcb3, Arrb2, 116, Myh10, Gng2, Cnr1, Sty1a, Arrb2,"
Should read:
--Plcb3, Arrb2, Il6, Myh10, Gng2, Cnr1, Sty1a, Arrb2--

Signed and Sealed this
Twenty-eighth Day of May, 2024

Katherine Kelly Vidal
*Director of the United States Patent and Trademark Office*